(12) United States Patent
Krames et al.

(10) Patent No.: US 11,287,090 B2
(45) Date of Patent: Mar. 29, 2022

(54) CIRCADIAN-FRIENDLY LED LIGHT SOURCE

(71) Applicant: ECOSENSE LIGHTING, INC., Los Angeles, CA (US)

(72) Inventors: Michael R. Krames, Mountain View, CA (US); Aurelien J. F. David, San Francisco, CA (US)

(73) Assignee: ECOSENSE LIGHTING INC., Los Angeles, CA (US)

( * ) Notice: Subject to any disclaimer, the term of this patent is extended or adjusted under 35 U.S.C. 154(b) by 0 days.

(21) Appl. No.: 17/157,263

(22) Filed: Jan. 25, 2021

(65) Prior Publication Data

US 2021/0247030 A1    Aug. 12, 2021

Related U.S. Application Data

(63) Continuation of application No. 16/168,471, filed on Oct. 23, 2018, now Pat. No. 10,900,615, which is a
(Continued)

(51) Int. Cl.
*F21K 9/23* (2016.01)
*F21S 4/20* (2016.01)
(Continued)

(52) U.S. Cl.
CPC ............... *F21K 9/23* (2016.08); *A61M 21/02* (2013.01); *A61N 5/0618* (2013.01); *F21K 9/232* (2016.08);
(Continued)

(58) Field of Classification Search
CPC .......... F21K 9/13; F21S 4/003; F21V 23/003; F21W 2101/02; H05B 37/0281; H05B 33/086
See application file for complete search history.

(56) References Cited

U.S. PATENT DOCUMENTS 4,873,696 A    10/1989  Coldren
5,449,930 A    9/1995   Zhou
(Continued)

FOREIGN PATENT DOCUMENTS

CN    101678209    3/2010
CN    203139413    8/2013
(Continued)

OTHER PUBLICATIONS

Caliper, 'Caliper Application Summary Report 22: LED MR16 Lamps', Solid-State Lighting Program, Jun. 2014, pp. 1-25.
(Continued)

*Primary Examiner* — Anne M Hines
(74) *Attorney, Agent, or Firm* — Fisherbroyles LLP

(57) ABSTRACT

Methods and apparatus for providing circadian-friendly LED light sources are disclosed. A light source is formed to include a first LED emission (e.g., one or more LEDs emitting a first spectrum) and a second LED emission (e.g., one or more LEDs emitting a second spectrum) wherein the first and second LED emissions are combined in a first ratio and in a second ratio such that while changing from the first ratio to the second ratio the relative circadian stimulation is varied while maintaining a color rendering index above 80.

22 Claims, 56 Drawing Sheets

Related U.S. Application Data continuation of application No. 16/031,121, filed on Jul. 10, 2018, now Pat. No. 10,137,277, which is a continuation of application No. 15/229,959, filed on Aug. 5, 2016, now Pat. No. 10,076,633, which is a continuation of application No. 14/316,685, filed on Jun. 26, 2014, now Pat. No. 9,410,664.

(60) Provisional application No. 61/871,525, filed on Aug. 29, 2013.

(51) Int. Cl.
| | |
|---|---|
| *H05B 47/16* | (2020.01) |
| *H05B 47/105* | (2020.01) |
| *H05B 45/20* | (2020.01) |
| *F21V 29/70* | (2015.01) |
| *F21K 9/64* | (2016.01) |
| *F21K 9/232* | (2016.01) |
| *F21K 9/235* | (2016.01) |
| *A61M 21/02* | (2006.01) |
| *A61N 5/06* | (2006.01) |
| *F21V 9/08* | (2018.01) |
| *F21V 15/01* | (2006.01) |
| *F21V 19/00* | (2006.01) |
| *F21V 23/00* | (2015.01) |
| *F21Y 105/10* | (2016.01) |
| *F21Y 115/10* | (2016.01) |
| *F21Y 113/13* | (2016.01) |
| *F21V 29/74* | (2015.01) |
| *F21Y 105/18* | (2016.01) |
| *F21K 9/238* | (2016.01) |
| *F21W 107/10* | (2018.01) |
| *A61M 21/00* | (2006.01) |

(52) U.S. Cl.
CPC ............... *F21K 9/235* (2016.08); *F21K 9/64* (2016.08); *F21S 4/20* (2016.01); *F21V 9/08* (2013.01); *F21V 15/01* (2013.01); *F21V 19/006* (2013.01); *F21V 29/70* (2015.01); *H05B 45/20* (2020.01); *H05B 47/105* (2020.01); *H05B 47/16* (2020.01); *A61M 2021/0044* (2013.01); *A61N 2005/0651* (2013.01); *A61N 2005/0663* (2013.01); *F21K 9/238* (2016.08); *F21V 23/003* (2013.01); *F21V 29/74* (2015.01); *F21W 2107/10* (2018.01); *F21Y 2105/10* (2016.08); *F21Y 2105/18* (2016.08); *F21Y 2113/13* (2016.08); *F21Y 2115/10* (2016.08); *Y02B 20/40* (2013.01)

(56) References Cited

U.S. PATENT DOCUMENTS

| | | | |
|---|---|---|---|
| 5,523,589 A | 6/1996 | Edmond | |
| 5,536,953 A | 7/1996 | Dreifus | |
| 5,560,700 A | 10/1996 | Levens | |
| 5,578,404 A | 11/1996 | Kliem | |
| 6,150,774 A | 11/2000 | Mueller | |
| 6,288,417 B1 | 9/2001 | Nickel | |
| 6,300,557 B1 | 10/2001 | Wanlass | |
| 6,498,440 B2 | 12/2002 | Stam | |
| 6,509,651 B1 | 1/2003 | Matsubara | |
| 6,573,537 B1 | 6/2003 | Steigerwald | |
| 6,853,010 B2 | 2/2005 | Slater, Jr. | |
| 6,967,116 B2 | 11/2005 | Negley | |
| 7,005,679 B2 | 2/2006 | Tarsa | |
| 7,027,015 B2 | 4/2006 | Booth, Jr. | |
| 7,038,399 B2 | 5/2006 | Lys | |
| 7,067,985 B2 | 6/2006 | Adachi | |
| 7,067,995 B2 | 6/2006 | Gunter | |
| 7,083,302 B2 | 8/2006 | Chen | |
| 7,095,056 B2 | 8/2006 | Vitta | |
| 7,113,658 B2 | 9/2006 | Ide | |
| 7,173,384 B2 | 2/2007 | Plotz | |
| 7,183,577 B2 | 2/2007 | Mueller-Mach | |
| 7,211,822 B2 | 5/2007 | Nagahama | |
| 7,213,940 B1 | 5/2007 | Van De Ven | |
| 7,233,831 B2 | 6/2007 | Blackwell | |
| 7,250,715 B2 | 7/2007 | Mueller | |
| 7,253,446 B2 | 8/2007 | Sakuma | |
| 7,352,138 B2 | 4/2008 | Lys | |
| 7,358,679 B2 | 4/2008 | Lys | |
| 7,361,938 B2 | 4/2008 | Mueller | |
| 7,419,281 B2 | 9/2008 | Porchia et al. | |
| 7,521,862 B2 | 4/2009 | Mueller | |
| 7,564,180 B2 | 7/2009 | Brandes | |
| 7,622,742 B2 | 11/2009 | Kim | |
| 7,646,033 B2 | 1/2010 | Tran | |
| 7,679,281 B2 | 3/2010 | Kim | |
| 7,748,845 B2 | 7/2010 | Casper | |
| 7,846,757 B2 | 12/2010 | Farrell, Jr. | |
| 7,884,538 B2 | 2/2011 | Mitsuishi | |
| 7,902,564 B2 | 3/2011 | Mueller-Mach | |
| 8,028,706 B2 | 10/2011 | Skene | |
| 8,124,996 B2 | 2/2012 | Raring | |
| 8,269,245 B1 | 9/2012 | Shum | |
| 8,299,473 B1 | 10/2012 | D Evelyn | |
| 8,310,143 B2 | 11/2012 | Van De Ven | |
| 8,399,898 B2 | 3/2013 | Jagt | |
| 8,410,714 B2 | 4/2013 | Kasakuraakeo | |
| 8,502,465 B2 | 8/2013 | Katona | |
| 8,506,114 B2 | 8/2013 | Van De Ven | |
| 8,506,612 B2 | 8/2013 | Ashdown | |
| 8,508,127 B2 | 8/2013 | Negley | |
| 8,525,396 B2 | 9/2013 | Shum | |
| 8,575,642 B1 | 11/2013 | Shum | |
| D694,722 S | 12/2013 | Shum | |
| 8,618,560 B2 | 12/2013 | D Evelyn | |
| 8,643,038 B2 | 2/2014 | Collins | |
| 8,646,939 B2 | 2/2014 | Bues | |
| 8,686,458 B2 | 4/2014 | Krames | |
| 8,704,258 B2 | 4/2014 | Tasaki | |
| 8,740,413 B1 | 6/2014 | Krames | |
| 8,829,774 B1 | 9/2014 | Shum | |
| 8,905,588 B2 | 12/2014 | Krames | |
| 8,921,875 B2 | 12/2014 | Letoquin | |
| 8,933,644 B2 | 1/2015 | David | |
| 9,192,013 B1 | 11/2015 | Van De Ven | |
| 9,289,622 B2 | 3/2016 | Feng | |
| 9,370,669 B2 | 6/2016 | Park | |
| 9,374,876 B2 | 6/2016 | Alpert | |
| 9,410,664 B2 | 8/2016 | Krames | |
| 9,474,119 B1 | 10/2016 | Chen | |
| 9,526,143 B1 | 12/2016 | Petluri | |
| 9,543,363 B2 | 1/2017 | Baek | |
| 9,827,440 B2 | 11/2017 | Moore-Ede | |
| 9,900,957 B2 | 2/2018 | Van De Ven | |
| 9,990,722 B2 | 6/2018 | Kim | |
| 10,039,169 B2 | 7/2018 | Chen | |
| 10,113,700 B2 | 10/2018 | Soer | |
| 10,128,415 B2 | 11/2018 | Huang | |
| 10,269,285 B2 | 4/2019 | Lee | |
| 10,401,683 B2 | 9/2019 | David | |
| 10,416,496 B2 | 9/2019 | Yang | |
| 10,475,363 B2 | 11/2019 | Chen | |
| 10,485,070 B2 | 11/2019 | Chen | |
| 10,747,056 B2 | 8/2020 | Yang | |
| 10,805,998 B2 | 10/2020 | Petluri | |
| 10,946,211 B2 | 3/2021 | Hommes | |
| 11,073,727 B2 | 7/2021 | David | |
| 2001/0055208 A1 | 12/2001 | Koichi | |
| 2002/0063258 A1 | 5/2002 | Motoki | |
| 2002/0088985 A1 | 7/2002 | Komoto | |
| 2003/0012246 A1 | 1/2003 | Klimek | |
| 2003/0030063 A1 | 2/2003 | Sosniak | |
| 2004/0031437 A1 | 2/2004 | Sarayama | |
| 2004/0070736 A1* | 4/2004 | Roddy | ............. H04N 9/3158 353/31 |

(56) References Cited

U.S. PATENT DOCUMENTS

| | | |
|---|---|---|
| 2004/0080938 A1 | 4/2004 | Holman |
| 2004/0104391 A1 | 6/2004 | Maeda |
| 2004/0201598 A1 | 10/2004 | Eliav |
| 2004/0207998 A1 | 10/2004 | Suehiro |
| 2004/0251471 A1 | 12/2004 | Dwilinski |
| 2005/0030760 A1 | 2/2005 | Capello |
| 2005/0084218 A1 | 4/2005 | Ide |
| 2005/0109240 A1 | 5/2005 | Maeta |
| 2005/0179376 A1 | 8/2005 | Fung |
| 2006/0060872 A1 | 3/2006 | Edmond |
| 2006/0078022 A1 | 4/2006 | Kozaki |
| 2006/0106437 A1 | 5/2006 | Czeisler |
| 2006/0108162 A1 | 5/2006 | Tabata |
| 2006/0149607 A1 | 7/2006 | Sayers |
| 2006/0208262 A1 | 9/2006 | Sakuma |
| 2006/0221272 A1 | 10/2006 | Negley |
| 2006/0262545 A1 | 11/2006 | Piepgras |
| 2006/0273339 A1 | 12/2006 | Steigerwald |
| 2007/0007898 A1 | 1/2007 | Bruning |
| 2007/0012944 A1 | 1/2007 | Bader |
| 2007/0114561 A1 | 5/2007 | Comanzo |
| 2007/0126023 A1 | 6/2007 | Haskell |
| 2007/0139920 A1 | 6/2007 | Van De Ven |
| 2007/0210074 A1 | 9/2007 | Maurer |
| 2007/0228404 A1 | 10/2007 | Tran |
| 2007/0231963 A1 | 10/2007 | Doan |
| 2007/0240346 A1 | 10/2007 | Li |
| 2007/0268234 A1 | 11/2007 | Wakabayashi |
| 2008/0006837 A1 | 1/2008 | Park |
| 2008/0048200 A1 | 2/2008 | Mueller |
| 2008/0083741 A1 | 4/2008 | Giddings |
| 2008/0087919 A1 | 4/2008 | Tysoe |
| 2008/0099777 A1 | 5/2008 | Erchak |
| 2008/0100551 A1 | 5/2008 | Haga |
| 2008/0108162 A1 | 5/2008 | Dwilinski |
| 2008/0116786 A1 | 5/2008 | Wang |
| 2008/0158887 A1 | 7/2008 | Zhu |
| 2008/0173882 A1 | 7/2008 | Parikh |
| 2008/0179611 A1 | 7/2008 | Chitnis |
| 2008/0187746 A1 | 8/2008 | De Graaf |
| 2008/0192791 A1 | 8/2008 | Furukawa |
| 2008/0211389 A1 | 9/2008 | Oshio |
| 2008/0218759 A1 | 9/2008 | Colvin |
| 2008/0231214 A1 | 9/2008 | Kim |
| 2009/0281604 A1 | 11/2009 | De Boer |
| 2010/0217358 A1 | 8/2010 | Hebert |
| 2010/0264850 A1 | 10/2010 | Yamamoto |
| 2011/0068698 A1 | 3/2011 | Swiboda et al. |
| 2012/0069551 A1 | 3/2012 | Bues |
| 2012/0140466 A1 | 6/2012 | Yang |
| 2012/0259392 A1 | 10/2012 | Feng |
| 2014/0268152 A1 | 9/2014 | Morrow |
| 2015/0116997 A1 | 4/2015 | Tappert |
| 2015/0237688 A1 | 8/2015 | Gambeski |
| 2016/0023017 A1 | 1/2016 | Moore-Ede |
| 2017/0138570 A1 | 5/2017 | Ouderkirk |
| 2018/0016088 A1 | 1/2018 | Conway |
| 2019/0209858 A1 | 7/2019 | Slaughter |
| 2019/0385506 A1 | 12/2019 | Andrivon |
| 2020/0368550 A1 | 11/2020 | Moore-Ede |
| 2021/0060353 A1 | 3/2021 | Petluri |

FOREIGN PATENT DOCUMENTS

| | | |
|---|---|---|
| CN | 106449626 A | 2/2017 |
| CN | 107167962 A | 9/2017 |
| CN | 110970409 A | 4/2020 |
| CN | 108877690 B | 1/2021 |
| CN | 112233609 A | 1/2021 |
| DE | 112011102386 | 4/2013 |
| DE | 102017204086 A1 | 9/2018 |
| JP | H11503838 | 3/1999 |
| JP | 2005063687 A | 3/2005 |
| JP | 2006119295 | 5/2006 |
| JP | 2006299097 | 11/2006 |
| JP | 2007214603 | 8/2007 |
| JP | 2008235903 A | 10/2008 |
| JP | 2009532856 | 9/2009 |
| JP | 2009533127 | 9/2009 |
| JP | 2009238729 | 10/2009 |
| JP | 2009259639 | 11/2009 |
| JP | 2011176300 | 9/2011 |
| JP | 2012178538 | 9/2012 |
| KR | 20120091114 | 8/2012 |
| KR | 101574063 B1 | 12/2015 |
| WO | 2007114614 | 10/2007 |
| WO | 2007116341 | 10/2007 |
| WO | 2008069101 A1 | 6/2008 |
| WO | 2013125521 A1 | 8/2013 |
| WO | 2018176533 A1 | 10/2018 |
| WO | 2020155841 A1 | 8/2020 |
| WO | 2021135752 A1 | 7/2021 |

OTHER PUBLICATIONS

Chhajed et al., 'Junction temperature in light-emitting diodes assessed by different methods', Future Chips Constellation, 2005, p. 1-9.

Chinese Notification to Grant Patent Rights for Inventtion, dated Feb. 26, 2020, in Chinese Application No. 201410437145.8, including English machine translation, 6 pages.

Chinese Office Action (with English language translation) for Application No. 2014104371458, dated Jun. 5, 2019, 7 pages.

Chinese Office Action dated Sep. 25, 2019, in Chinese Application No. 201410437145.8, including English language translation, 6 pages.

Chinese Search Report (with English language translation) for Application No. 2014104371458, dated May 24, 2019, 4 pages.

Cich et al., 'Bulk GaN based violet light-emitting diodes with high efficiency at very high current density', Applied Physics Letters, 101, Nov. 29, 2012, pp. 223509-1-223509-3.

Communication from the Japanese Patent Office re 2012-529969 dated Dec. 5, 2014 (2 pages).

Communication from the Japanese Patent Office re 2012-529969 dated Jul. 4, 2014 (8 pages).

Communication from the Japanese Patent Office re 2012-529969, dated Oct. 15, 2013, (6 pages).

Communication from the Japanese Patent Office re 2013-263760 dated Nov. 14, 2014 (11 pages).

Communication from the Japanese Patent Office re 2013097298 dated Jun. 6, 2014 (7 pages).

Csuti et al., 'Color-matching experiments with RGB-LEDs', Color Research and Application, vol. 33, No. 2, 2008, pp. 1-9.

David et al., 'Carrier distribution in (0001)InGaN/GaN multiple quantam well light-emitting diodes', Applied Physics Letters, vol. 92, No. 053502, Feb. 4, 2008, pp. 1-3.

David et al., 'Influence of polarization fields on carrier lifetime and recombination rates in InGaN-based light-emitting diodes', Applied Physics Letters, vol. 97, No. 033501, Jul. 19, 2010, pp. 1-3.

Davis et al., 'Color quality scale', Optical Engineering, vol. 49, No. 3, Mar. 2010, pp. 033602-1-036602-16.

Gardner et al., 'Blue-Emitting InGaN-GaN Double-Heterostructure Light-Emitting Diodes Reaching Maximum Quantum Efficiency Above 200 A/cm2', Applied Physics Letters. vol. 91, 2007, pp. 243506-1-243506-3.

Houser et al., 'Review of measures for light-source color rendition and considerations for a two-measure system for characterizing color rendition', Optics Express, vol. 21, No. 8, Apr. 19, 2013, pp. 10393-10411.

http://www.philipslumileds.com/products/luxeon-flash, 'Luxeon Flash', Philips Lumileds, Aug. 8, 2013, pp. 1-2; Retrieved on Sep. 21, 2013.

Japanese Notice of Allowance dated Jan. 23, 2019 in Japanese Application No. 2014-174472, including English machine translation, 5 pages.

Japanese Office Action dated Nov. 24, 2020, in Application No. 2019-024827, including English machine translation, 6 pages.

Korean Notification of Reason for Refusal dated Aug. 28, 2018, in Korean Application No. 10-2014-0114140, including English language machine translation, 10 pages.

(56) References Cited

OTHER PUBLICATIONS

Madelung, 'III-V Compounds', Semiconductors: Data Handbook, Springer Verlag, Berlin-Heidelberg, vol. 3, Ch. 2, 2004, pp. 71-172.
Masui et al., 'Electrical Characteristics of Nonpolar InGaN-Based Light-Emitting Diodes Evaluated at Low Temperature', Japanese Journal of Applied Physics, vol. 46, No. 11, 2007, pp. 7309-7310.
Michiue et al., 'Recent Development of Nitride LEDs and LDs', Proceedings of SPIE, vol. 7216, 2009, pp. 72161Z-1-72161Z-6.
Narendran et al., 'Color Rendering Properties of LED Light Sources', Solid State Lighting II: Proceedings of SPIE, 2002, pp. 1-8.
Narukawa et al., 'White light emitting diodes with super-high luminous efficacy', Journal of Physics D: Applied Physics, vol. 43, No. 354002, Aug. 19, 2010, pp. 1-6.
Office Action dated Mar. 3, 2020, for Japanese Application No. 2019-024827, including English machine translation (8 pages).
Paper and Board Determination of CIE Whiteness, D65/10 (outdoor daylight), ISO International Standard 11475:2004E (2004), 18 pgs.
Rea et al., 'White Lighting', COLOR Research and Application, vol. 38, No. 2, Sep. 3, 2011, pp. 82-92.
Sato et al., 'High Power and High Efficiency Semipolar InGaN Light Emitting Diodes', Journal of Light and Visible Environment, vol. 32, No. 2, Dec. 13, 2007, pp. 57-60.
Sato et al., 'High Power And High Efficiency Semipolar InGaN Light Emitting Diodes', Journal of Light and Visible Environment, vol. 32, No. 2, Feb. 12, 2008, pp. 107-110.
Shen et al., 'Auger Recombination in Letters InGaN Measured by Photoluminescence', Applied Physics Letters, vol. 91, 2007, pp. 141101-1-141101-3.
Stefani et al., Evaluation of Human Reactions on Displays with LED Backlight and a Technical Concept of a Circadian Effective Display, SID 10 Digest, ISSN 0097-966X/10/4102-1120, 2010, 4 pgs.
Tomiya et al., 'Dislocation Related Issues In The Degradation of GaN-Based Laser Diodes', IEEE Journal of Selected Topics in Quantum Electronics, vol. 10, No. 6, 2004, pp. 1277-1287.
Weaver et al., 'Optical Properties of Selected Elements', Handbook of Chemistry and Physics, vol. 94, 2013-2014, pp. 12-126-12-140.
Whitehead et al., A Monte Carlo method for assessing color rendering quality with possible application to color rendering standards', Color Research and Application, vol. 37, No. 1, Feb. 2012, pp. 13-22.
Korean Office Action dated Jun. 17, 2021, in Korean Application No. 10-2021-0021040, including English language translation.
Chinese Office Action dated Oct. 9, 2021 in Chinese Application No. 202109290266914.0, including English translation.
German Office Action dated Dec. 2, 2021, in Application No. 10 2014110 833.7, including English language translation.
Korean Office Action dated Dec. 29, 2021, in Application No. 10-2021-0114830, including English language translation.

* cited by examiner

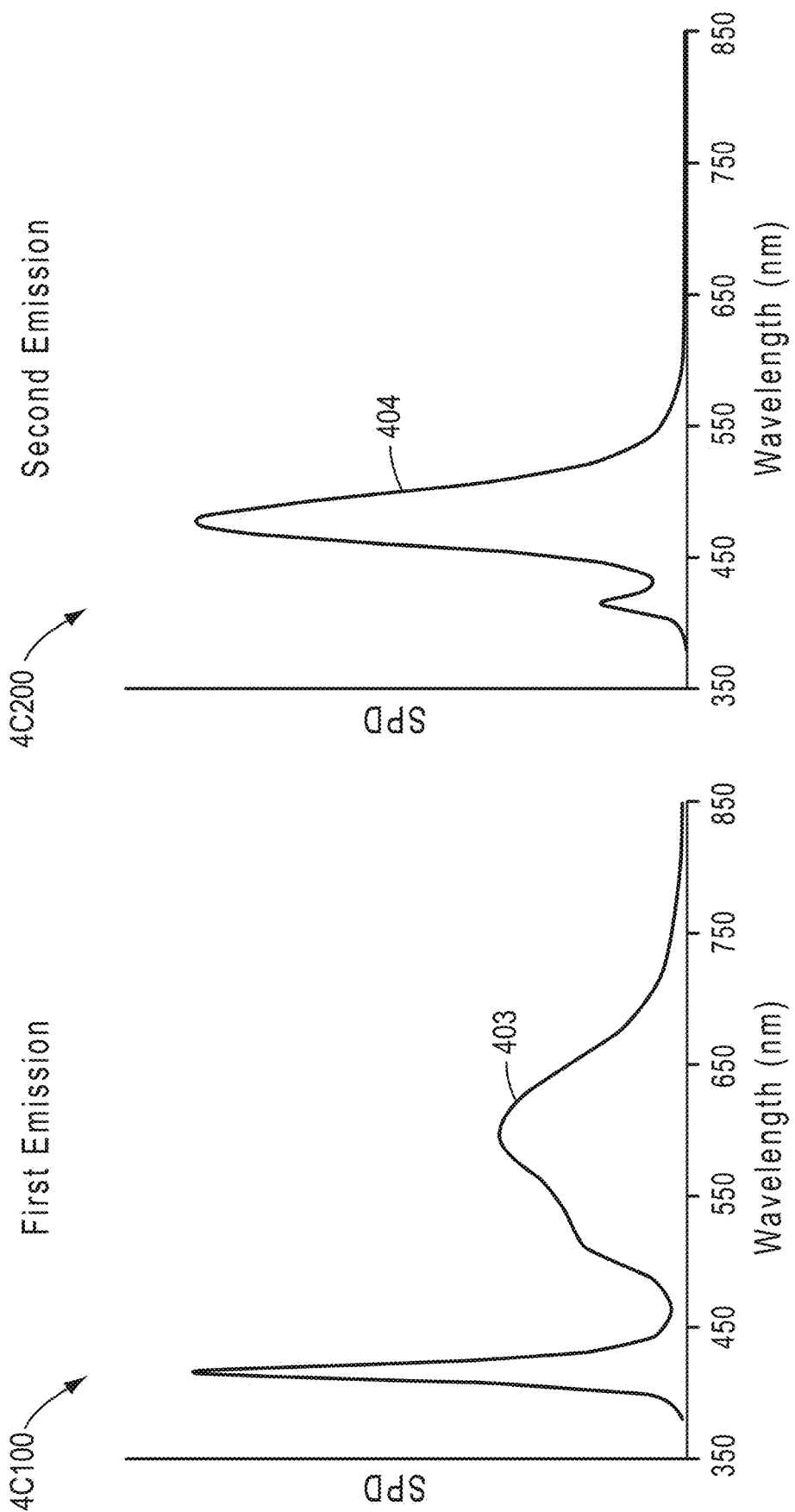
FIG. 4C2
FIG. 4C1

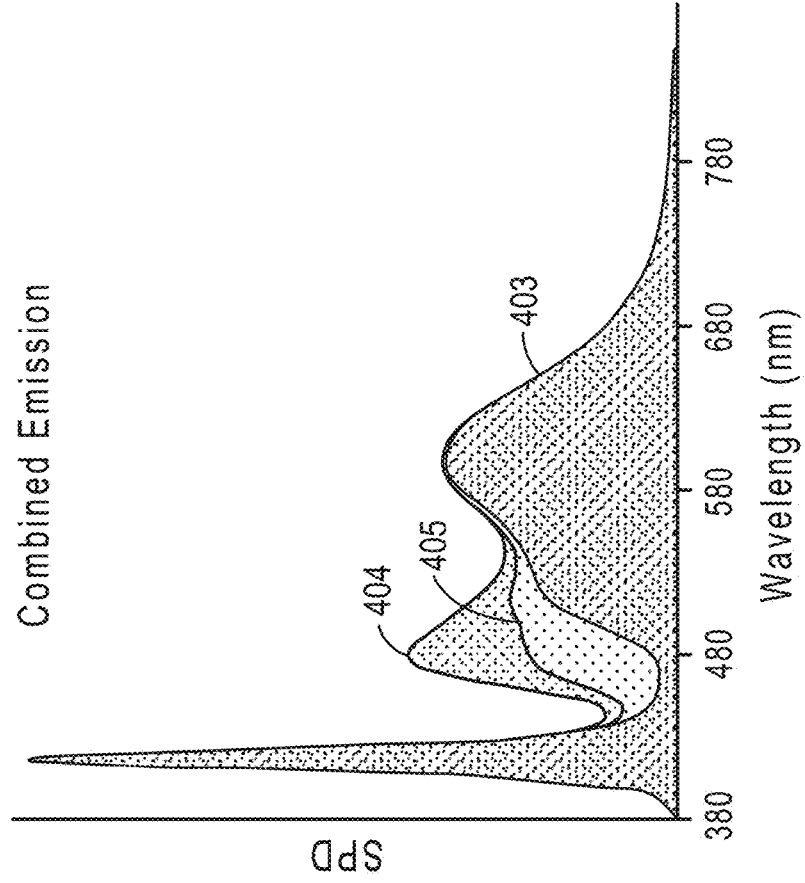
FIG. 4D1
FIG. 4D2
| Ratio 2nd : 1st | 0% | 50% | 100% |
|---|---|---|---|
| CS (rel. to CIE A)* | 50% | 187% | 305% |
| x | 0.417 | 0.374 | 0.342 |
| y | 0.394 | 0.365 | 0.343 |
| u' | 0.241767 | 0.225374 | 0.212363 |
| v' | 0.514472 | 0.495292 | 0.480071 |
| CCT [K] | 3286 | 4105 | 5108 |
| Duv | -0.00081 | -0.00358 | -0.00284 |
| LER [lm/W] | 266 | 252 | 241 |
| CRI (Ra) | 80 | 93 | 91 |
| R9 | 10 | 45 | 70 |
| Fraction in VB range | 23% | 21% | 19% |
| Fraction in BC range | 5% | 13% | 20% |
* Using Gaussian CSWR peaked at 465nm with FWHM of 30nm

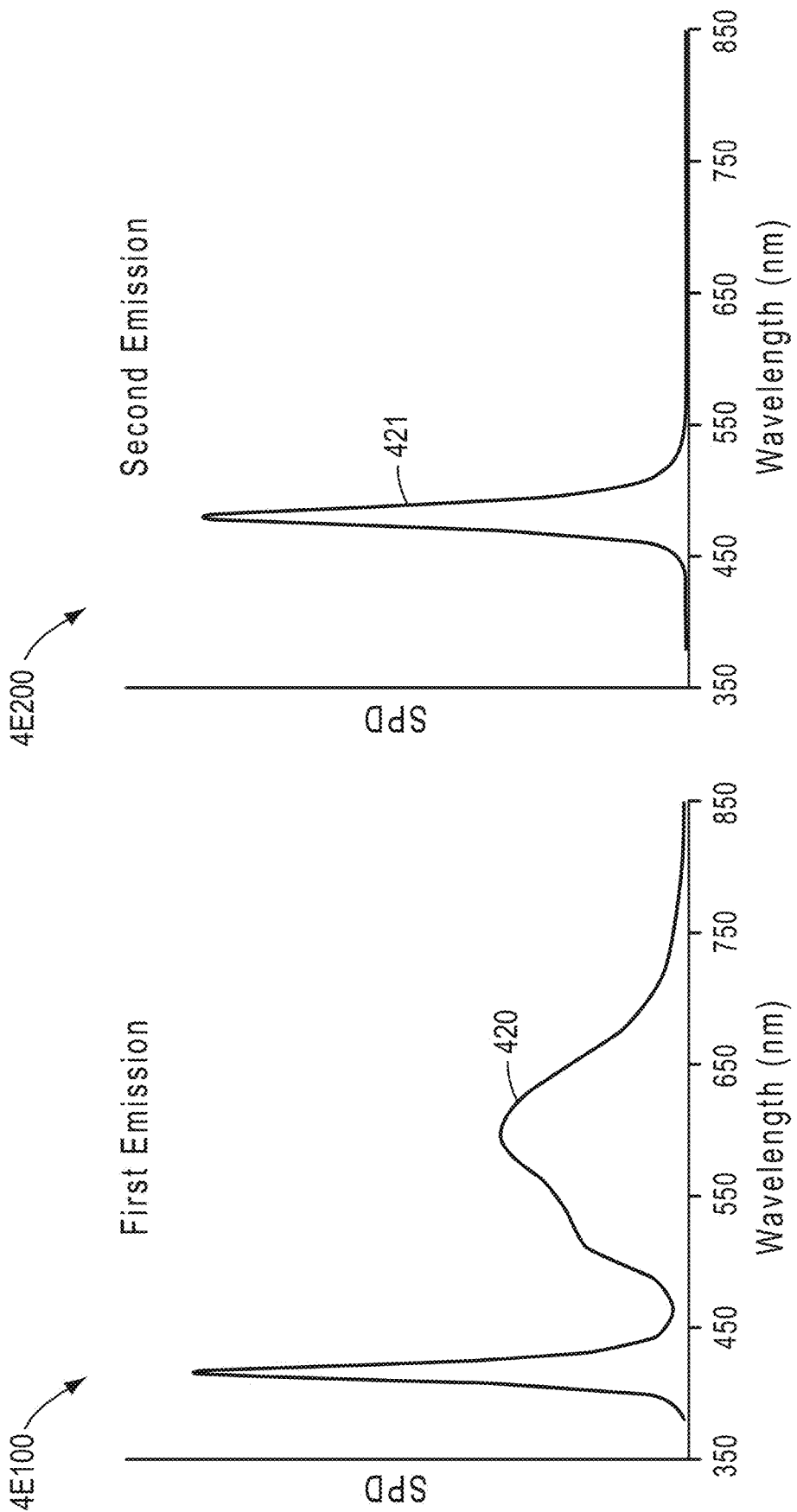

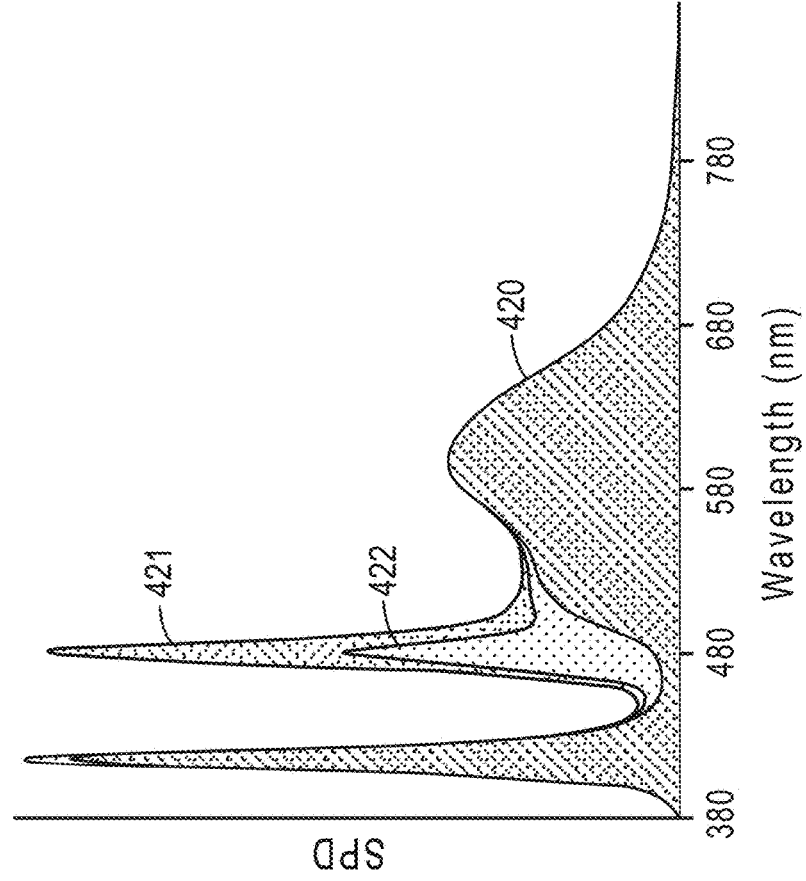
FIG. 4F1
FIG. 4F2

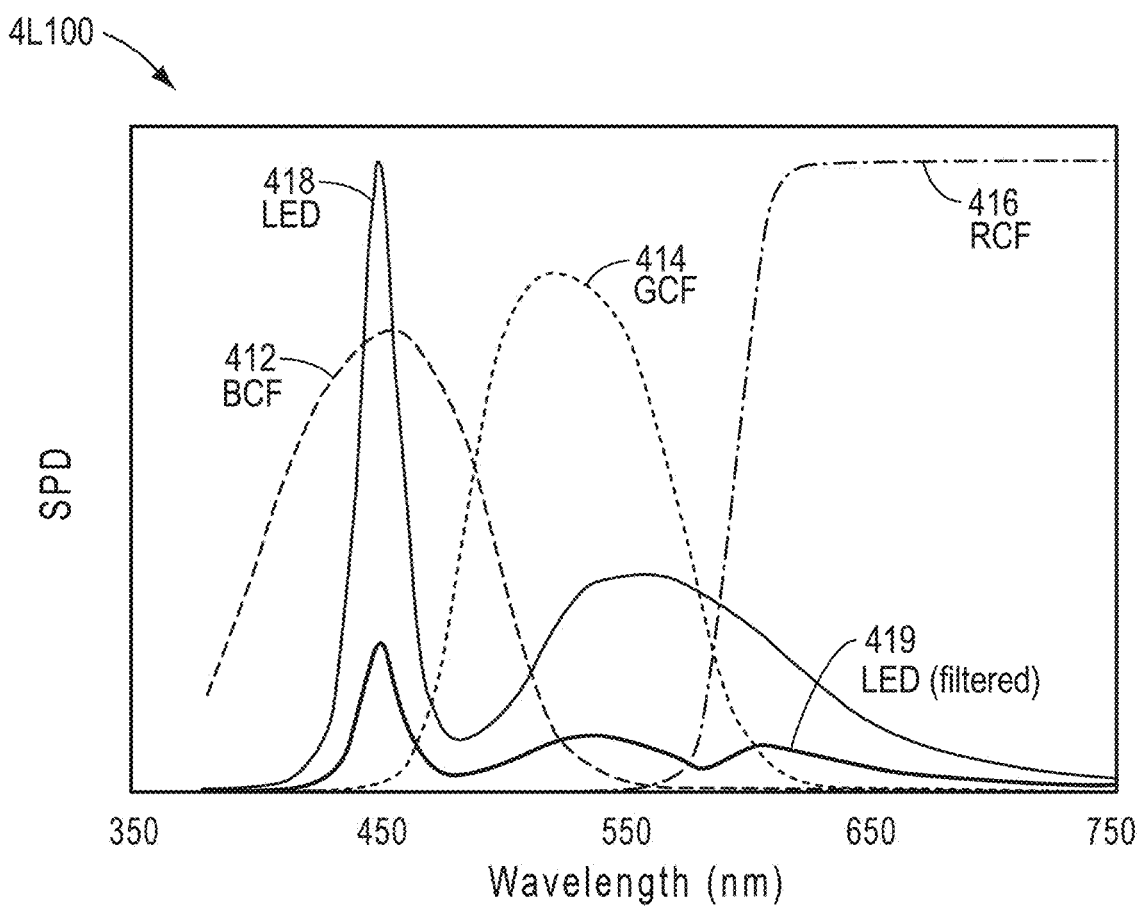
FIG. 4L1

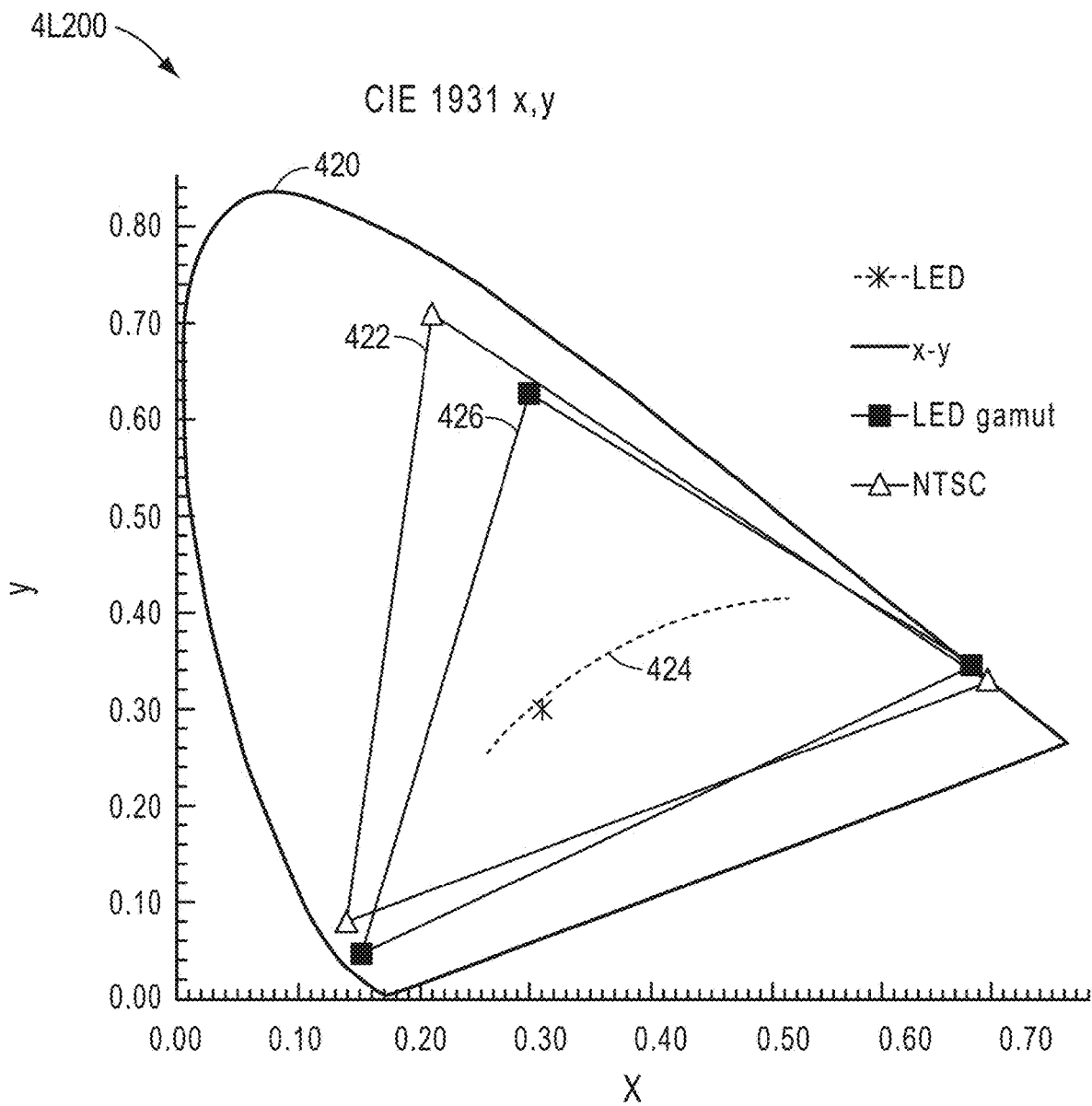
FIG. 4L2

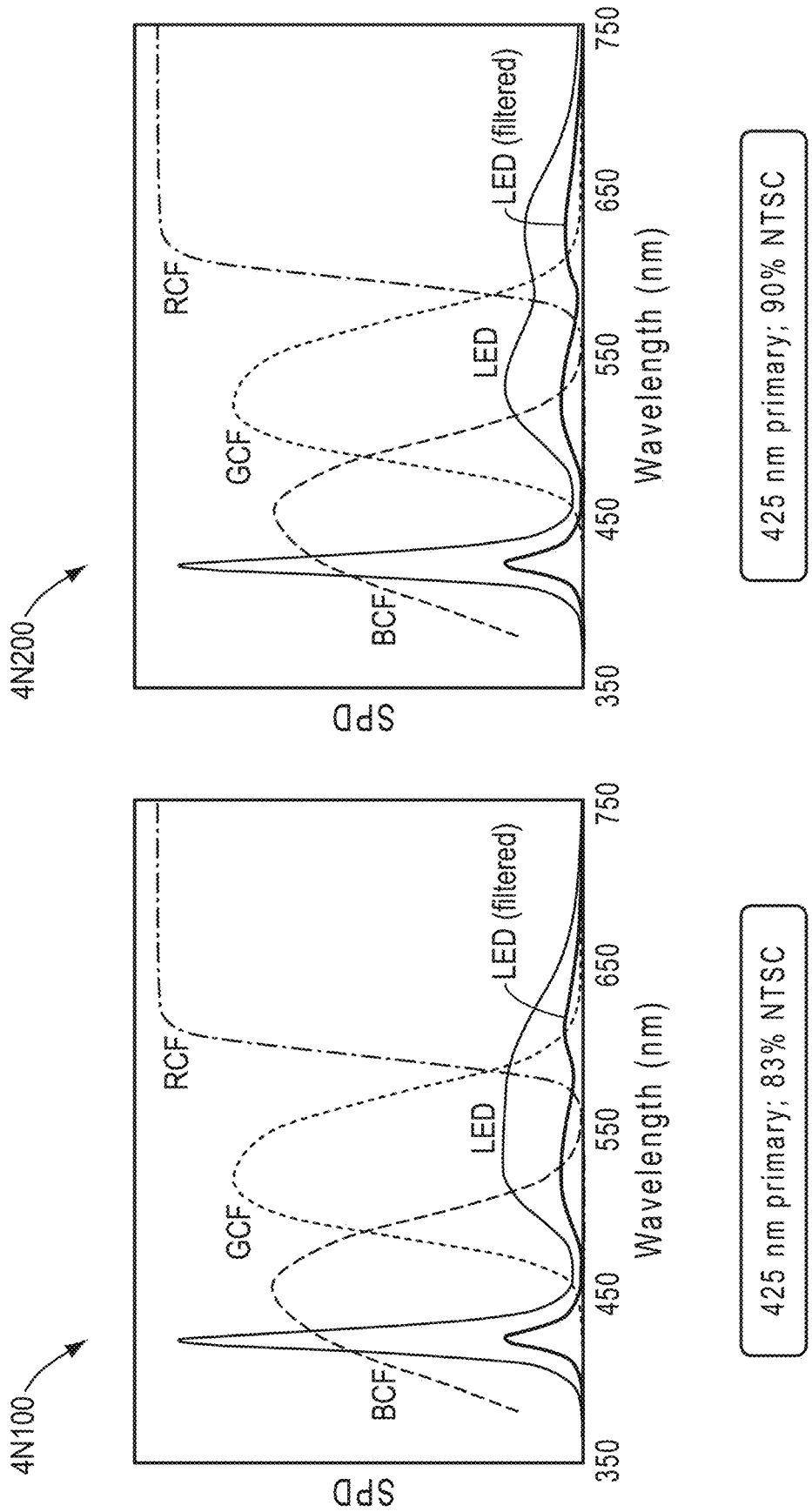

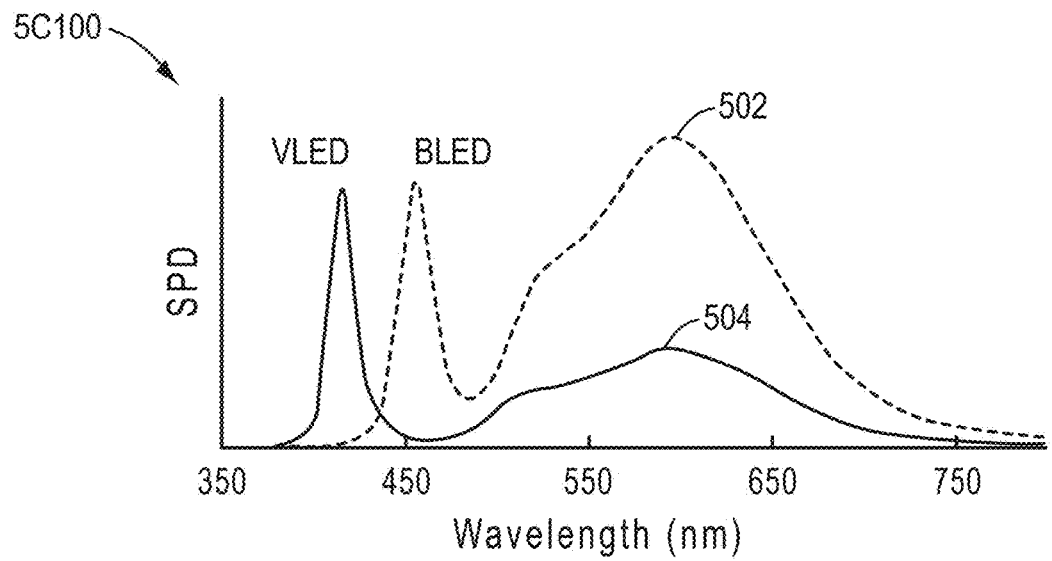
FIG. 5C1
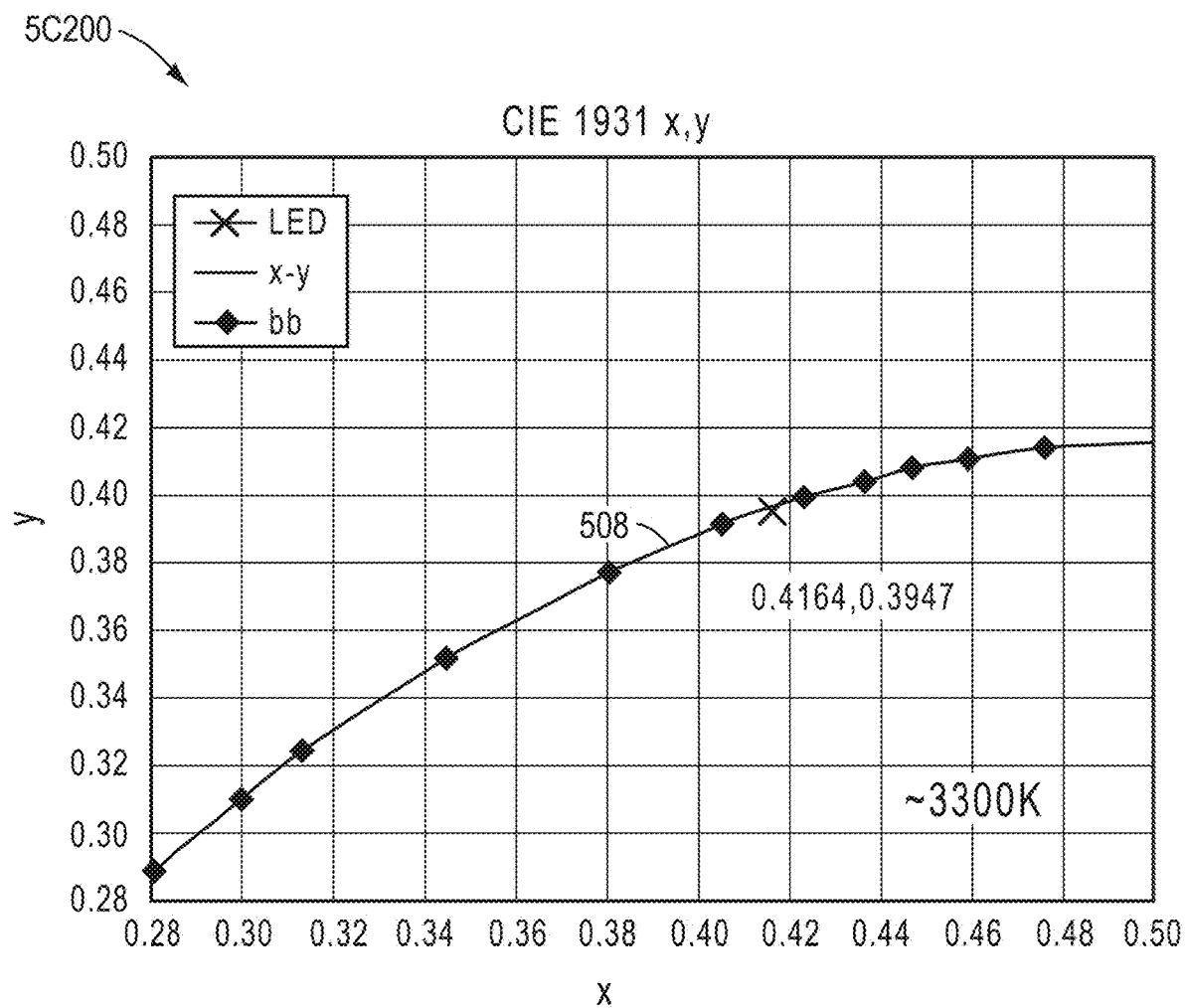
FIG. 5C2

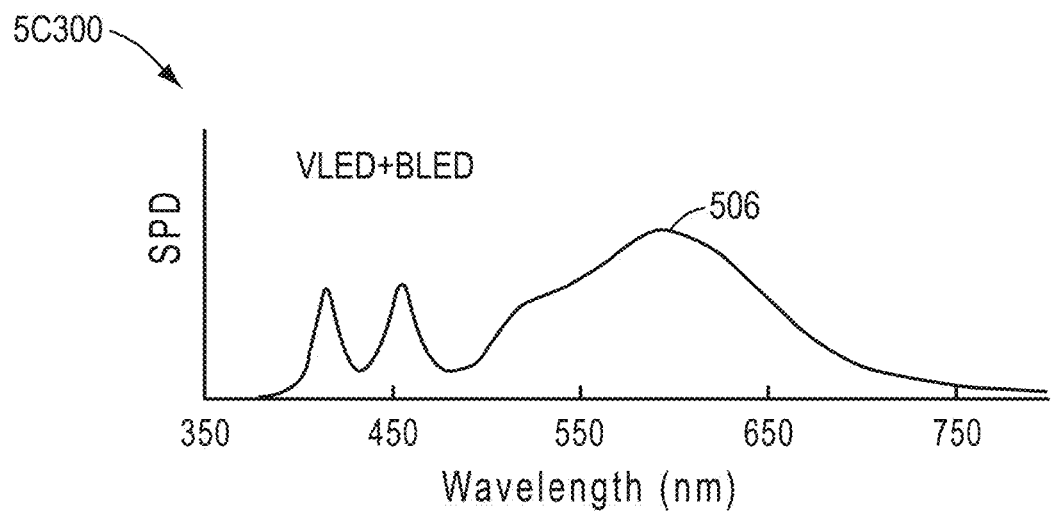
FIG. 5C3
| BLED Fraction | Circadian Stimulation (relative to CIE A)* |
|---|---|
| 0% | 54% |
| 20% | 123% |
| 50% | 172% |
| 100% | 210% |
FIG. 5C4

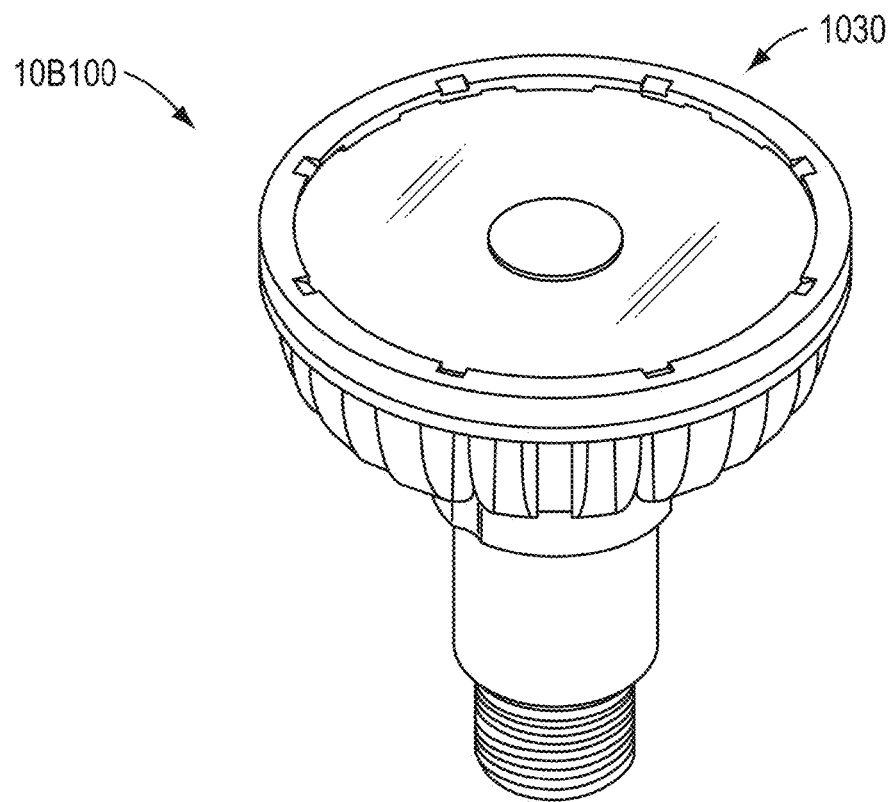
FIG. 10B1
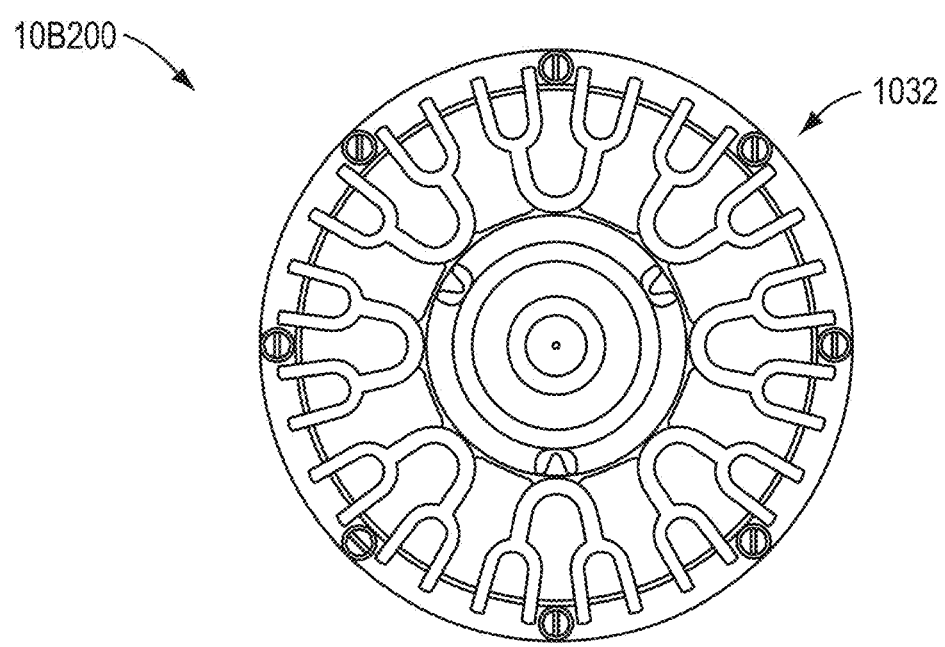
FIG. 10B2

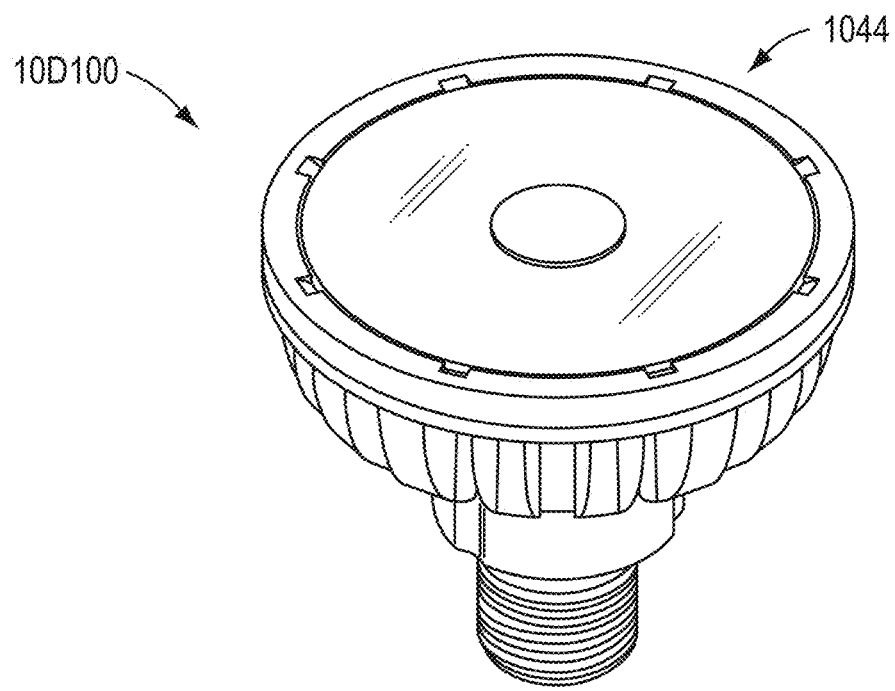
FIG. 10D1
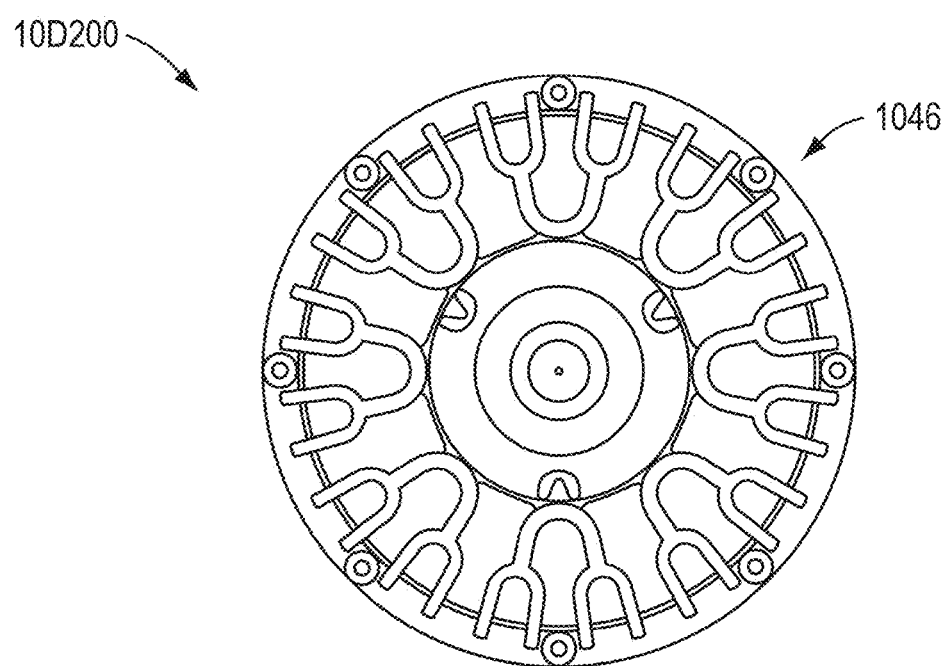
FIG. 10D2

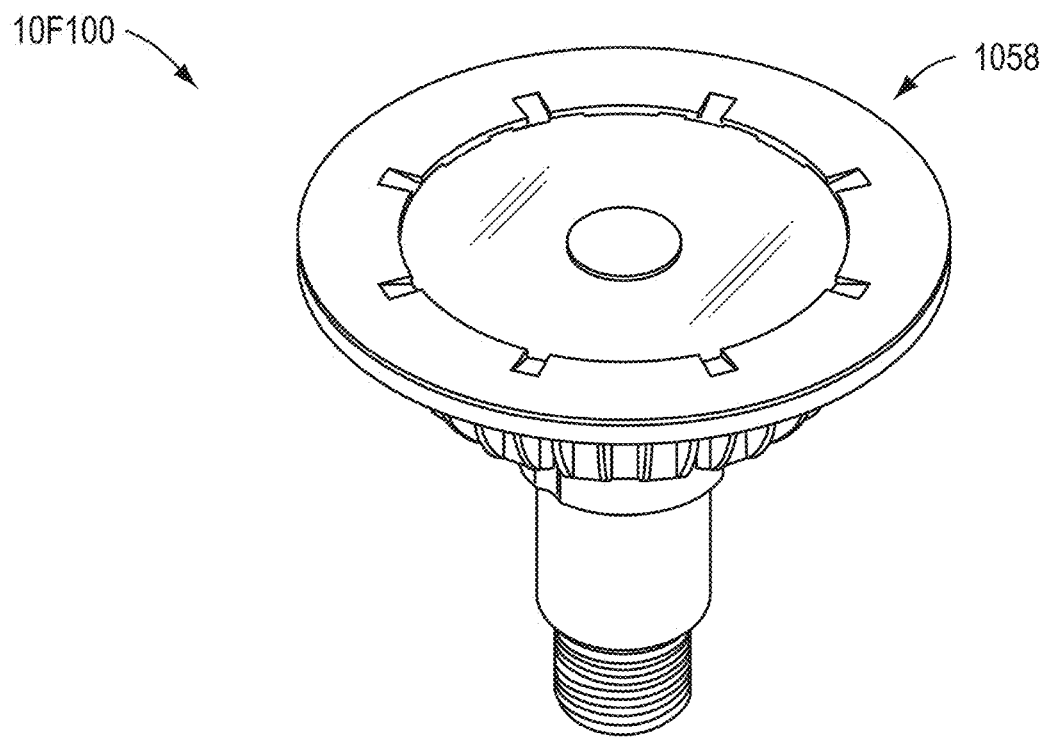
FIG. 10F1
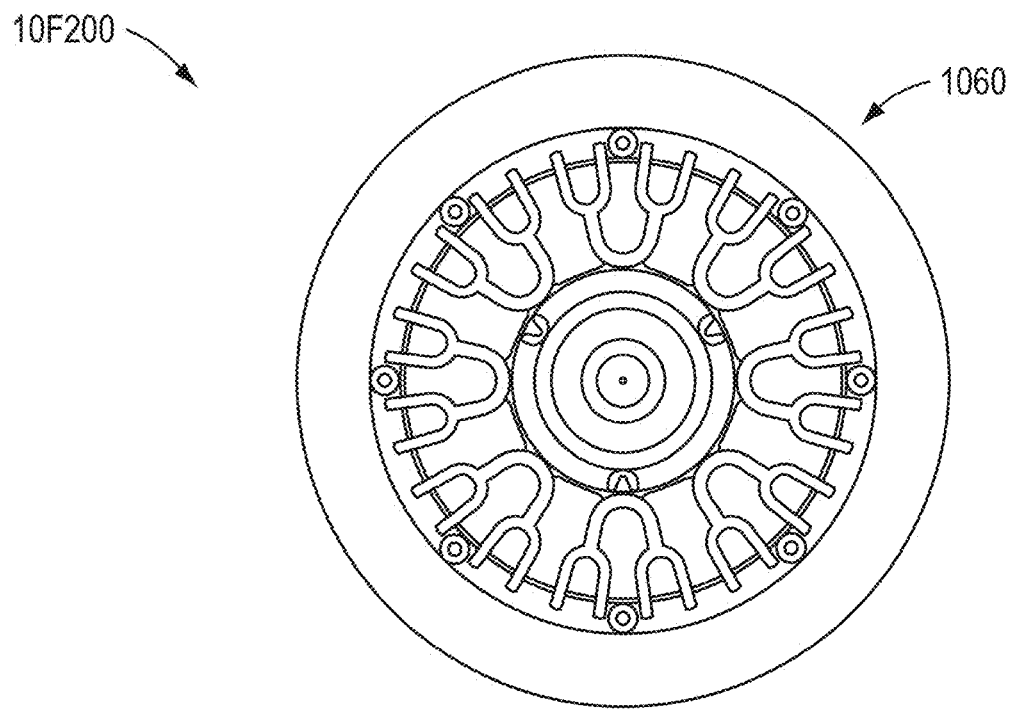
FIG. 10F2

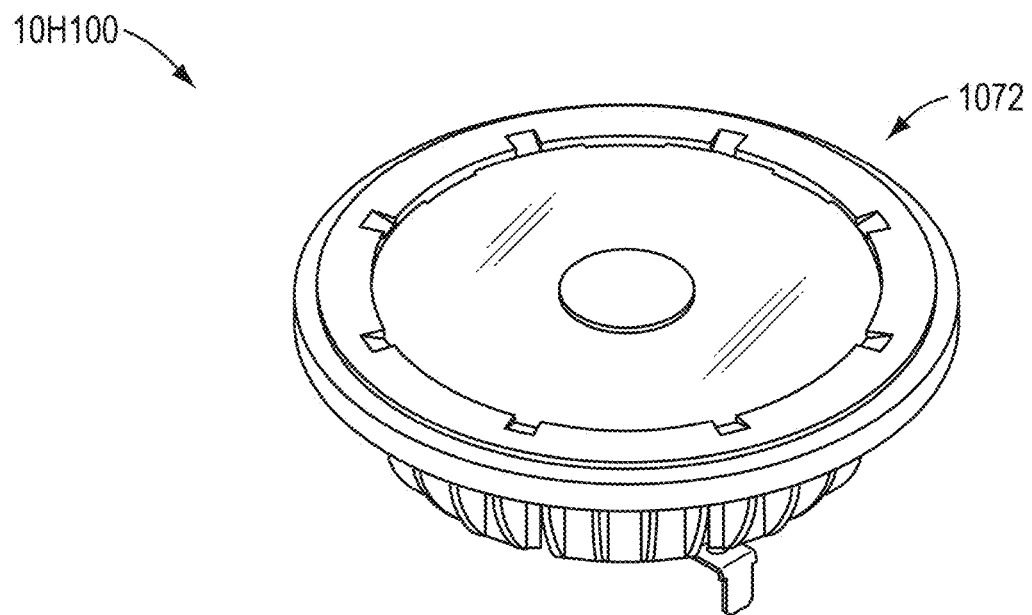
FIG. 10H1
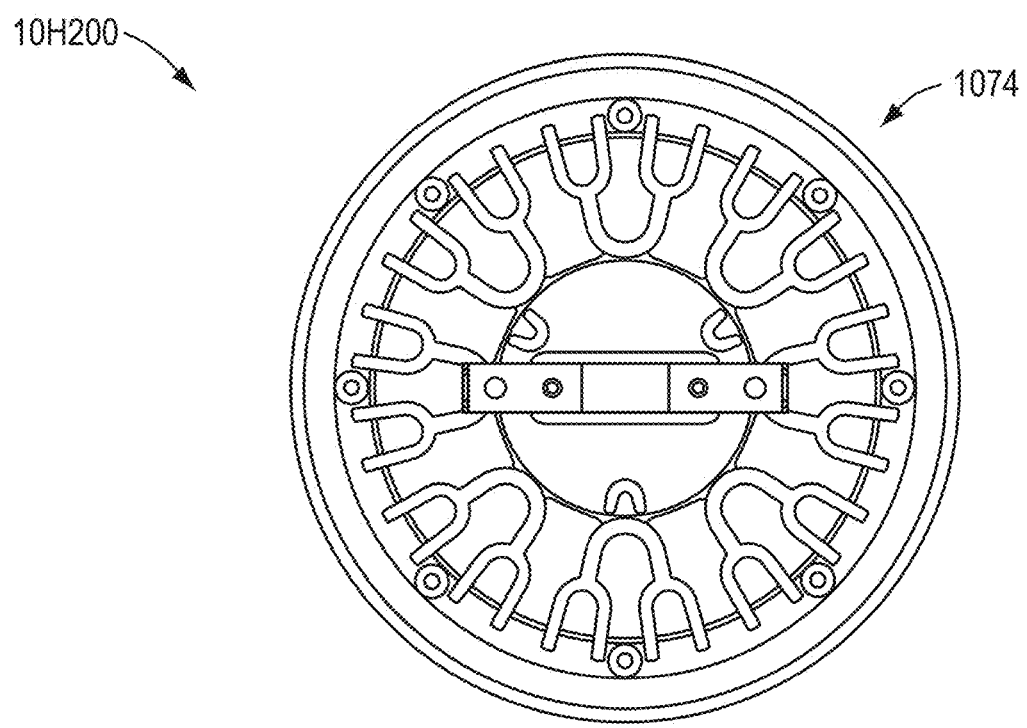
FIG. 10H2

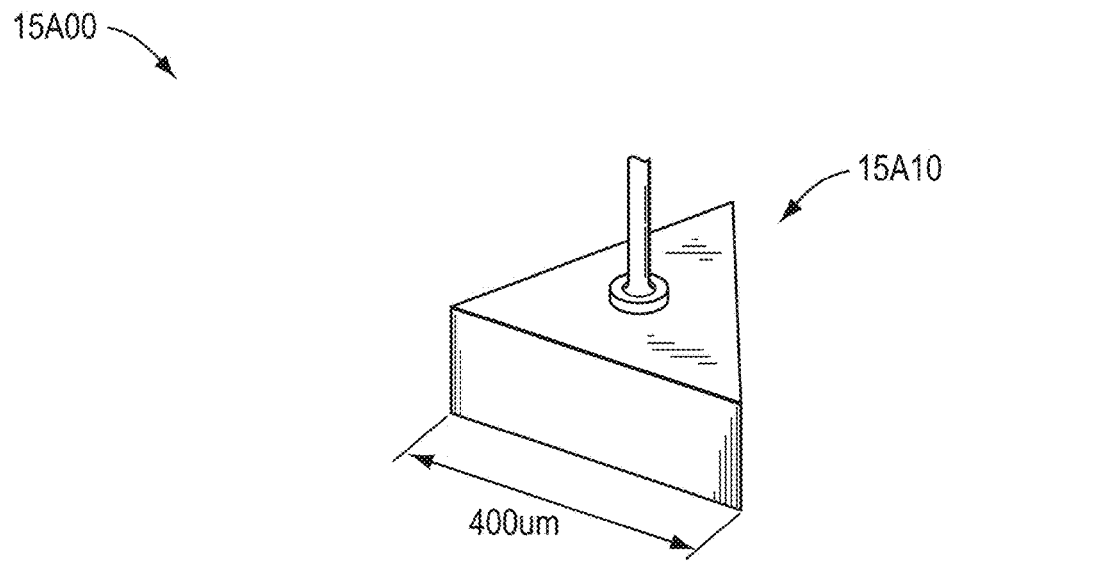
FIG. 15A1
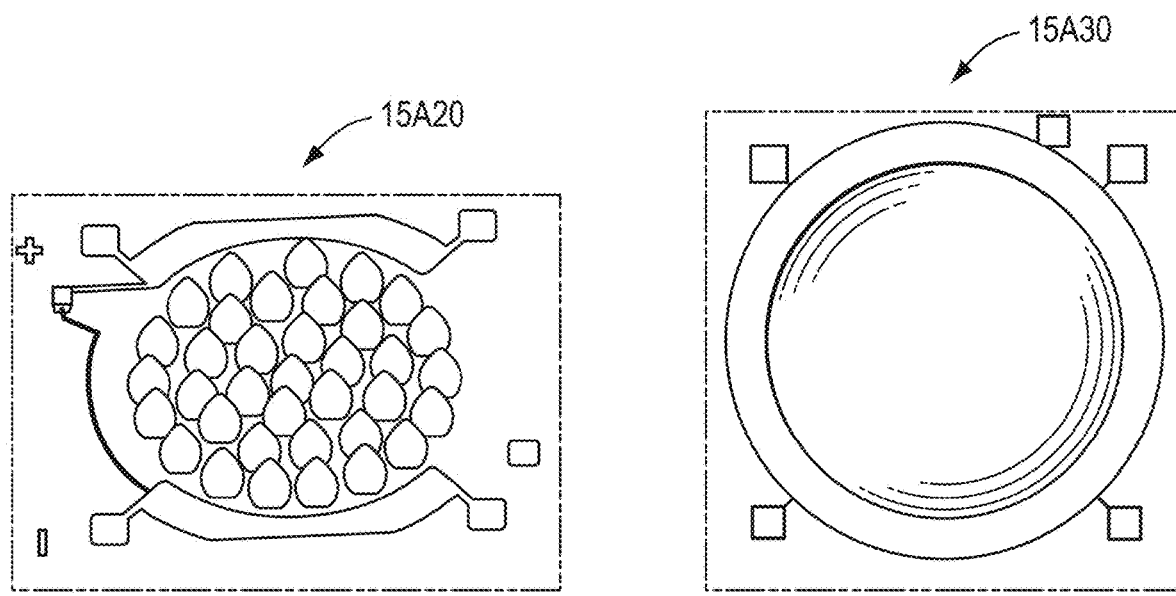
FIG. 15A2
FIG. 15A3

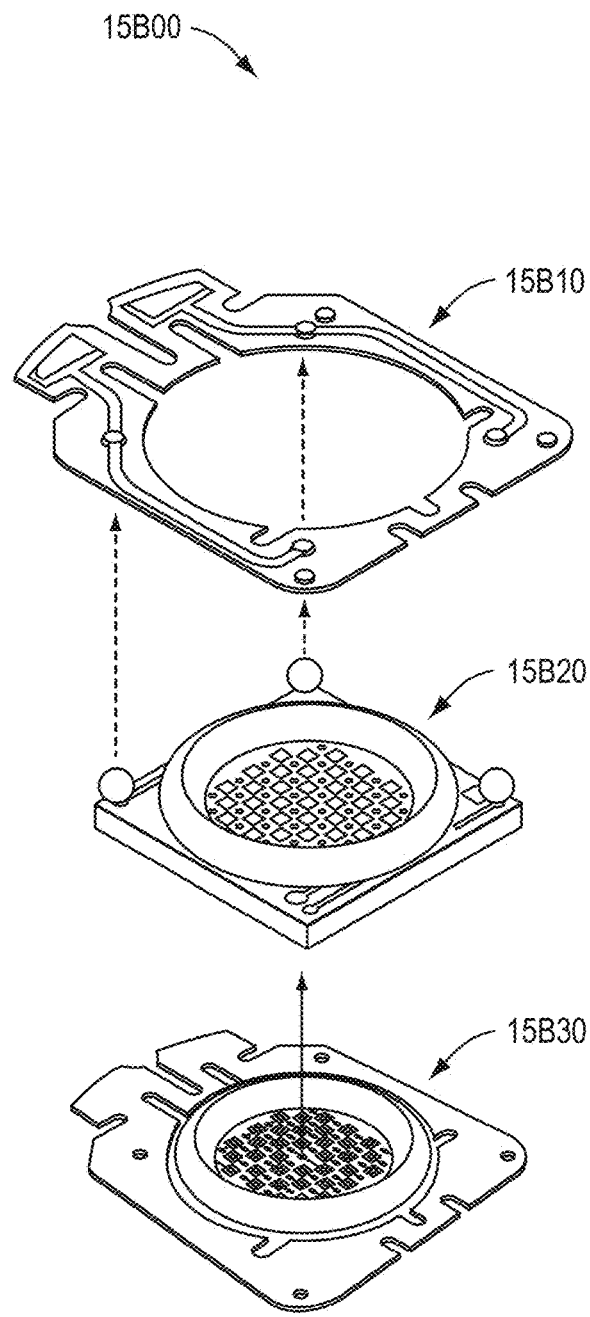
FIG. 15B1
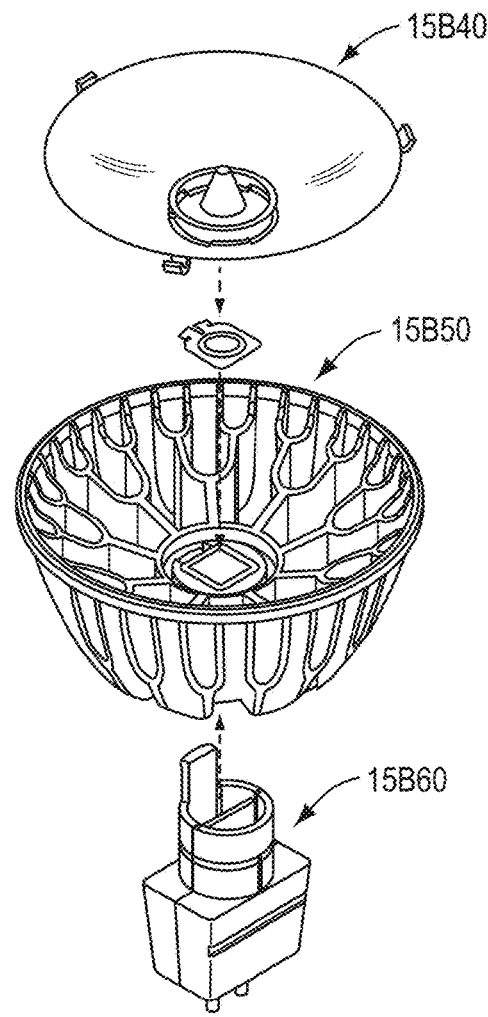
FIG. 15B2
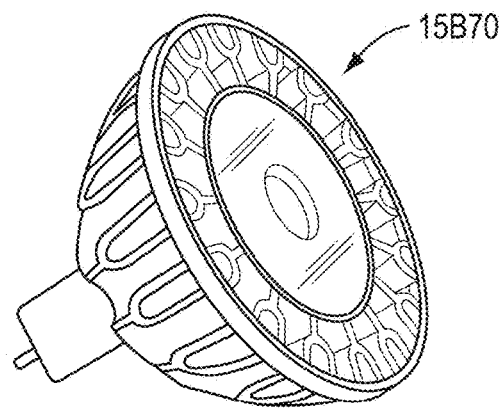
FIG. 15B3

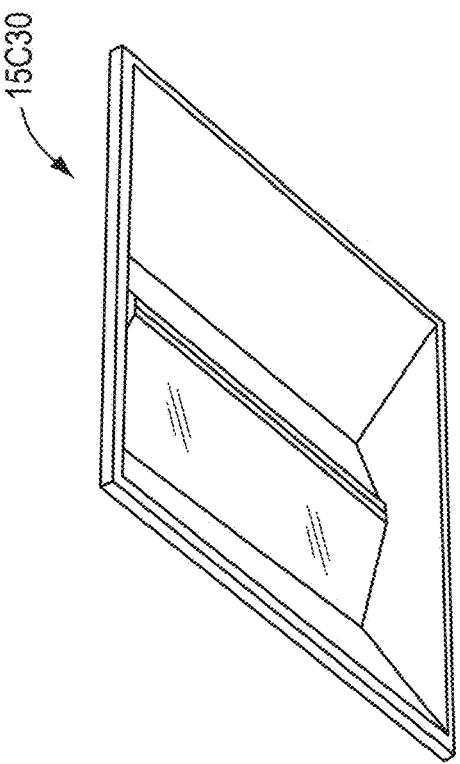
FIG. 15C3
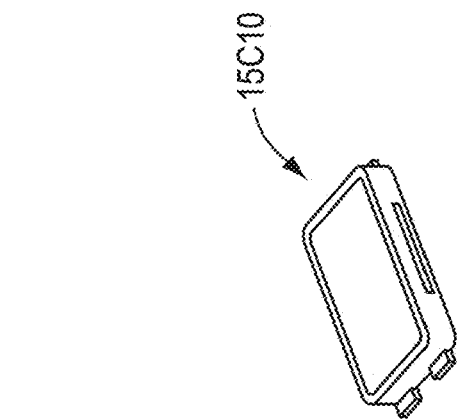
FIG. 15C1
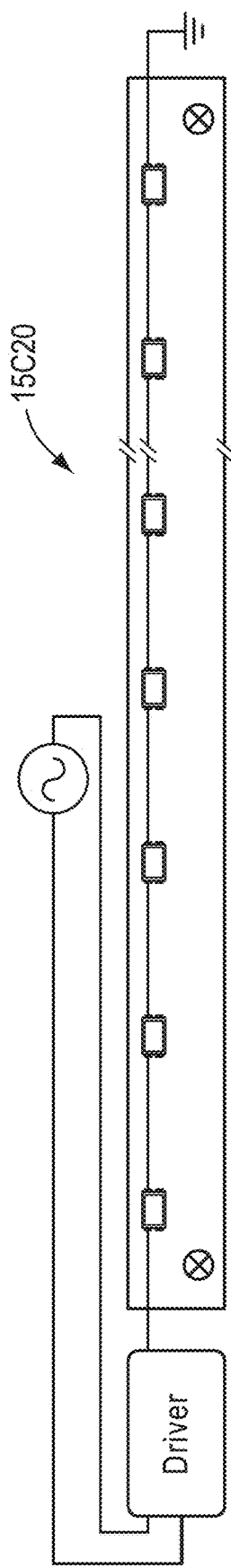
FIG. 15C2

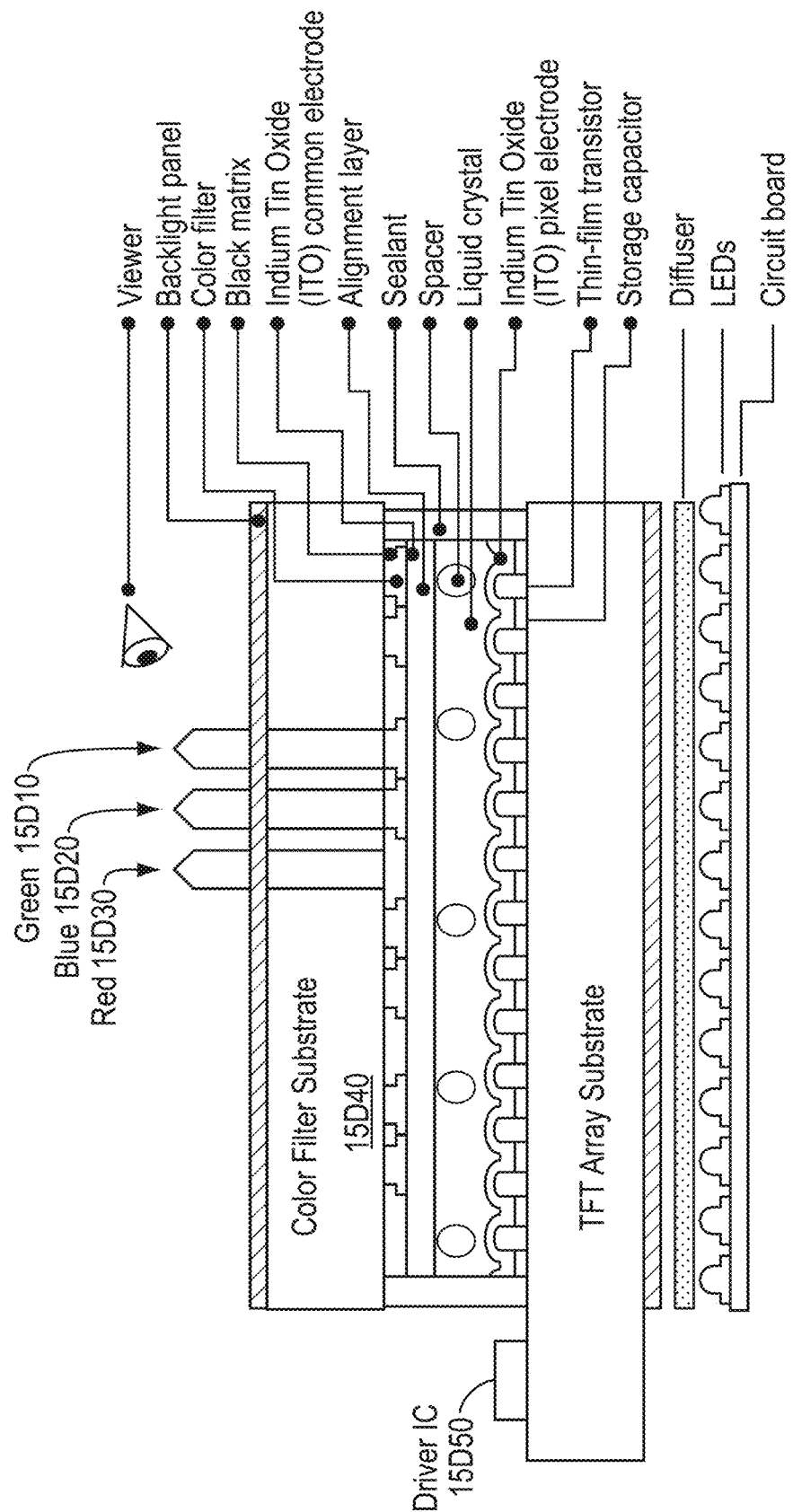
FIG. 15D1

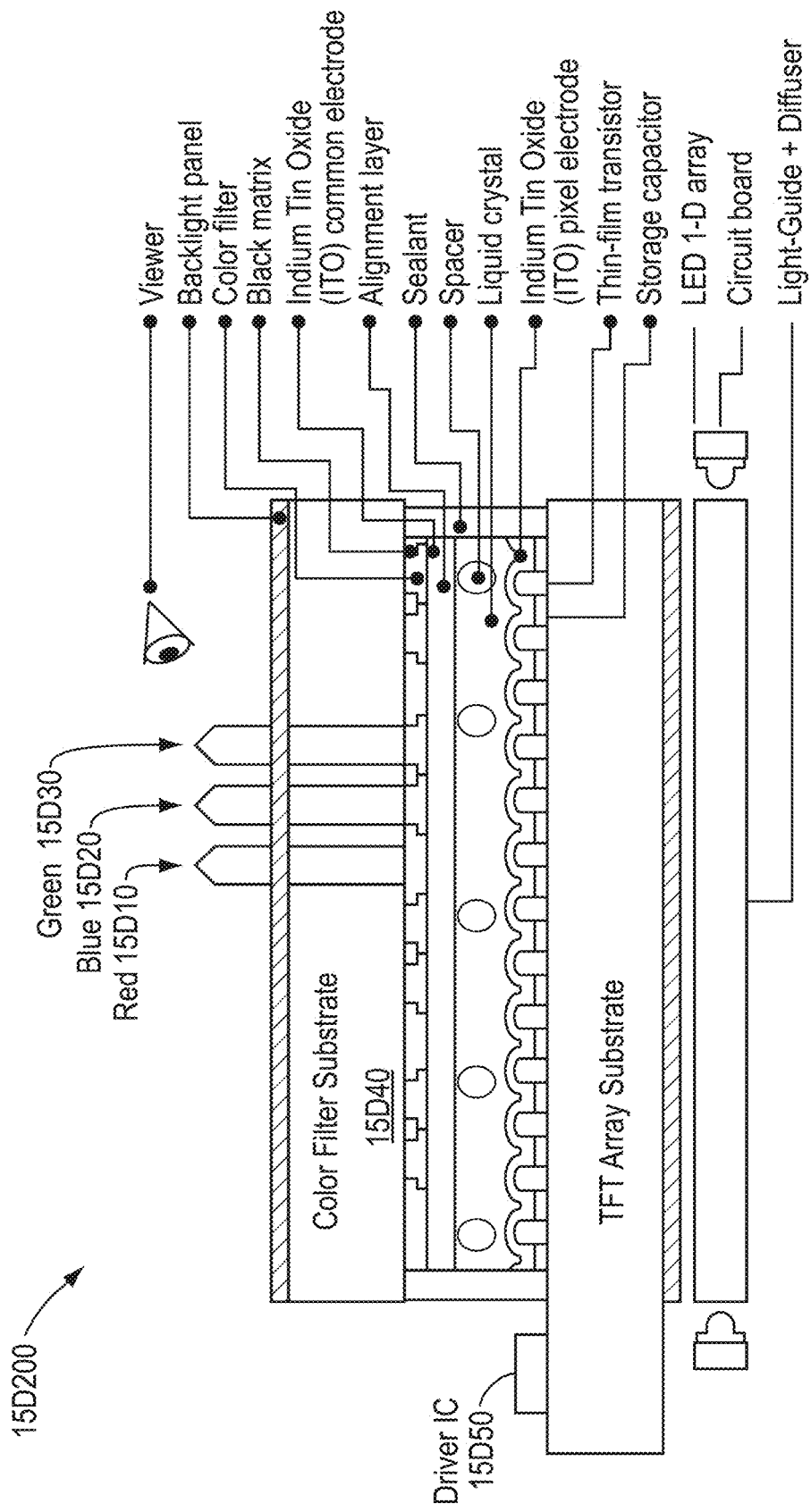
FIG. 15D2

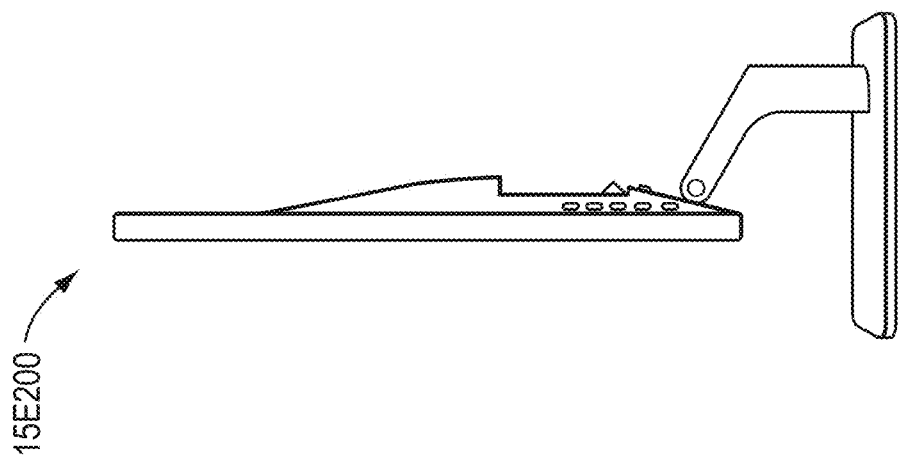
FIG. 15E2
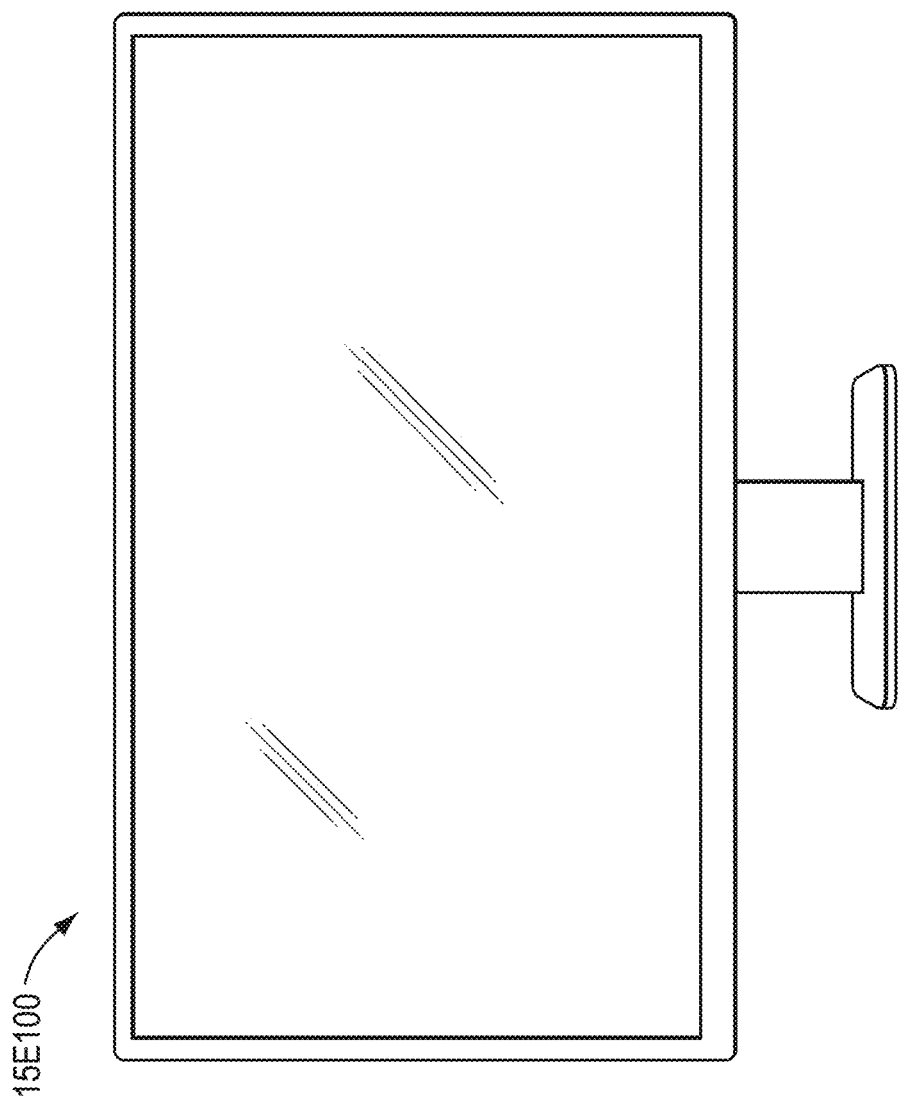
FIG. 15E1

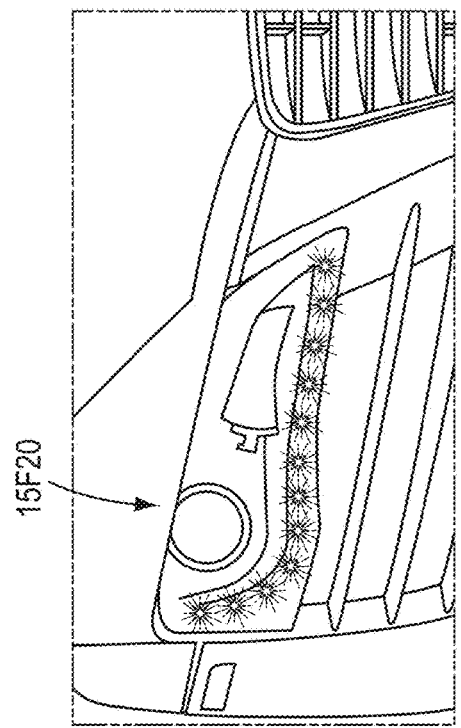
FIG. 15F2
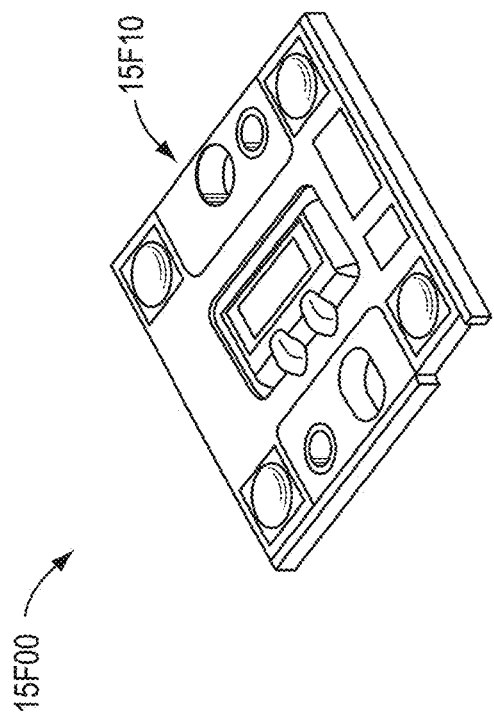
FIG. 15F1
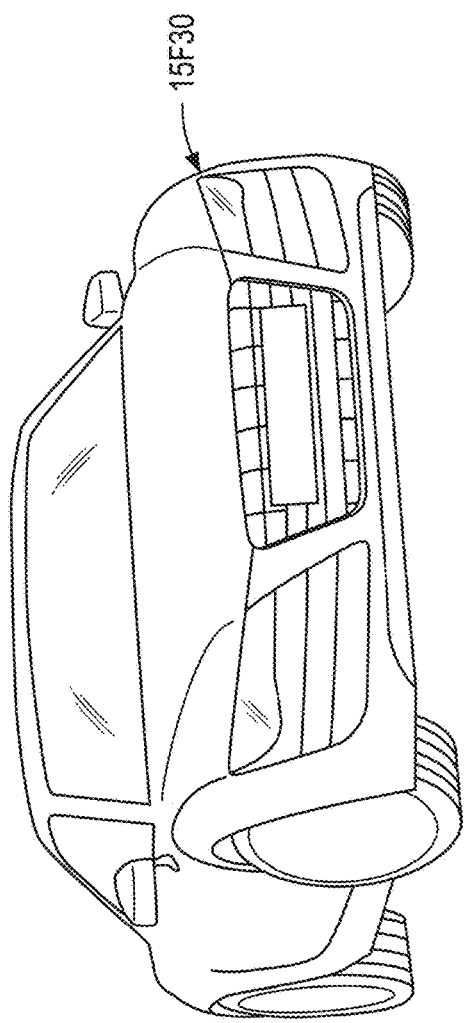
FIG. 15F3

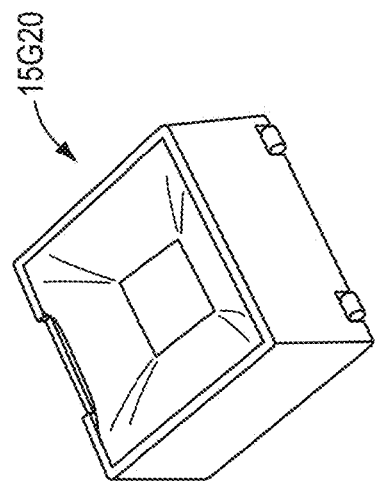
FIG. 15G2
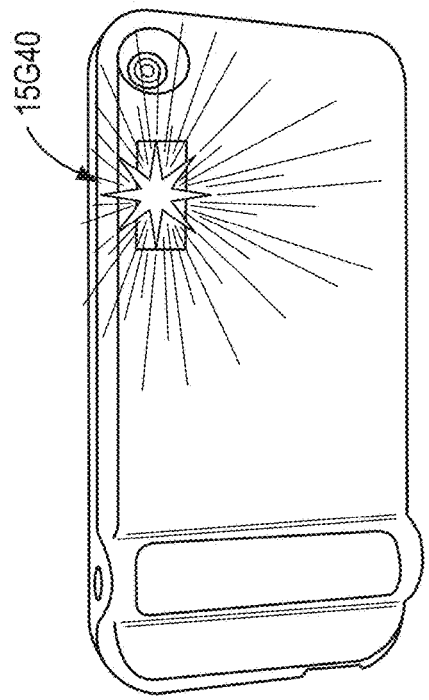
FIG. 15G4
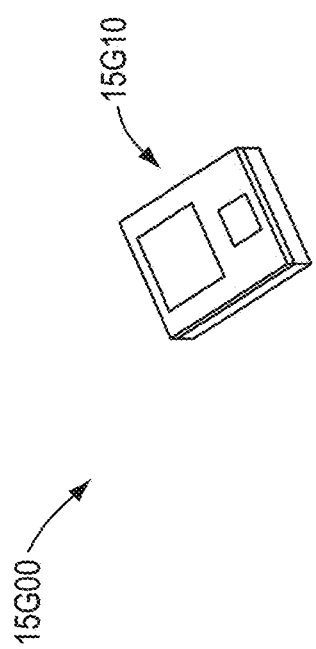
FIG. 15G1
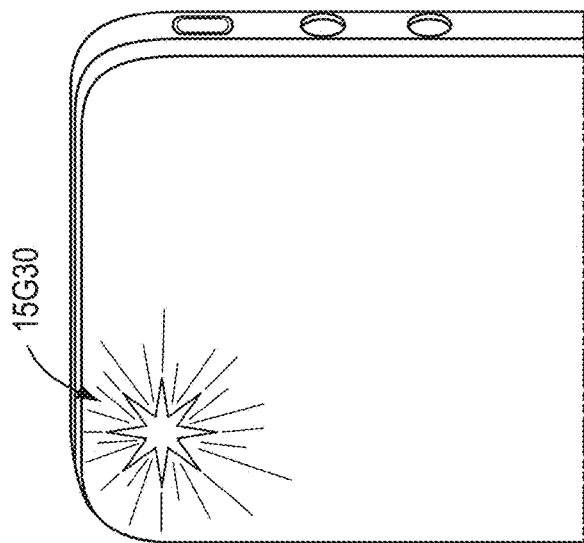
FIG. 15G3

CIRCADIAN-FRIENDLY LED LIGHT SOURCE

This application is a continuation of U.S. application Ser. No. 16/168,471, filed Oct. 23, 2018, which is a continuation of U.S. application Ser. No. 16/031,121, filed Jul. 10, 2018, now. U.S. Pat. No. 10,137,277, issued Nov. 27, 2018, which is a continuation of U.S. patent application Ser. No. 15/229,959, filed Aug. 5, 2016, now U.S. Pat. No. 10,076,633, issued Sep. 18, 2018, which is a continuation of U.S. patent application Ser. No. 14/316,685, now U.S. Pat. No. 9,410,664, issued Aug. 9, 2016. Filed Jun. 26, 2014, now U.S. Pat. No. 9,410,664, issued Aug. 9, 2016, which claims the benefit under 35 U.S.C. § 119(e) of U.S. Provisional Application No. 61/871,525 filed on Aug. 29, 2013, which is incorporated by reference in its entirety.

FIELD

The disclosure relates to the field of illumination products and more particularly to apparatus and methods for providing circadian-friendly LED light sources.

BACKGROUND

Identification of non-visual photoreceptors in the human eye (so-called intrinsically photosensitive retinal ganglion cells, or "ipRGCs") linked to the circadian system has sparked considerable interest in the effects of various light spectra on health and amenity for human beings. High circadian stimulation may lead to positive effects such as resetting sleep patterns, boosting mood, increasing alertness and cognitive performance, and alleviating seasonal affective depression. However, mis-timed circadian stimulation can also associated with disruption of the internal biological clock and melatonin suppression, and may be linked to illnesses such as cancer, heart disease, obesity and diabetes.

Circadian stimulation is associated with glucocorticoid elevation and melatonin suppression and is most sensitive to light in the blue wavelength regime. With the preponderance of light-emitting diode (LED) illumination products being based on blue-primary phosphor-converted white-emitting LEDs, the situation has developed that most LED-based illumination sources have higher levels of circadian stimulation than the traditional sources they are intended to replace.

In addition, illumination products are rarely tunable (other than mere dimming), and legacy illumination products fail to address the impact on humans with respect to diurnal or circadian cycles. Still worse, legacy illumination products that are ostensibly tunable fail to produce good color rendering throughout the tunable range.

What is needed is a technique or techniques for constructing illumination products in which light emission (e.g., LED light emission) can be controlled to provide varying levels of circadian stimulation while providing desirable light quality aspects such as correlated color temperature (CCT) and color rendering index (CRI). Also needed is an illumination system in which a first ratio and a second ratio of light emission are such that changing from the first ratio to the second ratio varies relative circadian stimulation while maintaining a CRI above 80 and maintaining the CCT within a prescribed range.

The aforementioned legacy technologies do not have the capabilities to implement a circadian-friendly LED light source in an efficient manner. Therefore, there is a need for improved approaches.

SUMMARY

Regarding human circadian system stimulation, positive benefits can be realized and the deleterious ones avoided by stimulating a circadian light cycle in a way similar to that which occurs in nature (sunlight action over the course of the day), i.e., bright illumination levels associated with high blue content in the morning and midday, and lower light levels and greatly reduced blue content in the evenings.

The embodiments disclosed herein describe how to make and use various combinations of different LED emission spectra, and how to make white light sources that can be tuned to cycle through ranges from high-circadian-stimulating light to less-circadian-stimulating light while maintaining reasonable color rendering (CRI>80 and R9>0) and white color point.

In a first aspect, light sources are provided comprising at least one first LED emission source characterized by a first emission; and at least one second LED emission source characterized by a second emission; wherein the first emission and the second emission are configured to provide a first combined emission and a second combined emission, the first combined emission is characterized by a first SPD and fractions $Fv1$ and $Fc1$; the second combined emission is characterized by a second SPD and fractions $Fv2$ and $Fc2$; $Fv1$ represents the fraction of power of the first SPD in the wavelength range from 400 nm to 440 nm; $Fc1$ represents the fraction of power of the first SPD in the wavelength range from 440 nm to 500 nm; $Fv2$ represents the fraction of power of the second SPD in the wavelength range from 400 nm to 440 nm; $Fc2$ represents the fraction of power of the second SPD in the wavelength range from 440 nm to 500 nm; the first SPD and the second SPD have a color rendering index above 80; $Fv1$ is at least 0.05; $Fc2$ is at least 0.1; and $Fc1$ is less than $Fc2$ by at least 0.02.

In a second aspect, display systems are provided comprising a first LED emission source characterized by a first emission; and a display configured to emit a first SPD characterized by a first fraction $Fv1$ of power in the range 400 nm to 435 nm; wherein, the display system is characterized by a color gamut of at least 70% of NTSC; the first SPD is substantially white with a CCT in a range from 3000K to 9000K; and $Fv1$ is at least 0.05.

In a third aspect, light sources are provided comprising an LED device configured to emit a primary emission; one or more wavelength conversion materials optically coupled to the primary emission; wherein a portion of the primary emission is absorbed by the wavelength conversion materials to produce a secondary emission; wherein a combination of the primary emission and the secondary emission produces white light characterized by an SPD having a CCT and a color rendering index; wherein at least 5% of the SPD power is in a wavelength range from 400 nm to 435 nm; wherein a circadian stimulation of the SPD is less than 80% of a circadian stimulation of a reference illuminant having the same color temperature; and wherein the white light is characterized by a color rendering index above 80.

In a fourth aspect, lighting systems are provided comprising an LED device configured to emit a primary emission characterized by a primary SPD; at least one phosphor optically coupled to the primary emission, wherein the at least one phosphor is characterized by saturable absorption within a blue-cyan wavelength region; wherein the LED device is configured to be controlled by a power signal configured to dim the primary emission; wherein at a first power level the system emits a first SPD characterized by a first fraction $fc1$ of spectral power in a wavelength range from 440 nm to 500 nm and a first CCT; wherein at a second power level the system emits a second SPD characterized by a second fraction fc2 of spectral power in a wavelength range from 440 nm to 500 nm and a second CCT; and wherein the second power level is less than the first power level and the second fraction fc2 is less than 80% of the first fraction fc1.

BRIEF DESCRIPTION OF THE DRAWINGS

Those skilled in the art will understand that the drawings, described herein, are for illustration purposes only. The drawings are not intended to limit the scope of the present disclosure.

FIG. 4C1 and FIG. 4C2 show emission of a first violet-pumped two-phosphor LED and a second violet-pumped blue-phosphor LED, respectively, according to some embodiments.

FIG. 4D1 shows the individual and combined LED-based emission spectra of FIG. 4C1 and FIG. 4C2.

FIG. 4D2 shows differences in color properties and levels of circadian stimulation, according to some embodiments.

FIG. 4E1 and FIG. 4E2 show emission of a first violet-pumped two-phosphor LED and a second blue-emitting LED, respectively, according to some embodiments.

FIG. 4F1 shows the individual and combined LED-based emission spectra of FIG. 4D1 and FIG. 4D2.

FIG. 4F2 shows differences in color properties and levels of circadian stimulation, according to some embodiments.

FIG. 4I shows SPDs for two display systems with a white screen, according to some embodiments.

FIG. 4L1 and FIG. 4L2 illustrate the situation for a typical LED-lit liquid crystal display, according to some embodiments.

FIG. 4N1 and FIG. 4N2 show situations for which the phosphor system is tuned to better work with a chosen primary peak emission wavelength, according to some embodiments.

FIG. 5C1 through FIG. 5C4 show characteristics of two sets of LEDs that are controlled independently, according to some embodiments.

FIG. 10A through FIG. 10I depict embodiments of the present disclosure in the form of lamp applications according to some embodiments.

FIG. 15A1 Through FIG. 15I depict lighting applications.

DETAILED DESCRIPTION

Reference is now made in detail to certain embodiments. The disclosed embodiments are not intended to be limiting of the claims.

Non-visual photoreceptors in the human eye (so-called intrinsically photosensitive retinal ganglion cells) are linked to the circadian system. While details of the circadian excitation band continue to evolve, a common consensus is that it the excitation band is peaked in the blue range at around 465 nm.

Figure 1A:
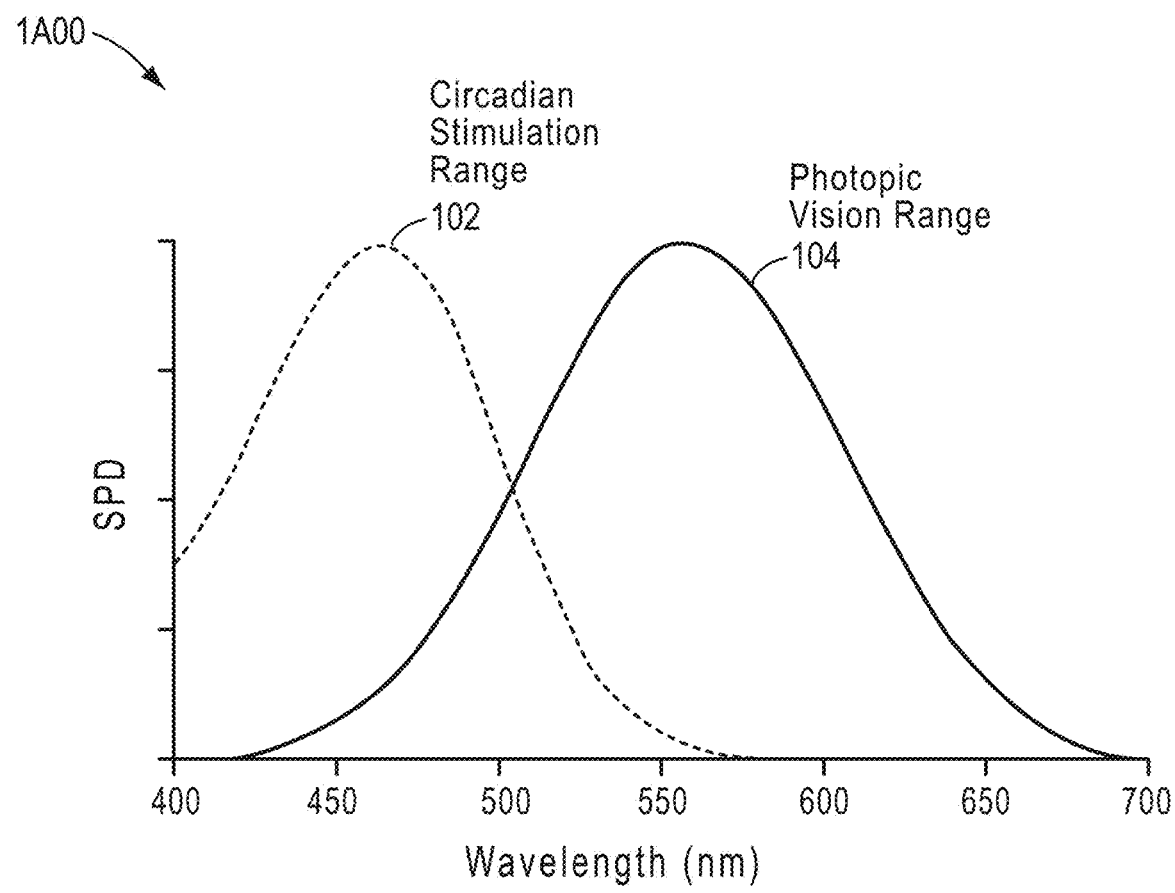
FIG. 1A is a diagram showing a circadian stimulation wavelength range as used to tune a circadian-friendly LED light source, according to some embodiments.

FIG. 1A is a diagram 1A00 showing a circadian stimulation wavelength range (CSWR) 102 as used to tune a circadian-friendly LED light source as presented by Brainard et al. in *The Journal of Neuroscience*, Aug. 15, 2001, 21(16):6405-6412 (Brainard), compared to the photopic vision range 104. With such a broad effective action spectrum, it appears there is little one can do to vary circadian stimulation for a white light source, other than varying the relative short-wavelength content, that is, the CCT. However, more recent work suggests that the relevant CSWR is in fact much narrower than presented in Brainard et al. For example, in Rahman et al., *Endocrinology*, Aug. 7, 2008, 149(12):6125-6135, it is shown that glucocorticoid elevation and melatonin suppression may be avoided by filtering blue light in a wavelength range of only 450 nm to 480 nm. This is significant because a narrower CSWR means there should be more flexibility in designing a white light source for desirable quality of light, while also controlling the amount of circadian stimulation. Further, it is noteworthy that Brainard et al. imposed a symmetric shape for their action spectrum when fitting experimental data; however, a careful analysis of the experimental points in FIG. 5 of Brainard et al. shows that the experimental response at short wavelength (e.g., 420 nm) is significantly lower than is obtained by the fitted curve. In other words, there is suggestive evidence that the CSWR is not well-known, especially at short wavelength, and may be narrower than is reported in some action spectra.

Circadian stimulation (CS) via ipRGCs for an illuminant with a spectral power distribution SPD as a function of wavelength, λ, can be modeled as:

$$CS = \frac{\int c(\lambda) SPD(\lambda) d\lambda}{\int SPD(\lambda) d\lambda}$$

where c(λ) is the circadian stimulation spectrum. For two illuminants A and B of equal luminous flux (relevant for illumination applications), the relative Circadian Stimulation (CS) of A vs. B is:

$$\frac{CS_A}{CS_B} \cdot \frac{LE_B}{LE_A}$$

where LE is the lumen equivalent of the spectral power distribution.

Figure 1B:
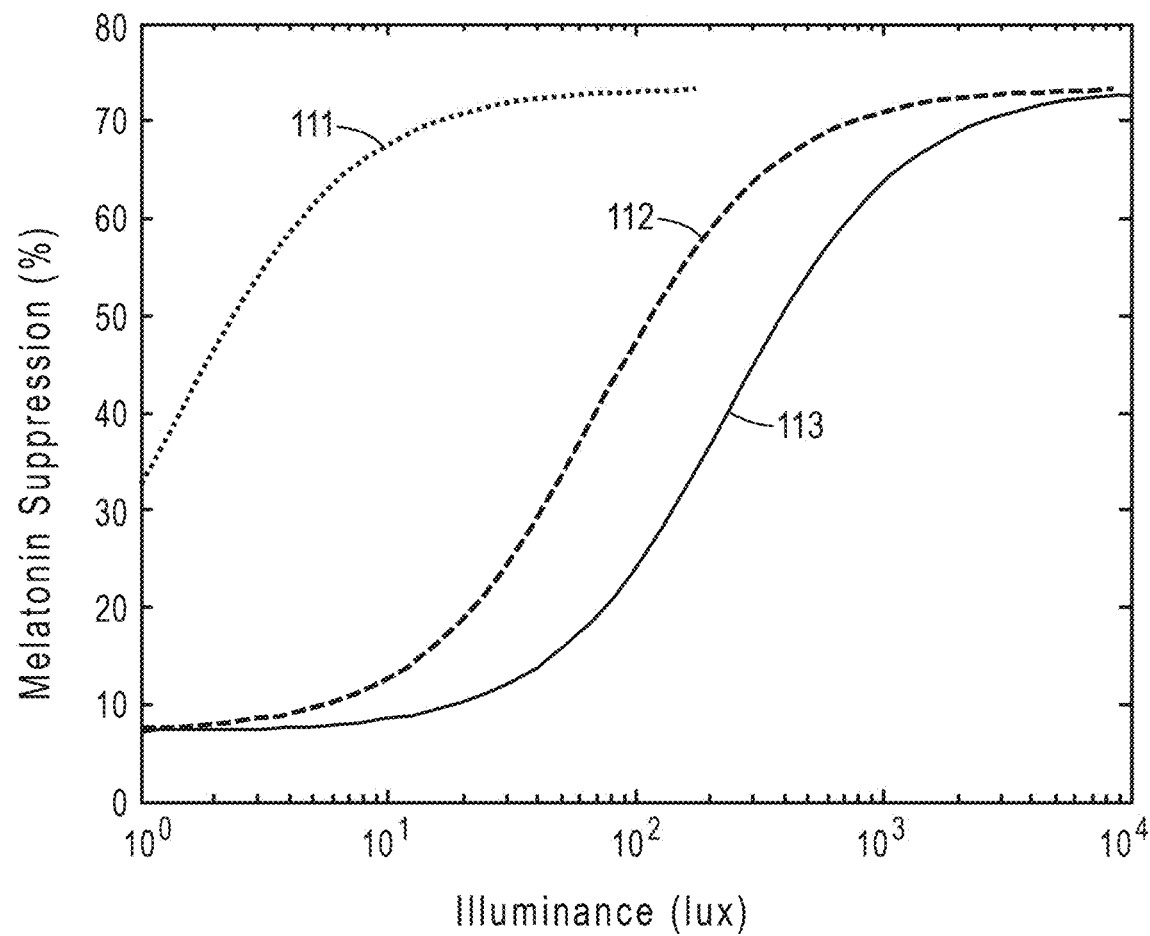
FIG. 1B shows how the impact of a light source on the circadian system scales against relative measures.

FIG. 1B shows how the impact of a light source on the circadian system scales against light intensity. The impact of a light source on the circadian system scales with relative CS, with light intensity (e.g., lux level), and with exposure time. One can combine the relative CS and the data from monochromatic stimuli disclosed by Brainard. One then obtains FIG. 1B which shows the melatonin suppression for various illuminances and for various light sources.

FIG. 1B shows melatonin suppression as a function of illuminance (lux) reaching the human eye, after a 90 min exposure. Curve 111 shows the response to monochromatic radiation at 460 nm, and is directly taken from Brainard. Curve 112 shows the response to standard illuminant D65. Curve 113 shows the response to illumination by standard illuminant A. Curves 112 and 113 are obtained by shifting curve 111, according to their relative CS.

FIG. 1B shows that for a common indoor residential lighting situation (300 1× under illuminant CIE A, representative of an incandescent lamp) melatonin suppression is significant: about 50% after 90 min. Thus, even in this common situation the circadian system can be impacted. For light sources with a larger relative CS than illuminant A, the effect can be stronger.

Figure 1C:
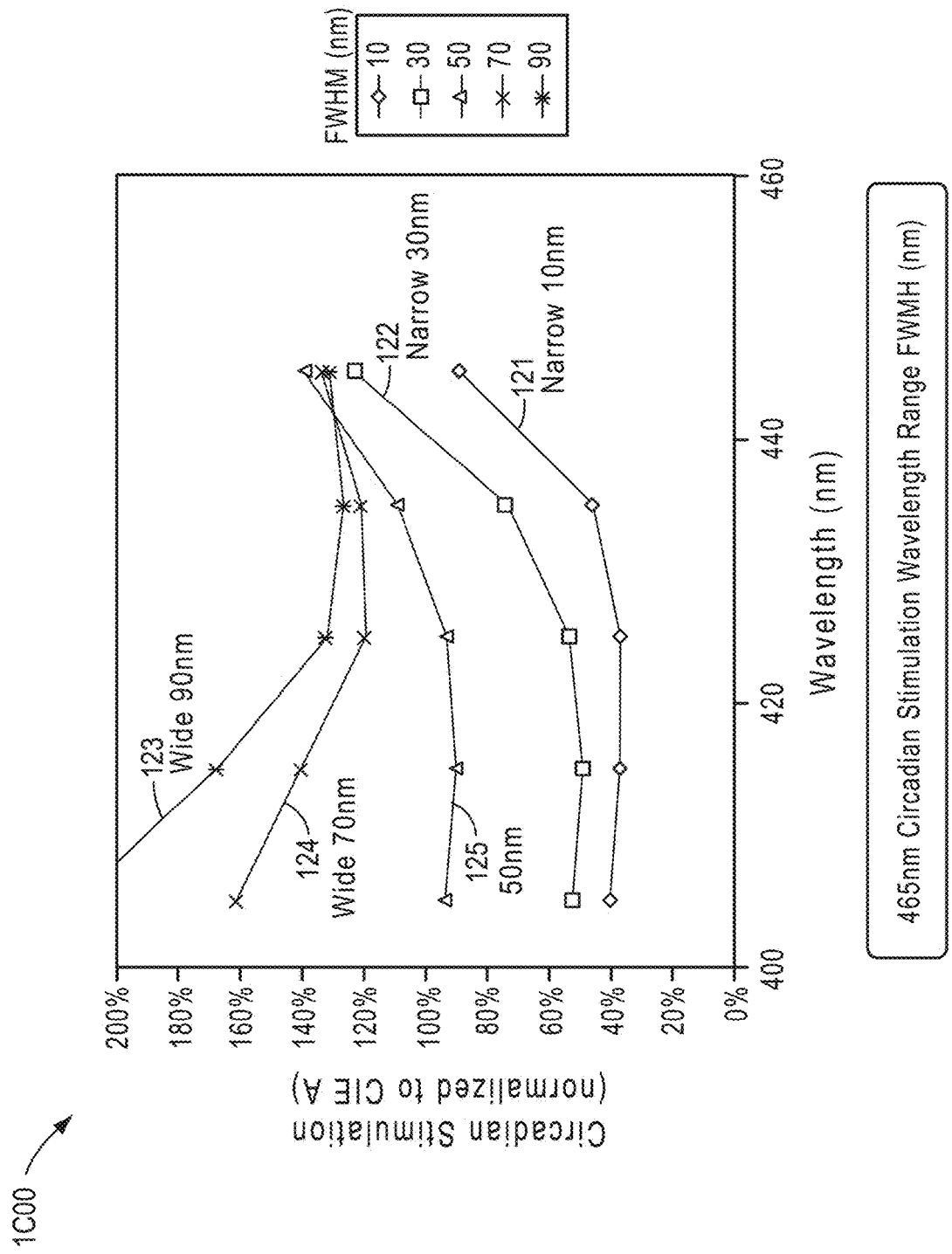
FIG. 1C shows a relative circadian stimulation for 3300K white light sources composed of a primary LED (violet- to blue-emitting) combined with a green-emitting and red-emitting phosphor for different full-width half-maxima of circadian stimulation wavelength ranges peaked at 465 nm, according to some embodiments.
Figure 1D:
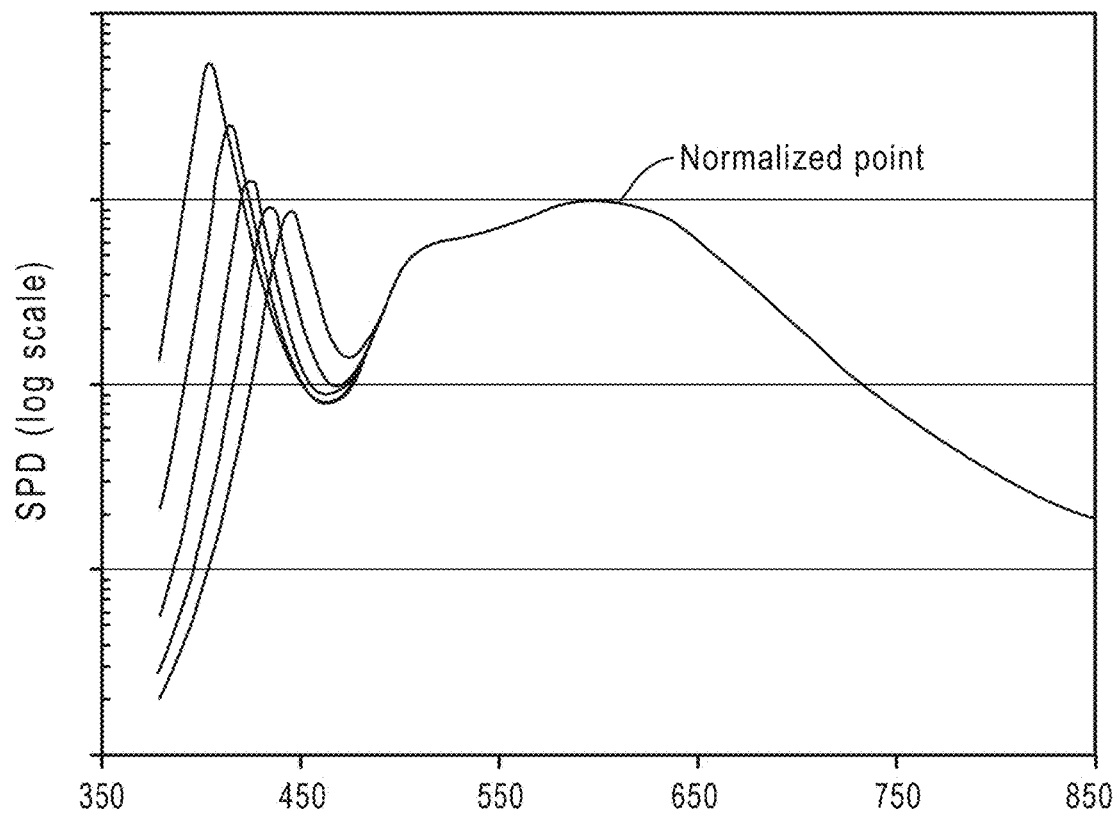
FIG. 1D shows SPDs for 3300K white light sources composed of a primary LED (violet- to blue-emitting) combined with a green-emitting and red-emitting phosphor, normalized to emission at 600 nm according to some embodiments.

The following figures and text serve to compare the relative CS between various LED white light sources. FIG. 1C shows a relative circadian stimulation (CS) for 3300K white light sources composed of a primary LED (varying from violet- to blue-emitting) combined with a green-emitting and a red-emitting phosphor. In FIG. 1C, the x-axis is the center emission wavelength of the primary LED and the y-axis is the relative circadian stimulation (normalized to CIE A). The circadian stimulation is calculated assuming a circadian stimulation wavelength range peaked at 465 nm, with a Gaussian line shape and with various full-width half-maxima (from 10 nm to 90 nm) as labeled on the figure (see FIG. 1A). Regarding the phosphors used to obtain the white light source, suitable phosphors may be $Eu^{2+}$ doped materials. An example of a green-emitter is $BaSrSiO:Eu^{2+}$. An example of a red-emitter is $CaAlSiN:Eu^{2+}$. In FIG. 1C, the green and red emission peak wavelength/FWHM are 530/100 and 630/100, respectively. Other phosphors are also possible, as described below. In addition to phosphors, other wavelength down-converting materials may be used, such as organic materials or semiconductors such as nanoparticles otherwise known as "quantum dots". In other embodiments, the green and/or red emission may be provided by LEDs. As shown in FIG. 1C, for wide CSWRs (e.g., wide 90 nm 123 and wide 70 nm 124) there is little primary LED wavelength sensitivity, or even a penalty as the wavelength gets too short. However, for narrower CWSRs (e.g., 10 nm 121 and 30 nm 122), there is a strong benefit to reducing the primary LED wavelength. For example, for a 30 nm FWHM CSWR 122, the relative CS for a violet (~405 nm to 425 nm) primary 3300K LED is about half that of the CIE A illuminant (2856K) 125. Thus, light source 122 is less circadian stimulating than many incandescent lamps, and dramatically less stimulating than a 445 nm (blue) based 3300K LED 123, which has a CS about 20% higher than CIE A. SPDs for various LED light source emissions including those of FIG. 1C are shown in FIG. 1D, normalized to emission at 600 nm. The SPDs are characterized, for example, by different violet content. For each SPD, CRI is maintained at 80 or higher and R9 is above zero (about 10).

Figure 1E:
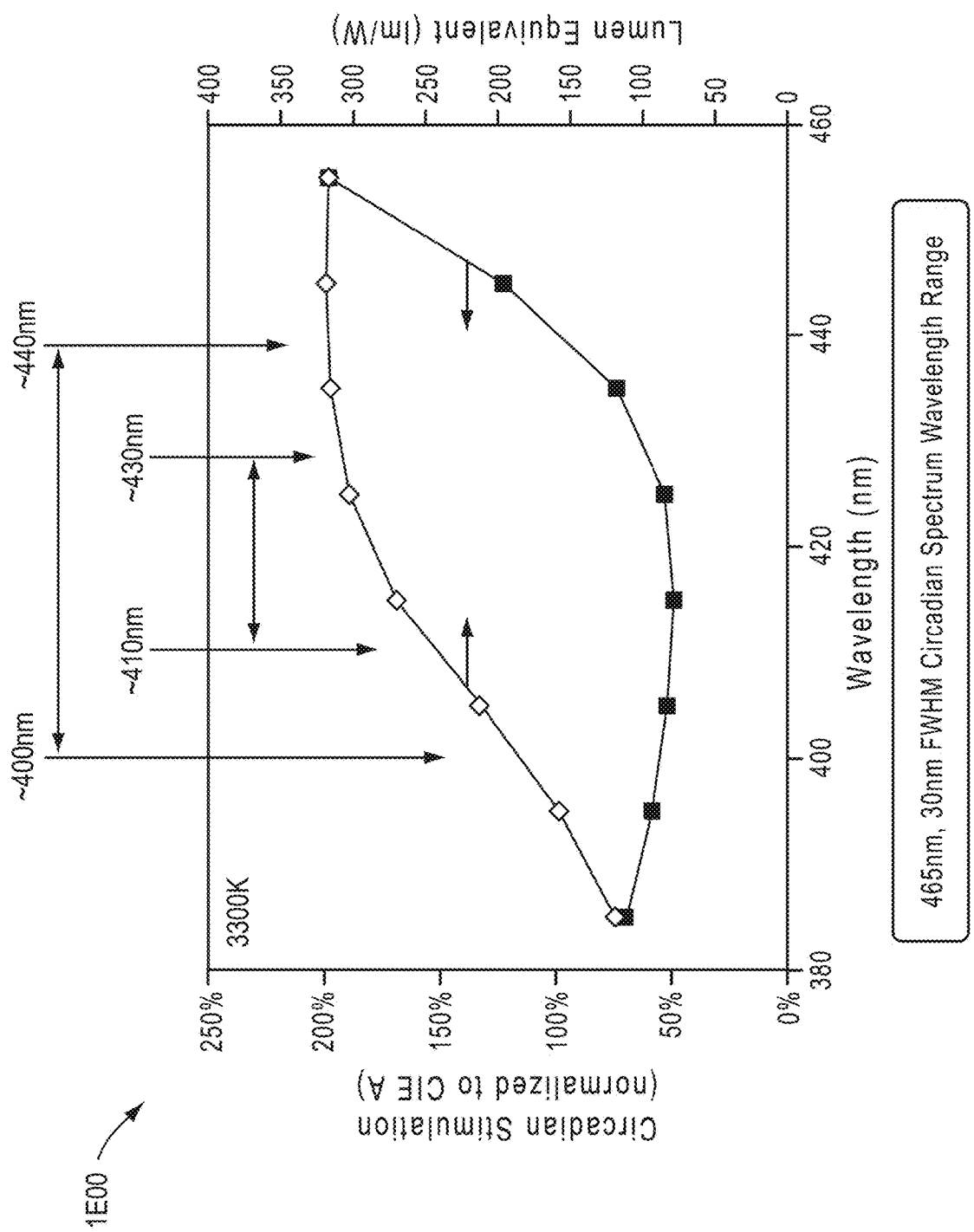
FIG. 1E shows the circadian stimulation for a two-phosphor based LED white light source at 3300K as a function of the primary LED emission peak wavelength, according to some embodiments.

Non- or weakly-circadian-stimulating light sources are desirable, for example, for evening illumination, in order to avoid glucocorticoid elevation and melatonin suppression, and thus prepare people for healthy sleep. Referring to the 30 nm FWHM CSWR of FIG. 1C, FIG. 1E shows the CS for a two-phosphor based LED white light source at 3300K as a function of the primary LED emission peak wavelength. For a 455 nm primary emission, the lumen equivalent of the SPD is high (about 320 lm/Wopt), but the CS is also high (about twice that of CIE A). As the primary LED peak wavelength is reduced below 455 nm, the CS falls dramatically. Further, as the primary LED peak wavelength is reduced below 420 nm, the LE also decreases. Thus, there is a range of primary LED peak emission wavelengths where the LE is still reasonably high, but the CS is reduced relative to CIE A. In particular, the wavelength range of 405 nm to 435 nm provides reduced CS and reasonable LE. A variety of standard LED sources with this CCT have a LE of about 300, therefore embodiments with an LE of about 200 or about 250 can be considered acceptable as they provide a much lower CS than standard sources.

Figure 1F:
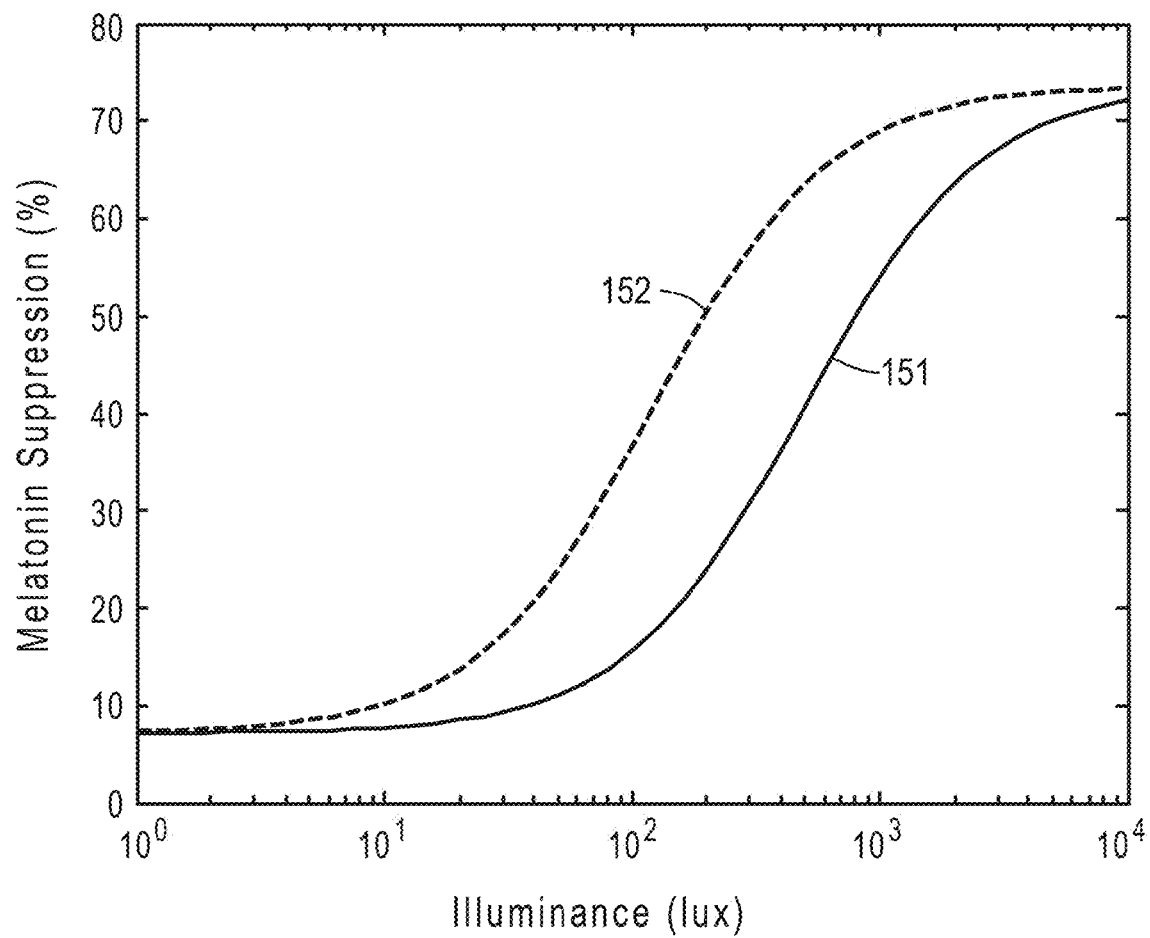
FIG. 1F shows predicted melatonin suppression versus illuminance at the eye level, for a 90 min exposure, according to some embodiments.

FIG. 1F further illustrates the advantage of such light sources. FIG. 1F shows predicted melatonin suppression versus illuminance at the eye level, for a 90 min exposure. Curve 1 corresponds to an LED source with 415 nm primary peak emission, and curve 2 corresponds to an LED source with 455 nm primary peak emission. Due to the lower relative CS, the 415 nm-primary LED induces less melatonin suppression. If the light level is dimmed to about 100 lux, the suppression becomes very small (less than 10% above the ceiling of the signal) whereas for the same illuminance under the 455 nm-primary LED, melatonin suppression is significant (about 40% in 90 min). Thus, the change in circadian stimulation has a relevant impact in a realistic environment.

In principle, another approach can be used to reduce the circadian stimulation of a light source: tuning the CCT of the light source—indeed, a warmer CCT generally leads to a lower relative CS. Various LED-based products provide this capability. However these products employ blue primary LEDs (peak emission wavelength range from about 445 nm to 460 nm). Therefore, even at low CCT, the relative CS remains fairly high (e.g., about twice that of illuminant CIE A for a 3000K LED source, as shown, for example, in FIG. 1C).

Therefore, careful choice of the emission wavelength of the primary LED and of the overall emission spectrum of the primary LED is important to significantly modulate CS.

Embodiments of various circadian-friendly LED white light sources can be configured such that the respective emission spectra can be tuned so as to simulate a circadian cycle in a more or less daily diurnal cycle.

Figure 2A:
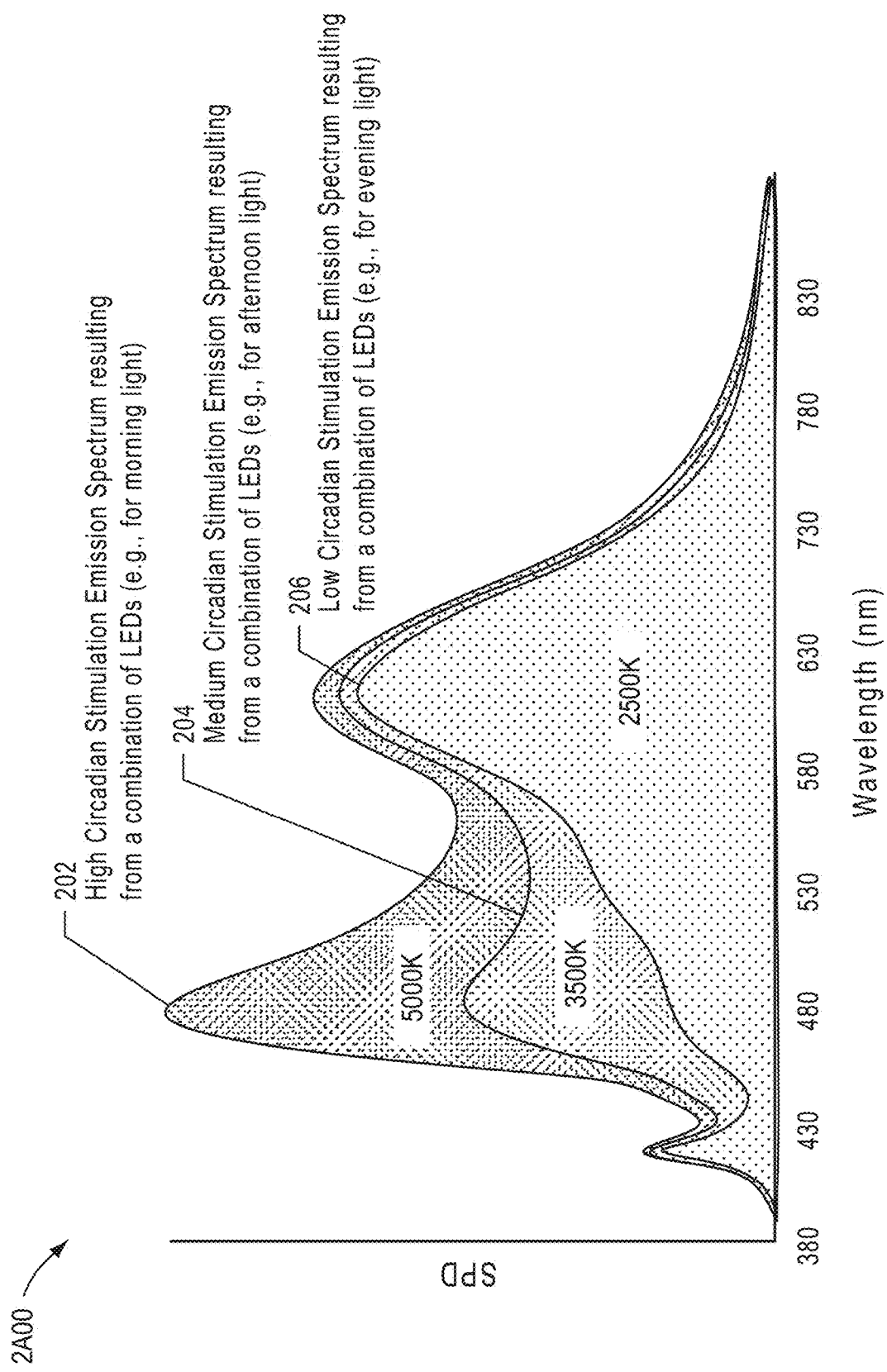
FIG. 2A shows LED spectral power distributions (SPDs) of wavelength combinations as used in configuring a circadian-friendly LED light source, according to some embodiments.

FIG. 2A shows spectral power distributions (SPDs) of various wavelength combinations 2A00 as used in configuring a circadian-friendly LED white light source.

As shown in FIG. 2A, a stimulating blue peak is emitted for morning circadian stimulation (see curve 202). Another curve exhibits low circadian stimulation (see curve 206) for evenings, and a third curve (204) shows an intermediate option.

Figure 2B:
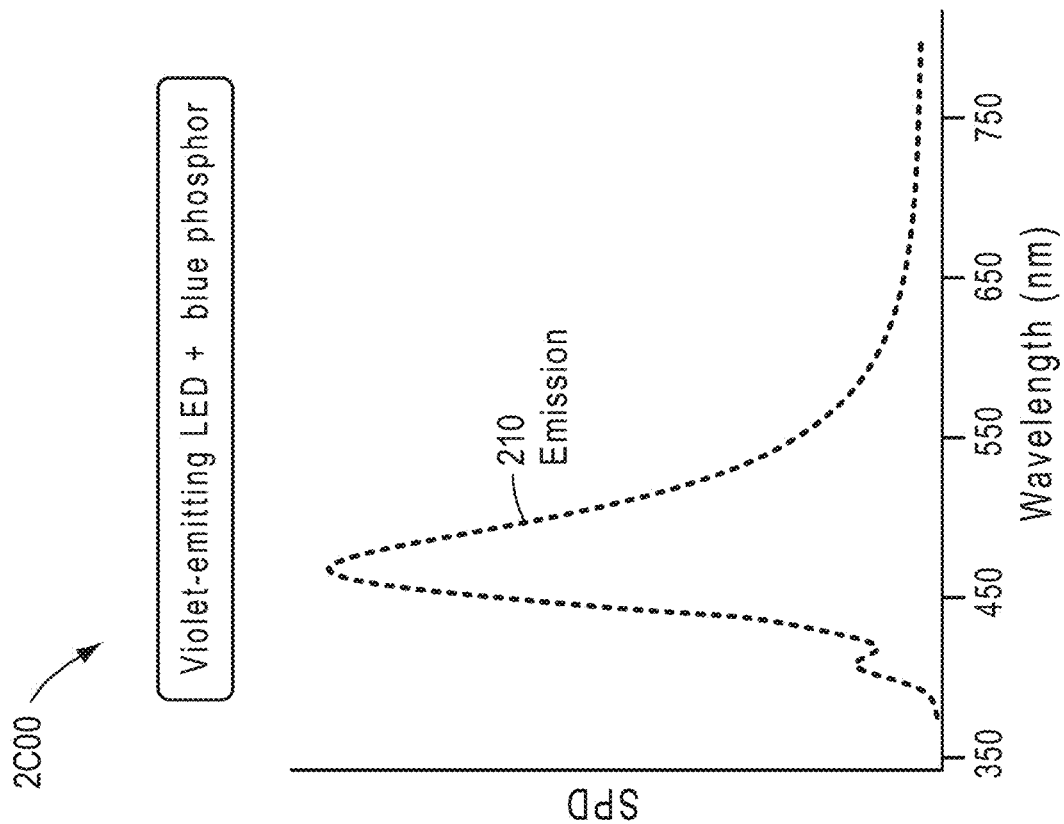
FIG. 2B shows an SPD corresponding to a first LED emission as used in configuring a circadian-friendly LED light source, according to some embodiments.

In certain embodiments, a circadian-friendly LED white light source (e.g., see luminaire of FIG. 4A and lamp of 6A and FIG. 6B) includes a first LED (see FIG. 2B) such as a violet (or UV) primary LED combined with a green, red, and (optional) blue phosphor to emit a spectrum 208 that is substantially a low-circadian-stimulating spectrum at a correlated color temperature (CCT) of 2500K (see spectrum of LED emissions 208 in FIG. 2B). Such an LED and phosphor combination can exhibit a reasonable white color point and can exhibit reasonable color rendering properties. Depending on the details such as the emission spectra of the primary LED and phosphors, it may not be necessary to combine a blue phosphor with a first LED.

Figure 2C:
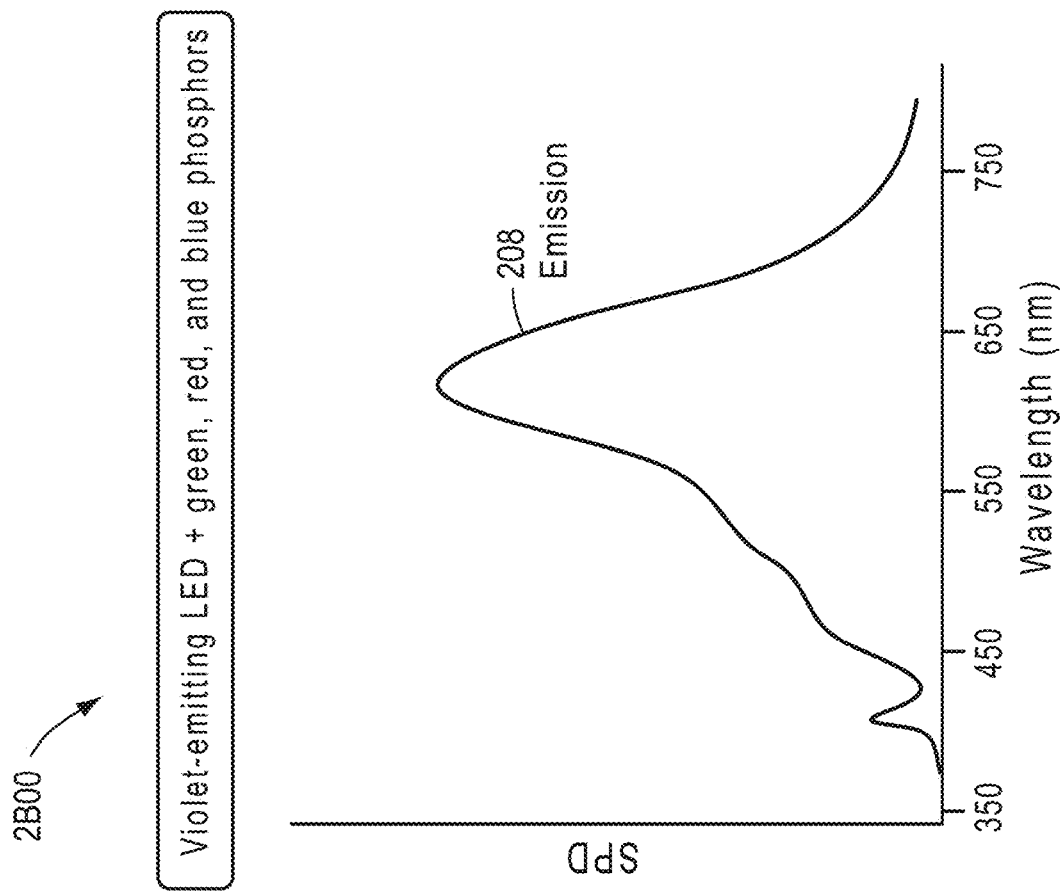
FIG. 2C shows an SPD corresponding to a second LED emission as used in configuring a circadian-friendly LED light source, according to some embodiments.

For implementation of a circadian-friendly LED light source, a second LED (see FIG. 2C) can be added. The emission 210 (FIG. 2C) can be generated by using a second LED comprising, for example, a violet (or UV) LED to pump only a blue phosphor. The blue phosphor can be selected based on absorption characteristics of photons from the primary (violet or UV) LED: namely, is the blue phosphor can be chosen such that excitation can occur for moderate phosphor loading, such that the resulting system package efficiency is sufficient. Also, a blue phosphor can be selected based on the emission properties of the combination so as to combine with the first LED emission, thus shifting or tuning the chromaticity in a controlled manner (e.g., in a direction similar to increasing CCTs along the Planckian curve to maintain a white light appearance). In addition, a blue phosphor peak emission wavelength and FWHM can be selected to maintain specified color rendering properties even as the contribution of the second LED to the total spectrum (first and second LED combined) is increased (FIG. 2A). In some cases, the desired color rendering properties can be expressed as a CRI above 50, a CRI above 80, or in certain embodiments, a CRI above 90. Other metrics such as R9, another color fidelity metric, and/or a color gamut metric can also be employed. In some embodiments, a blue phosphor may be a mix of different phosphors, which, combined together, give the desired excitation and emission properties including the desired dominant wavelength of emission for spectral tuning as described herein.

For an SPD with a CCT of 2500K, the fraction of power in the spectral range from 400 nm to 440 nm is 0.03 and the fraction of power in the range from 440 nm to 500 nm is 0.06. For an SPD with a CCT of 5000K, the fraction of power in the spectral range from 400 nm to 440 nm is 0.02 and the fraction of power in the range from 440 nm to 500 nm is 0.20.

Figure 3B:
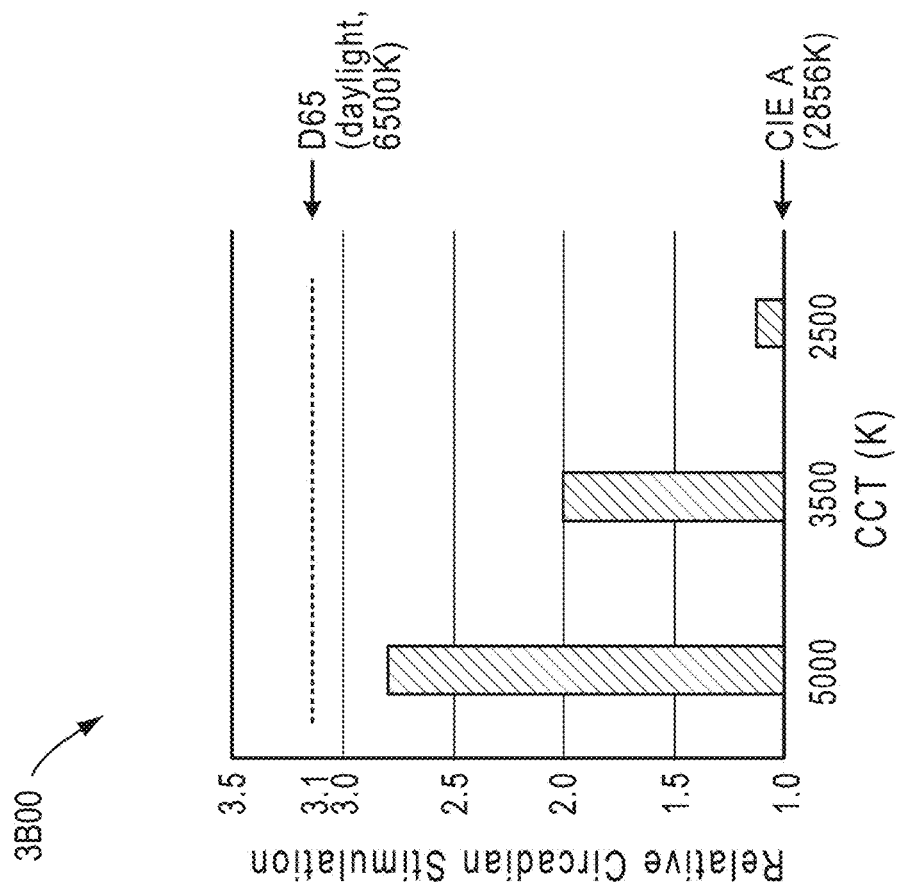
FIG. 3B is a chart showing relative circadian stimulation resulting from a circadian-friendly LED light source at three different color temperatures, according to some embodiments.
Figure 3A:
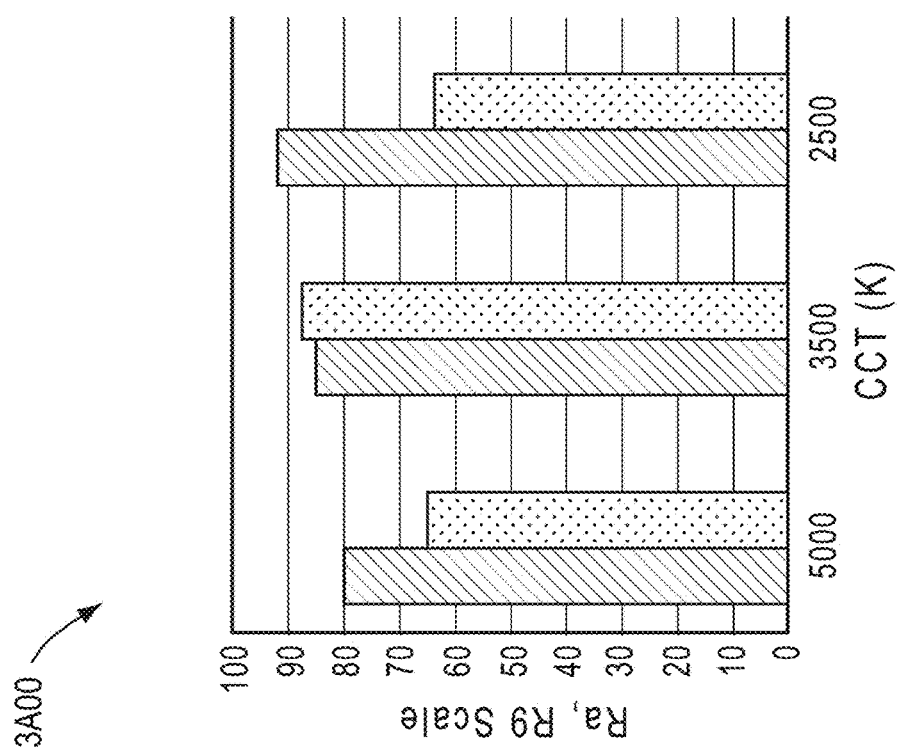
FIG. 3A is a chart showing color rendering properties exhibited by a circadian-friendly LED light source at three different color temperatures, according to some embodiments.

Certain color rendering properties for LED white light sources provided by the present disclosure at various LED temperatures are illustrated in FIG. 3A. The circadian stimulation (relative to a CIE A illuminant), based on a CSWR modeled after Brainard (102 in FIG. 1A, about 95 nm FWHM) is illustrated in FIG. 3B.

Certain embodiments use a blue phosphor characterized by a 477 nm peak emission wavelength and a FWHM of 80 nm. Such blue phosphors with a 477 nm peak emission wavelength represents only one embodiment and other embodiments use other phosphors and phosphor combinations. In particular, the phosphors and/or compositions of wavelength-conversion materials referred to in the present disclosure may comprise various wavelength-conversion materials.

Wavelength conversion materials can be ceramic or semiconductor particle phosphors, ceramic or semiconductor plate phosphors, organic or inorganic downconverters, upconverters (anti-stokes), nano-particles, combinations of any of the foregoing and other materials which provide wavelength conversion. Some examples are listed below:

$(Sr_n,Ca_{1-n})10(PO_4)_6.B_2O_3:Eu^{2+}$ (where $0 \leq n \leq 1$)
$(Ba,Sr,Ca)_5(PO_4)_3(Cl,F,Br,OH):Eu^{2+},Mn^{2+}$ $(Ba,Sr,Ca)BPO_5:Eu^{2+},Mn^{2+}$
$Sr_2Si_3O_{8}·2SrCl_2:Eu^{2+}$
$(Ca,Sr,Ba)_3MgSi_2O_8:Eu^{2+}, Mn^{2+}$
$BaAl_8O_{13}:Eu^{2+}$
$2SrO·_{0.84}P_2O_5·_{0.16}B_2O_3:Eu^{2+}$
$(Ba,Sr,Ca)MgAl_{10}O_{17}:Eu^{2+},Mn^{2+}$
$K_2SiF_6:Mn^{4+}$
$(Ba,Sr,Ca)Al_2O_4:Eu^{2+}$
$(Y,Gd,Lu,Sc,La)BO_3:Ce^{3+},Tb^{3+}$
$(Ba,Sr,Ca)_2(Mg,Zn)Si_2O_7:Eu^{2+}$
$(Mg,Ca,Sr, Ba,Zn)_2Si_{1-x}O_{4-2x}:Eu^{2+}$ (where $0 \leq x \leq 0.2$)
$(Ca,Sr,Ba)MgSi_2O_6:Eu^{2+}$
$(Sr,Ca,Ba)(Al,Ga)_2S_4:Eu^{2+}$
$(Ca,Sr)_8(Mg,Zn)(SiO_4)_4Cl_2:Eu^{2+},Mn^{2+}$
$Na_2Gd_2B_2O_7:Ce^{3+},Tb^{3+}$
$(Sr,Ca,Ba,Mg,Zn)_2P_2O_7:Eu^{2+}Mn^{2+}$
$(Gd,Y,Lu,La)_2O_3:Eu^{3+},Bi^{3+}$
$(Gd,Y,Lu,La)_2O_2S:Eu^{3+},Bi^{3+}$
$(Gd,Y,Lu,La)VO_4:Eu^{3+},Bi^{3+}$
$(Ca,Sr)S:Eu^{2+},Ce^{3+}$
$(Y,Gd,Tb,La,Sm,Pr,Lu)_3(Sc,Al,Ga)_{5-n}O_{12-3/2n}:Ce^{3+}$
 (where $0 \leq n \leq 0.5$)
$ZnS:Cu^+,Cl^-$
$(Y,Lu,Th)_3Al_5O_{12}:Ce^{3+}$
$ZnS:Cu^+,Al^{3+}$
$ZnS:Ag^+,Al^{3+}$
$ZnS:Ag^+,Cl^-$
The group:
$Ca_{1-x}Al_{x-xy}Si_{1-x+xy}yN_{2-x-xy}C_{xy}:A$
$Ca_{1-x-z}Na_zM(III)_{x-xy-z}Si_{1-x+xy+z}N_{2-x-xy}C_{xy}:A$
$M(II)_{1-x-z}M(I)_zM(III)_{x-xy-z}Si_{1-x+xy+z}N_{2-x-xy}C_{xy}:A$
$M(II)_{1-x-z}M(I)_zM(III)_{x-xy-z}Si_{1-x+xy+z}N_{2-x-Xy-2w/3}C_{xy}O_{w-v/2}H_v:A$
$M(II)_{1-x-z}M(I)_zM(III)_{x-xy-z}Si_{1-x+xy+z}N_{2-x-xy-2w/3-v/3}C_{xy}O_wH_v:A$
wherein $0<x<1$, $0<y<1$, $0 \leq z<1$, $0 \leq v<1$, $0<w<1$, $x+z<1$, $x>xy+z$, and $0<x-xy-z<1$, M(II) is at least one divalent cation, M(I) is at least one monovalent cation, M(III) is at least one trivalent cation, H is at least one monovalent anion, and A is a luminescence activator doped in the crystal structure.
$LaAl(Si_{6-z}Al_z)(N_{10-z}Oz):Ce^{3+}$ (where $z=1$)
$(Ca,Sr)Ga_2S_4:Eu^{2+}$
$AlN:Eu^{2+}$
$SrY_2S_4:Eu^{2+}$
$CaLa_2S_4:Ce^{3+}$
$(Ba,Sr,Ca)MgP_2O_7:Eu^{2+},Mn^{2+}$
$(Y,Lu)_2WO_6:Eu^{3+},Mo^{6+}$
$CaWO_4$
$(Y,Gd,La)_2O_2S:Eu^{3+}$
$(Y,Gd,La)_2O_3:Eu^{3+}$
$(Ba,Sr,Ca)_nSi_nNn:Eu^{2+}$ (where $2n+4=3n$)
$Ca_3(SiO_4)Cl_2:Eu^{2+}$
$(Y,Lu,Gd)_{2-n}Ca_nSi_4N_{6+n}C_{1-n}:Ce^{3+}$ (where $0 \leq n \leq 0.5$)
(Lu,Ca,Li,Mg,Y) alpha-SiAlON doped with $Eu^{2+}$ and/or $Ce^{3+}$
$(Ca,Sr,Ba)SiO_2N_2:Eu^{2+},Ce^{3+}$
$Ba_3MgSi_2O_8:Eu^{2+},Mn^{2+}$
$(Sr,Ca)AlSiN_3:Eu^{2+}$
$CaAlSi(ON)_3:Eu^{2+}$
$Ba_3MgSi_2O_8:Eu^{2+}$
$LaSi_3N_5:Ce^{3+}$
$Sr_{10}(PO_4)_6Cl_2:Eu^{2+}$
$(BaSi)O_{12}N_2:Eu^{2+}$
$M(II)_aSi_bO_cNdCe:A$ where $6<a<8$, $8<b<14, 13<c<17$, $5<d<9$, $0<e<2$ and M(II) is a divalent cation of (Be, Mg,Ca,Sr,Ba,Cu,Co,Ni,Pd,Tm,Cd) and A of (Ce,Pr,Nd, Sm,Eu,Gd, Tb,Dy,Ho,Er, Tm,Yb,Lu,Mn,Bi, Sb)
$SrSi_2(O,Cl)_2N_2:Eu^{2+}$
$SrSi_9Al_{19}ON_{31}:Eu^{2+}$
$(Ba,Sr)Si_2(O,Cl)_2N_2:Eu^{2+}$
$LiM_2O_8:Eu^{3+}$ where M=W or Mo For purposes of the application, it is understood that when a phosphor has two or more dopant ions (e.g., those ions following the colon in the above phosphors), this is to mean that the phosphor has at least one (but not necessarily all) of those dopant ions within the material. That is, as understood by those skilled in the art, this type of notation means that the phosphor can include any or all of those specified ions as dopants in the formulation.

Further, it is to be understood that nanoparticles, quantum dots, semiconductor particles, and other types of materials can be used as wavelength converting materials. The list above is representative and should not be taken to include all the materials that may be utilized within the embodiments described herein.

Embodiments of lamps can include any of the aforementioned wavelength conversion materials, and can exhibit various qualities of light characteristics. Some of such qualities of light characteristics are shown in FIG. 3A and FIG. 3B.

FIG. 3A is a color rendering chart 3A00 showing color rendering index (Ra) and red color rendering (R9) exhibited by a circadian-friendly LED white light source of FIG. 2A at three different color temperatures (e.g., 5000° K, 3500° K, and 2500° K).

When the first and second LED emissions are combined in comparable levels, a 5000K color point can be achieved with acceptable color rendering (Ra, R9 of 80, 65 respectively). Moreover, this emission spectrum can have a high relative circadian stimulation (as defined above) similar to that achieved with a D65 reference illuminant (daylight). When the second LED emission is reduced to a very low level (or turned off), the first LED emission dominates, and a low-circadian-stimulating spectrum is achieved at 2500K with Ra, R9 of 93, 65. At an intermediate point, a 3500K color temperature is provided with Ra, R9 of 85, 88 and a mid-level stimulation of the circadian system. Accordingly, this LED white light source can be used to achieve high-stimulating 5000K light in the morning, 3500K mid-stimulating illumination in the afternoon, and low-stimulating 2500K light in the evening, all while maintaining acceptable white light quality (Ra≥80, R9≥50). Total power to the first and second LEDs may be adjusted to provide the desired total illuminance levels.

FIG. 3B is a chart 3B00 showing relative circadian stimulation resulting from a circadian-friendly LED light source.

FIG. 3B shows the relative circadian stimulation of the circadian-friendly light source illustrated in FIG. 2A, using a 95 nm FWHM CSWR as modeled after Brainard. By combining both first and second LED emissions to achieve a color temperature of 5000K (202 in FIG. 2A), a very high circadian stimulating effect is achieved. As shown in FIG. 3B, at 5000K the relative circadian stimulation is approximately 2.8 times higher than that of the CIE A reference illuminant. This level of circadian stimulation is close to that achieved with an illuminant associated with daylight (e.g., D65 illuminant, as shown), which has a relative circadian stimulation 3.1 times higher than that of the CIE A reference illuminant. When the second LED is turned down (or off) so that the first LED emission dominates, the 2500K spectrum is achieved (206 in FIG. 2A), which has a very low circadian stimulation (within 10% of that of the CIE A reference illuminant). When the intensity of the first and second LED emission are comparable, an intermediate spectrum at 3500K is achieved (204 in FIG. 2A), which provides a relative circadian stimulation about two times higher than that of the CIE A reference illuminant.

The color may be changed dynamically (either continuously or stepwise) throughout the day, via a clock-controlled driving scheme. Or, the desired color point may be selected using a switching mechanism provided for the end user. Many other automatic and/or human-interface control schemes may be employed, such as power-line communication, WiFi, Zigby, DALI, etc. Different target CCTs are also possible. It is expected that such a light source would have dramatic benefits for health and amenity compared to circadian-unfriendly light sources such as standard blue-based LEDs.

Figure 4A:
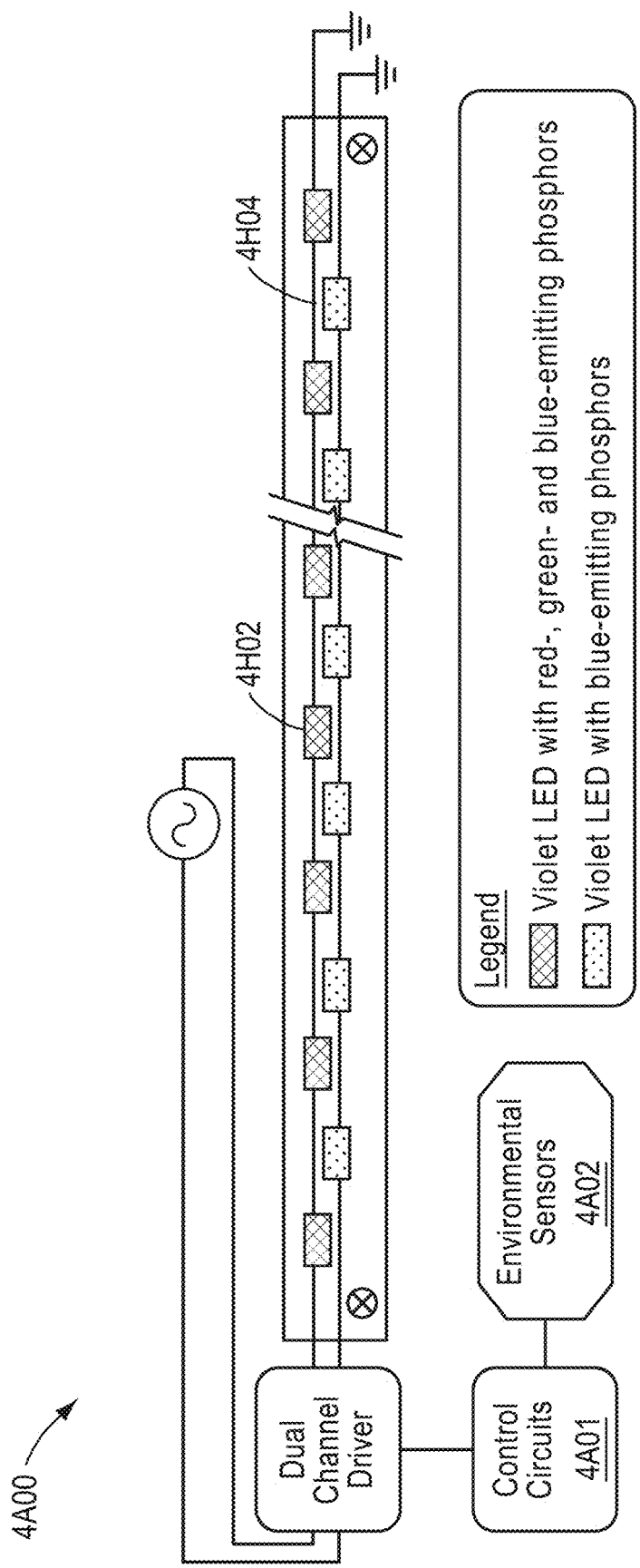
FIG. 4A shows an example of a light strip used to implement an LED white light source that is tunable based on measurable aspects and/or changes in the environment, according to some embodiments.

FIG. 4A shows an example of a light strip used to implement a white light source that is tunable based on measurable aspects (e.g., time of day) and/or changes in the environment. Such a white light source can be formed, for instance, by mixing at least two LED-based sources: e.g., a first using an appropriate mix one set of red-, green- and (optional) blue-emitting phosphors with violet-primary LEDs, and a second using either violet-pumped blue phosphor LEDs or blue-primary LEDs. The two sources can be mixed throughout a diurnal cycle to form a circadian-friendly LED white light source. Such a light strip may be used, for example, as a light engine for a linear troffer luminaire.

Figure 4B:
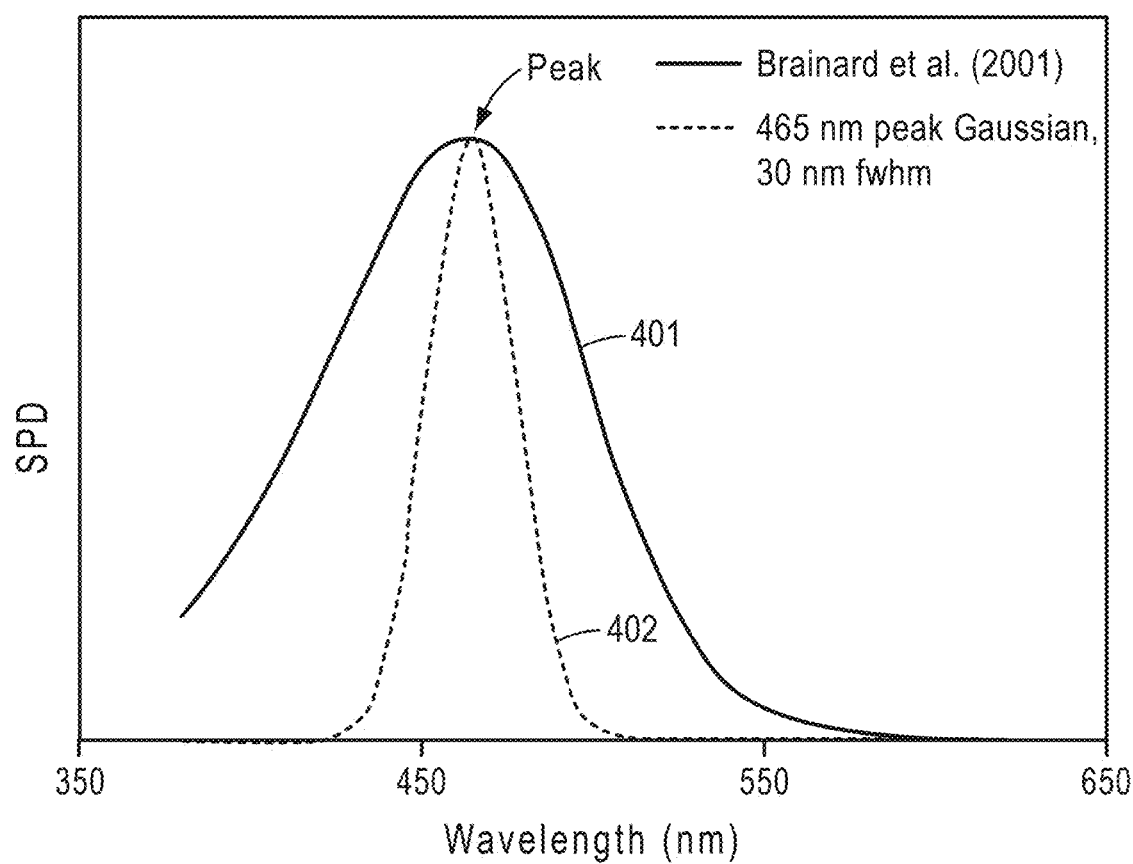
FIG. 4B shows a narrower band (Gaussian) circadian stimulation range with 30 nm full-width-half-maximum (FWHM) and peaked at 465 nm.

In other embodiments, the CSWR can be narrower than described by Brainard (curve 401 in FIG. 4B). For example, consider a 465 nm peak Gaussian CSWR with a FWHM of 30 nm as shown as curve 402 in FIG. 4B. For this narrower CSWR, it is possible to design LED white light sources having a CCT higher than that of CIE A, but with lower circadian stimulation.

FIG. 4C1 shows a first LED emission 4C100 of a violet-primary LED pumping a green and red phosphor 403. This emission is at 3286K but has a CS 50% relative to CIE A. Thus, the LED white light source has a higher CCT than CIE A but a lower circadian stimulation. The second LED emission 4C200 (FIG. 4C2) is a violet primary LED pumping a blue phosphor having a peak emission wavelength of 477 nm 404. The first and second LED-based emissions can be combined, as shown in FIG. 4D1, to tune from about 5000K to about 3300K, varying the CS from about 300% to less than 50% that of CIE A, while maintaining a white point within 4 points of the Planckian, a CRI>80, and an R9>10, as shown in the table in FIG. 4D2.

This change in CS can also be quantified by considering the relative spectral content (e.g., fraction of the SPD) in specific spectral ranges. Two ranges of interest are the relative spectral content in the 'violet-blue' (VB) range 400 nm to 440 nm and in the 'blue-cyan' (BC) range 440 nm to 500 nm. The former range is relatively less circadian-stimulating, and the latter range is relatively more circadian-stimulating. The table in FIG. 4D2 shows the relative spectral content for these wavelength ranges. When tuning from 5000K to 3300K, the fraction of total SPD power in the VB range increases slightly (from 0.19 to 0.23) whereas the fraction in the BC range decreases significantly (from 0.20 to 0.05). This re-apportioning of the spectral content from the BC range to the VB range contributes to the low CS of the 3300K SPD. Also, note that the presence of violet light enables the SPD to remain on-Planckian.

In certain embodiments, having a large fraction Fv of the SPD in the VB range or a small fraction Fc in the BC range corresponds to a low CS, and vice-versa. For example, an SPD characterized by a Fc>0.1 may have a high stimulation, and an SPD characterized by a Fc<0.06 and Fv>0.05 may have a low stimulation. Similarly, an SPD characterized by a Fc/Fv>0.5 may have relatively high stimulation, and an SPD characterized by a Fc/Fv>1 may have a high stimulation. An SPD characterized by a Fc/Fv<0.4 may have a relatively low stimulation and an SPD characterized by a Fc/Fv<0.2 may have a low stimulation. These ranges correspond to certain embodiments of LED white light sources provided by the present disclosure, including those of FIGS. 4A-4N2 and FIGS. 5A-5C4.

Therefore, the CS can, in general, be proportional to the ratio Fc/Fv, with higher values being associated with greater circadian stimulation. CS can also, in general, be proportional to the Fc content. Furthermore, in certain embodiments, increasing the VB content of a LED white light source will decrease the BC content, and conversely increasing the BS will result in reduced VB content.

Fv and Fc represent the fraction of power in the SPD within either the VB wavelength range or the BC wavelength range, respectively. For example, where the total power in the SPD is 1, when 10% of the power in the SPD is in the VB wavelength range, Fv is 0.1; and when 10% of the power of the SPD is in the BC wavelength range, Fc is 0.1.

In certain embodiments, Fv is less than 0.2, less than 0.15, less than 0.1, less than 0.08, and in certain embodiments, less than 0.05.

In certain embodiments, Fv is greater than 0.2, greater than 0.15, greater than 0.1, greater than 0.08, and in certain embodiments, greater than 0.05.

In certain embodiments, Fc is less than 0.2, less than 0.15, less than 0.1, less than 0.08 and in certain embodiments, less than 0.05.

In certain embodiments, Fc is greater than 0.2, greater than 0.15, greater than 0.1, greater than 0.08, and in certain embodiments, greater than 0.05.

Various combinations of Fv and Fc can be provided consistent with providing a LED white light source of the present disclosure. It is significant that using the devices and methods provided by the present disclosure, Fv, i.e., the spectral content in the VB range from 400 nm to 440 nm can be controlled to provide a desired white light emission and maintain desired attributes such as CCT, CRI, Ra, Duv, and others. Use of violet emitting LEDs and select phosphors, and optionally additional LEDs emitting at other wavelengths, provide the ability to more accurately control the content in the VB range from 400 nm to 440 nm.

In certain embodiments, Fc/Fv is from 0.1 to 1, from 0.1 to 0.8, from 0.1 to 0.6, and in certain embodiments, from 0.1 to 0.4.

In certain embodiments, Fc/Fv is less than 0.1, less than 0.2, less than 0.3, less than 0.4, less than 0.5, and in certain embodiments, less than 0.6.

In certain embodiments, Fc/Fv is from 0.5 to 1.5, from 0.5 to 1.3, from 0.5 to 1.1, and in certain embodiments, from 0.5 to 0.9.

In certain embodiments, Fc/Fv is greater than 0.5, greater than 0.6, greater than 0.7, greater than 0.8, greater than 0.9, and in certain embodiments, greater than 1.

It should be appreciated that it is not trivial to obtain the high quality of light demonstrated by the embodiments of the present disclosure. Although one can reduce the CS of a light source by simply removing all (or most) of the blue and cyan emission—without supplementing it with violet radiation, the resultant color rendering index would be poor because of the absence of short-wavelength light in the spectrum. Furthermore, it can be difficult to maintain the chromaticity of a source near-Planckian (resulting in a source with a low CCT and/or a greenish tint). In contrast, embodiments of the present disclosure balance the amount of blue and violet light and thereby facilitate modulating the CS while maintaining high quality of light (e.g., CRI, Ra, Duv).

It is possible for a second LED emission to use a primary blue-emitting LED with a suitable dominant wavelength to tune along the Planckian. For example, as shown in FIG. 4E1 and FIG. 4E2, an about 480 nm peak emission LED may be used in place of the blue-phosphor-based LED of FIG. 4C2. FIG. 4E1 shows an emission spectrum of a first LED-based source 420 and FIG. 4E2 shows a spectrum 421 of a blue-emitting LED. By combining the emissions shown in FIG. 4E1 and FIG. 4E2, a similar effect is achieved as shown by the combined spectrum 422 in FIG. 4F1, with slight differences in color properties and levels of circadian stimulation, as shown in the table in FIG. 4F2.

Figure 4G:
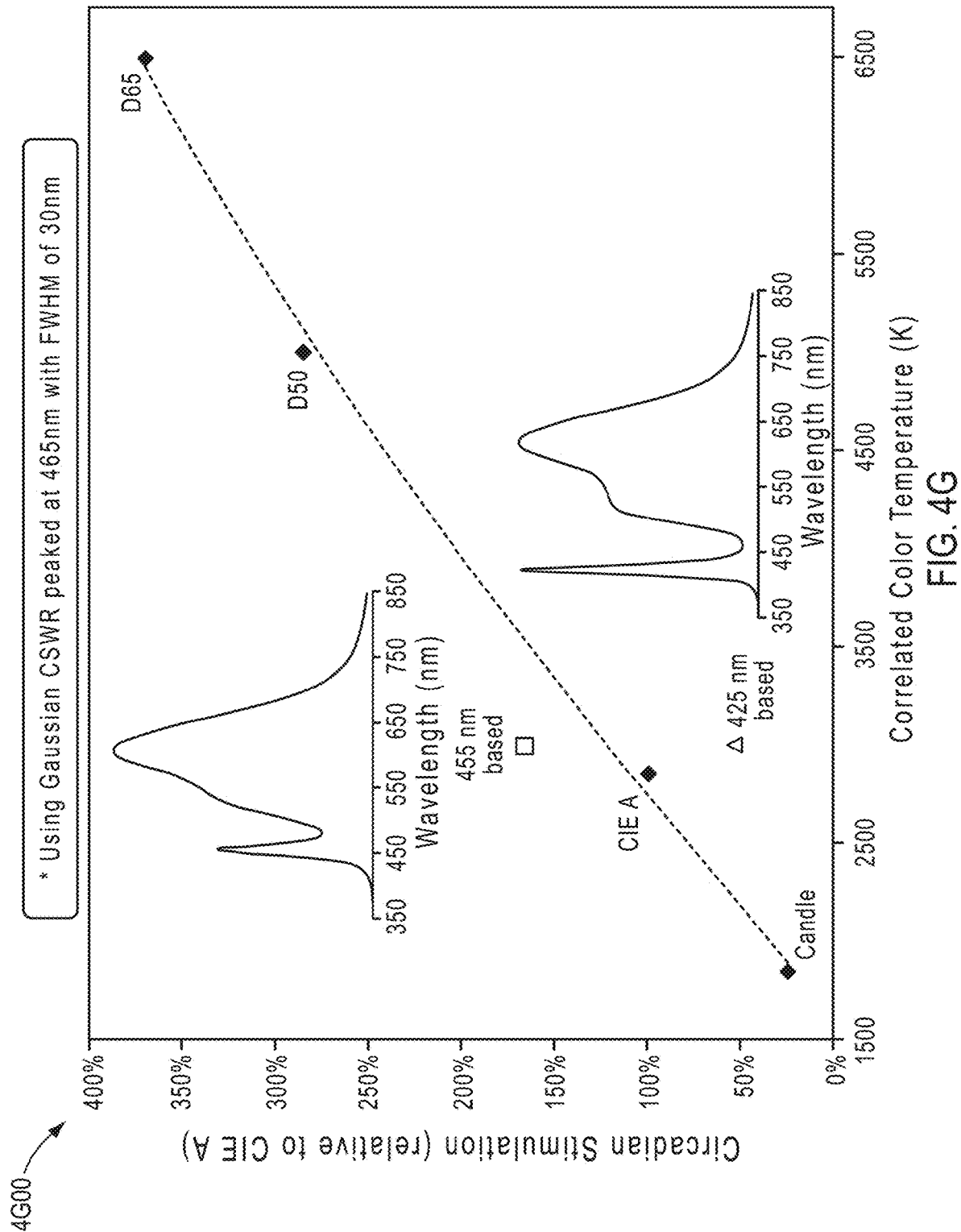
FIG. 4G shows circadian stimulation as a function of color temperature for certain light sources.

In the case of a 465 nm peak Gaussian CSWR with a FWHM of 30 nm, it is illustrative to compare the relative CS for common light sources with LED white light sources provided by the present disclosure. FIG. 4G shows the CS (normalized to that for CIE A) as a function of color temperature for common light sources such as candlelight (1850K), CIE A (2856K), D50 phase daylight (5000K), and D65 phase daylight (6500K). The CS varies from about 25% (candlelight) to almost four times (D65) that of CIE A. Also plotted are the CS for a 455 nm blue primary LED two-phosphor 3000K LED, and that for a 425 nm violet primary LED two-phosphor 3000K LED. The difference in circadian stimulation is remarkable, with that for the 455 nm-based LED white light source being more than 1.5-times higher than that of CIE A, and more than three times that of the 425 nm-based LED white light source. It is worth noting that $Ce^{3+}$ garnet phosphors (e.g., "YAG") are not highly absorbing in the violet, so for the 425 nm-based LED it may be desirable to use a $Eu^{2+}$ phosphor for the green, as well as for the red, emissions.

Figure 4H:
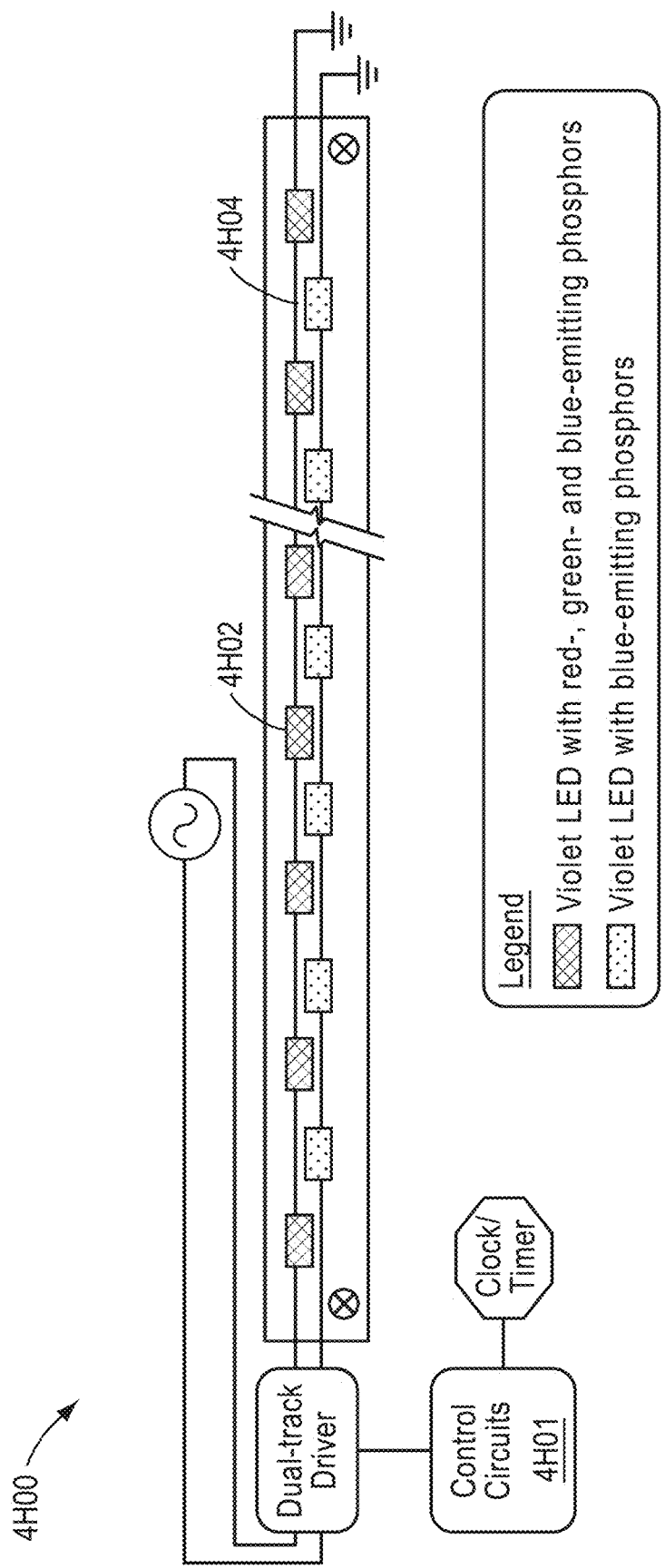
FIG. 4H shows a light strip having two different sets of LEDs and controlled by a clock to adjust the ratio of LED emission wavelength to implement a circadian-friendly LED light source, according to some embodiments.
Figure 41:
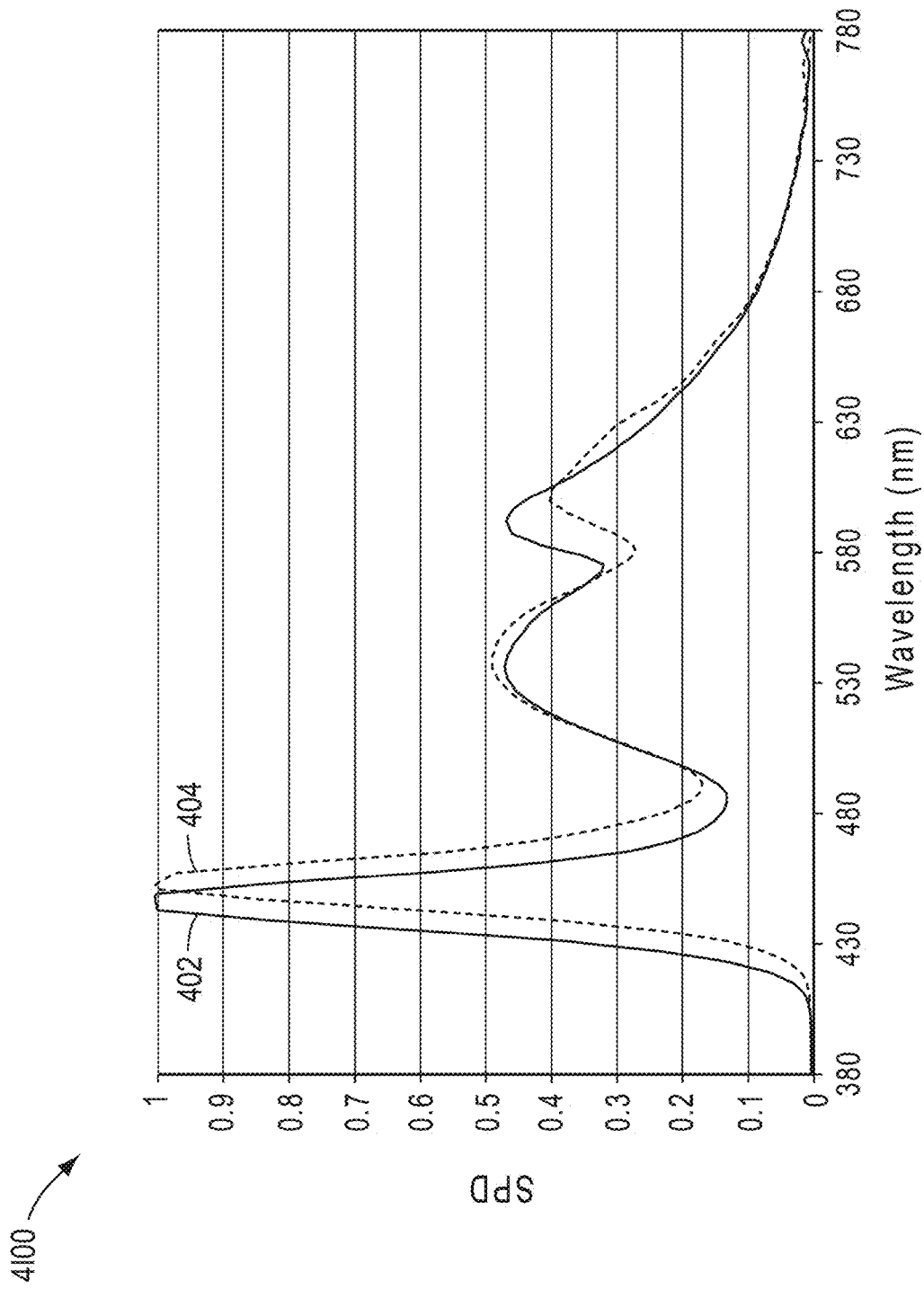

FIG. 4H shows light strip having two different sets of LED-based emitters, and a clock/timer, control circuits 4H01, and a driver to control the ratio of emissions of the two different sets of LED-based emitters to implement a circadian-friendly LED white light source, according to some embodiments.

As shown, a first group of violet-primary LEDs with an appropriate mix of red-, green- and (optionally) blue-emitting phosphors 4H02 can be combined with a second group of violet-primary LEDs with blue phosphors, or blue-primary LEDs, 4H04.

Figures 6A, 6B:
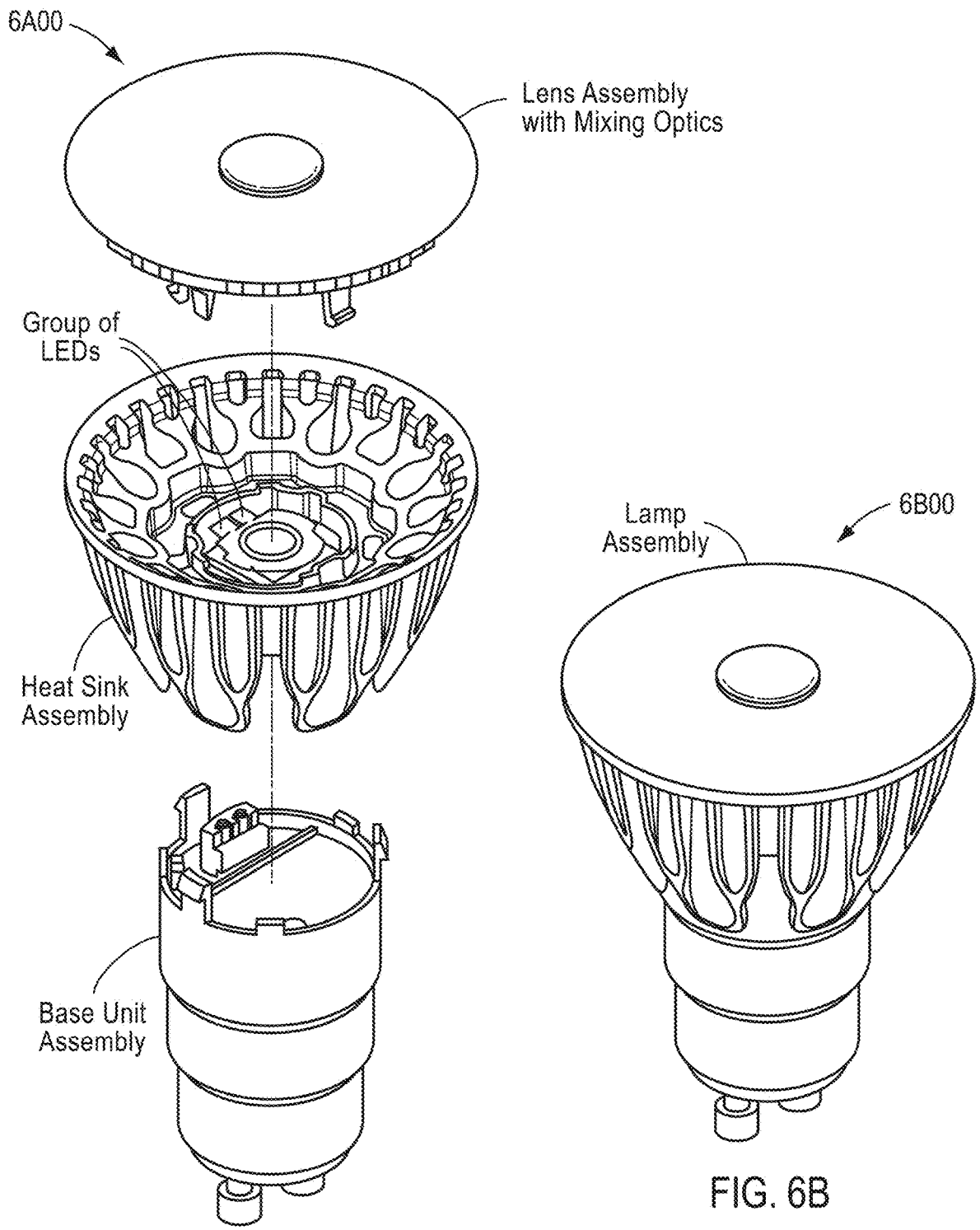
FIG. 6A shows an exploded view and FIG. 6B shows an assembly view of a LED lamp employing a circadian-friendly LED light source, according to some embodiments.

The first and second groups of LED-based emitters may be contained in separate packages, and the light combined with mixing optics, or the LED-based emitters may be incorporated into a single package, such as a s chip-on-board (COB) package (e.g., see the arrangement of FIG. 8) and/or linear COB packages. COB packages can be used in a lamp assembly as is shown in FIG. 6A and FIG. 6B.

In addition, although the above embodiments describe two-channel tuning methods to provide varying levels of circadian stimulation while maintaining a high quality of light, which can be useful to minimize cost and complexity, it is possible to use three or more channels using the devices and concepts provided disclosure. More channels offer more degrees of freedom in terms of light source selection, and tuning for arbitrary (e.g., non-linear) curves in chromaticity space, but at the cost of higher levels of complexity in terms of luminaire design, LED procurement, mixing, and control.

In addition to the elements shown in FIG. 4H one or more light mixing optics (not shown) may be used to mix the LED emissions first group and second group to provide a uniform or other desired light color appearance. Still further, secondary optics can be used to achieve a desired light distribution pattern.

The foregoing discussion is focused on lighting systems and benefits resulting from a reduced CS. However, display systems can also benefit from a reduced CS.

FIG. 4I shows measured SPDs 4100 for two display systems with a white screen—a laptop screen 402 and a smartphone screen 404. Examples of other display systems are illustrated in FIGS. 15D1 through 15E2. Both displays shown in FIG. 4I have CCTs of about 6500K, which is typical for display screens. Both are lit by blue-primary LEDs and the emission spectra are characterized by a large blue peak. The relative circadian stimulation is about 330% for the laptop and about 470% for the phone screen.

Figure 4J:
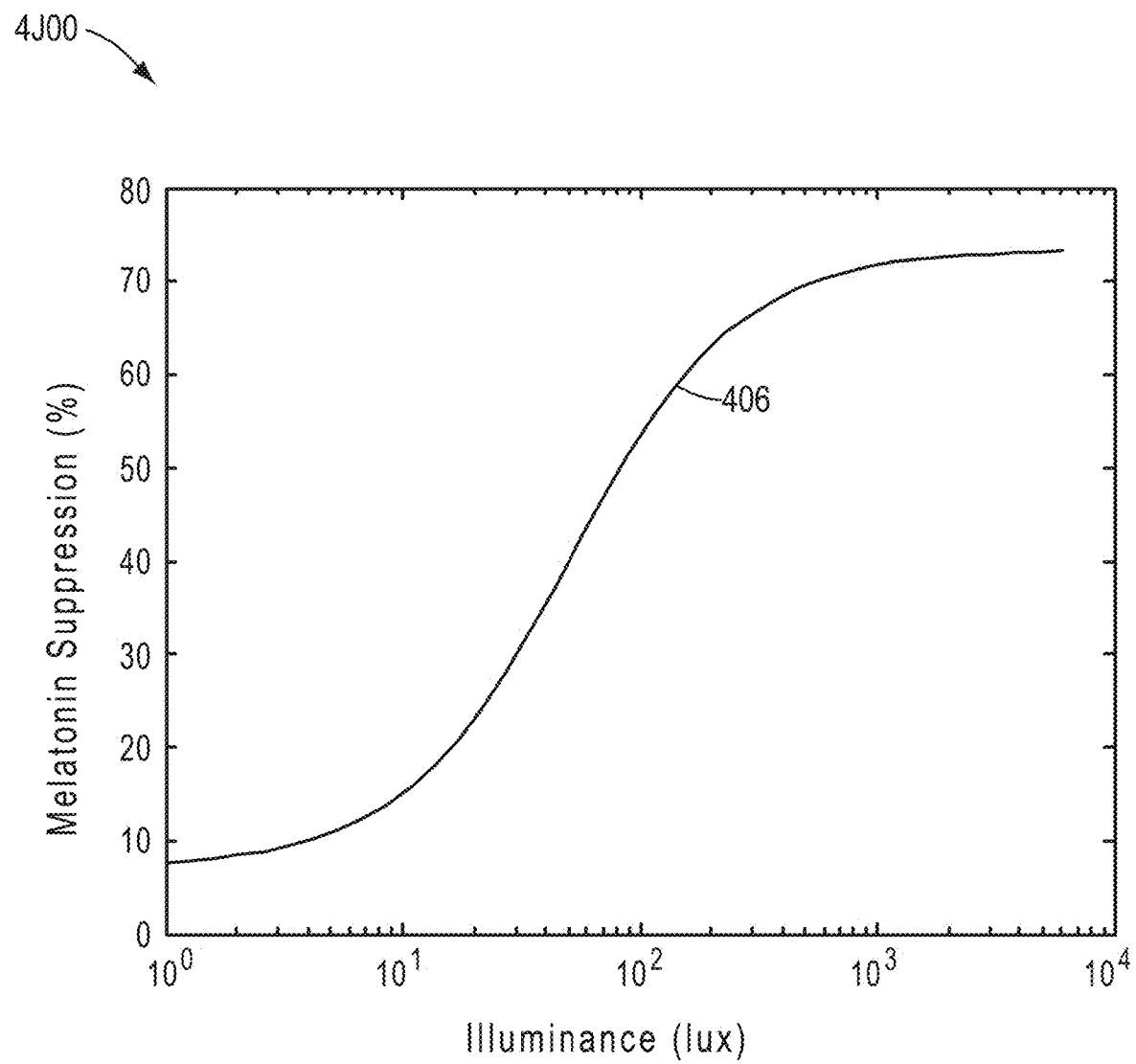
FIG. 4J shows predicted melatonin suppression, according to some embodiments.

FIG. 4J shows the predicted melatonin suppression 406 (after 90 min exposure to a white screen of a smartphone) versus luminance for the smartphone screen. In practice, luminance levels for displays can be high—one hundred to several hundreds of lux in some cases (for instance if the device is held close to the face). Therefore, the net impact on the circadian system can be significant and can disrupt sleep patterns, even for a relatively short exposure time.

For display applications, there are already software solutions that aim at reducing circadian disruption. For instance, software such as "f.lux" can adapt the CCT of the screen with time: during the day, the CCT is about 6500K, but as the night falls the CCT is 'warmed' to about 3400K.

Figure 4K:
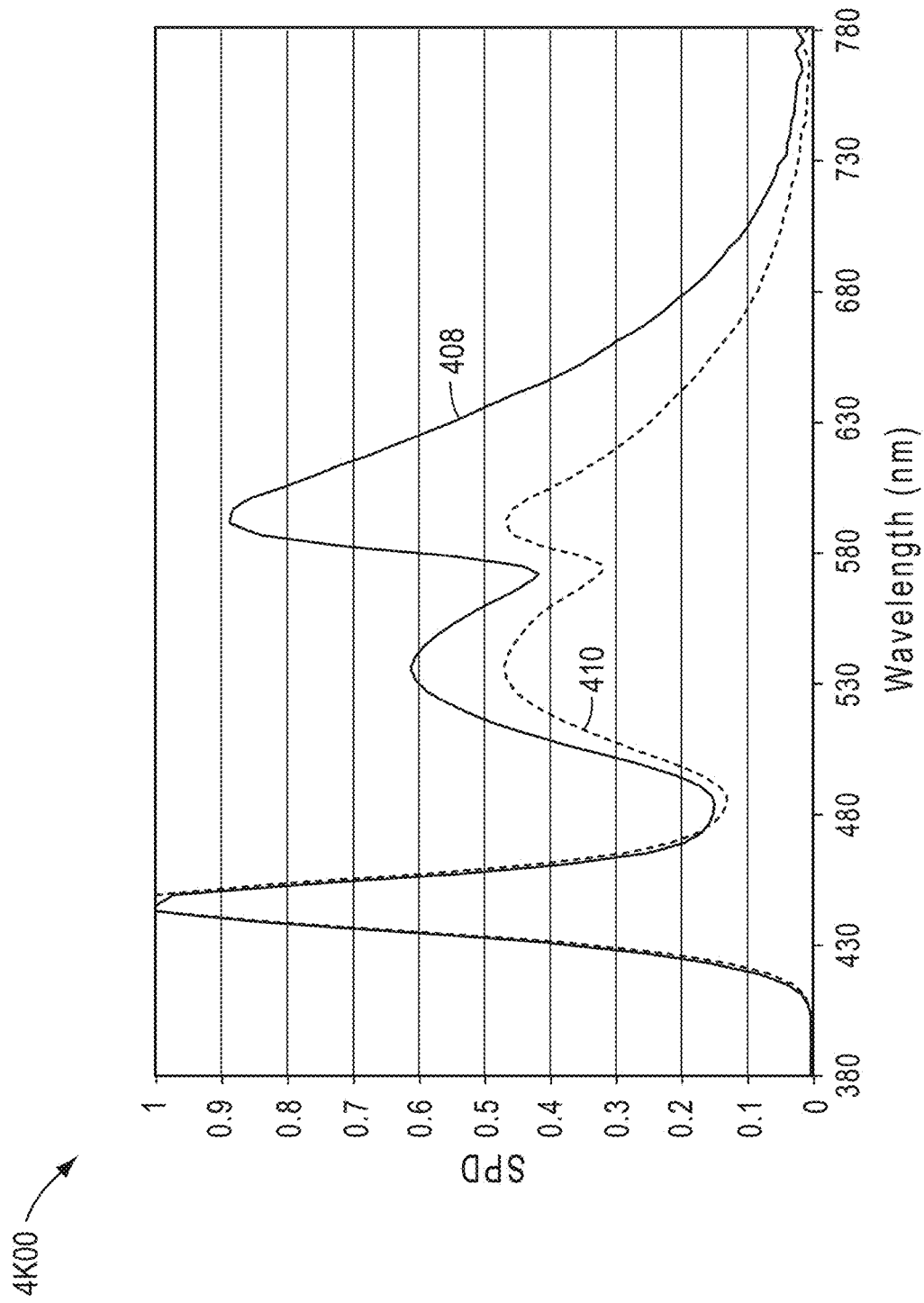
FIG. 4K shows the spectrum emitted by a white screen, according to some embodiments.

FIG. 4K shows an example of a spectrum emitted by a white screen using this software: curve 410 is for the standard emission (6500K) and curve 408 is for the warmed emission (about 3400K nominally).

The reduction in CCT is beneficial because the relative circadian stimulation is less at lower CCT. Namely, the relative circadian stimulation is about 330% for the standard emission and about 210% for the warmed screen (assuming equal luminance), relative to illuminant A. While this is an improvement, stimulation is still high for the warmed screen due to the use of blue-pump LEDs. Also, it can be useful to reduce CS while still achieving the more typical electronic display white center point (typically 6000K to 7000K).

Therefore, as with lighting systems, a careful choice of the emission wavelength and profile of the primary LED and of the overall SPD is important to obtain a display system with a low circadian stimulation.

FIG. 4L1 illustrates relevant spectra for typical LED-lit liquid crystal displays (LCD), which are used in many applications including televisions, monitors, laptop and notebook computers, gaming systems, and portable devices such as tablets, phones, MP3 players, etc. FIG. 4L1 shows spectra for a blue color filter 412, a green color filter 414, and a red color filter 416 (collectively, CFs) which are employed in conjunction with an LCD display to control color. A typical LED spectrum (e.g., LED spectrum 418) is a blue primary-based LED pumping a yellow (and/or red) emitting phosphor system. Filtering by the red, green and blue filters results in a transmitted spectrum, for example, a white transmitted spectrum 419 if all three filters fully transmit. A typical color gamut of this system (shown as triangle 426 in FIG. 4L2) is limited in the green and red, and covers an area in x-y chromaticity space of about 79% with respect to the National Television System Committee gamut standard 422 (NTSC, 1953). As discussed above, such an LED-based source (with a primary peak wavelength typically in the 440 nm to 460 nm range) is inherently highly circadian stimulating, which can be undesirable especially for viewing in the evenings and nighttime. FIG. 4L2 also shows the Planckian locus 424 and the boundaries of the (xy) colorspace 420.

Figure 4M:
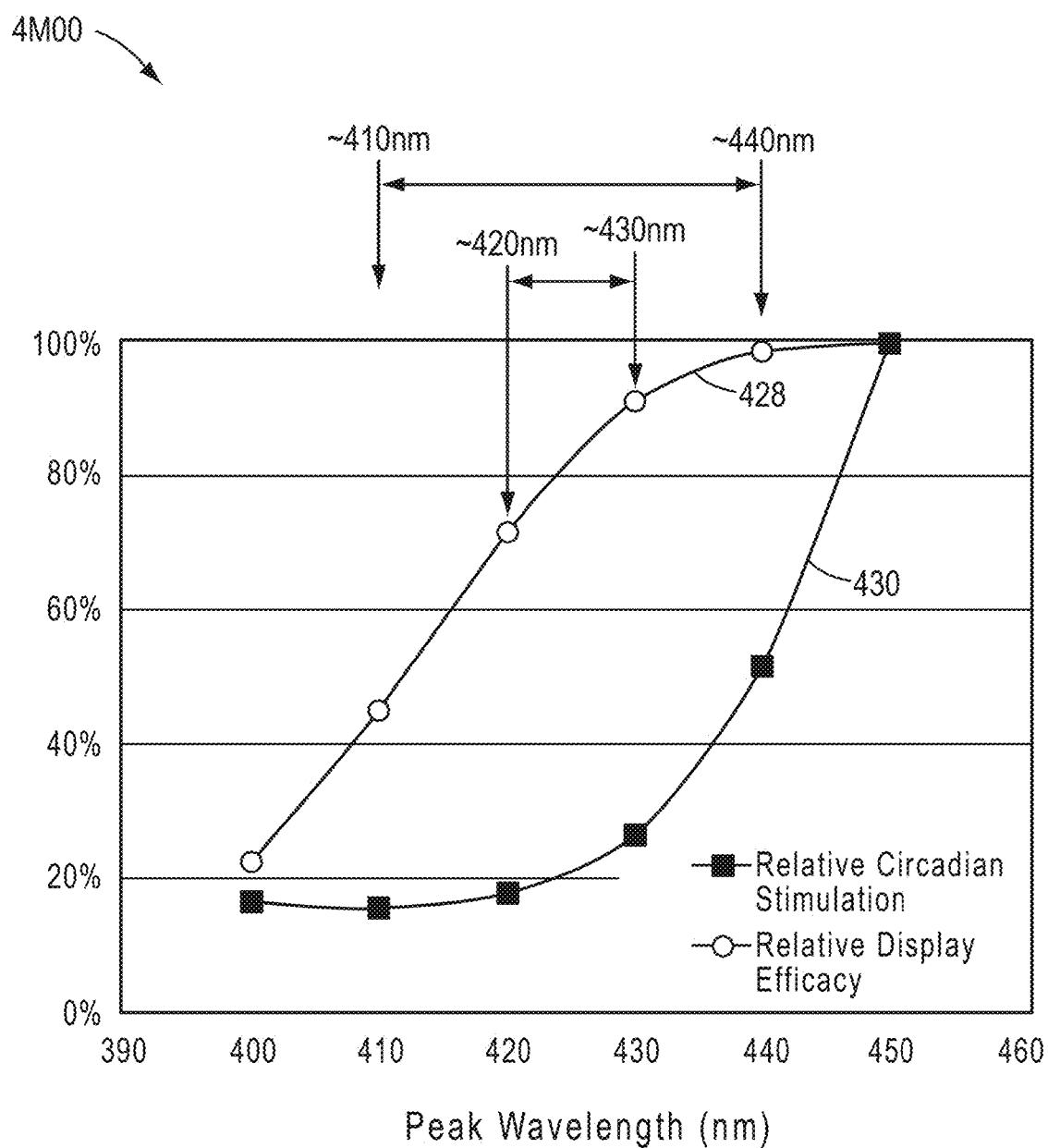
FIG. 4M shows calculated relative circadian stimulation and relative display efficacy.

FIG. 4M shows the calculated relative CS (curve 430) and relative display efficacy (curve 428) as the "blue" LED primary peak wavelength is decreased (using the same phosphor emission, while maintaining the same display white color point), using a 465 nm peak Gaussian CSWR with a FWHM of 30 nm. For peak wavelengths less than 440 nm, there is a significant drop in CS, which reaches a minimum at about 410 nm. The efficacy reduces also, but more slowly with decreasing peak wavelength, suggesting an optimum peak wavelength range between 410 nm and 440 nm or between 420 nm to 430 nm for a reduced-CS display.

FIG. 4N1 shows embodiments for which the phosphor system is tuned to better work with a chosen primary peak emission wavelength of 425 nm. In FIG. 4N1, 83% NTSC is achieved using phosphors with peak/FWHM (emission) of 530 nm/85 nm and 605 nm/80 nm, with only about a 10% efficacy penalty compare to a 450 nm-based source achieving 79% NTSC. In FIG. 4N2, 90% NTSC is achieved using phosphors with peak/FWHM (emission) of 530 nm/85 nm and 630 nm/80 nm, with only about a 20% efficacy penalty compare to a 450 nm-based source achieving 79% NTSC. One skilled in the art can identify different combinations of phosphors to achieve the desired balance of color gamut and efficacy. Use of a 425 nm wavelength primary LED can reduce CS by about five times, which is extremely significant. Referring to FIG. 4J, a five times reduction for a 100 lux display would reduce melatonin suppression from about 50% to about 20% for a 90 minute exposure.

Application of the present disclosure is not limited to displays based on LCDs. Direct-view LED displays have been demonstrated, using both organic and inorganic LEDs. In these displays individual pixels are made up of active LEDs, which include blue, green, and red emitters and are selectively controlled. Based on embodiments of the present disclosure, the "blue" emitters may be tuned to shorter wavelengths to reduce CS as described. In certain embodiments, using a 465 nm peak Gaussian CSWR with a FWHM of 30 nm, an optimum peak wavelength range for the "blue" emitter can be between 410 nm and 440 nm, more preferably between 420 nm and 30 nm, can be chosen for a reduced-CS display.

It is also possible to mix longer and shorter wavelength primary "blue" LEDs in order to have displays in which CS can be controlled. For example, it may be desirable to have high CS stimulation in the morning (e.g., 440 nm to 460 nm primary "blue") that shifts to shorter wavelength (e.g., 420 nm to 430 nm) during the evening. This can be done by including two sets of primary "blue" LEDs in the display and can be implemented in both LCD and direct-view LED-based displays.

In some cases the color point (or more generally the spectrum) of the embodiments can be tuned automatically in response to behavior or actions of the end user. Examples of such trigger events include the presence of the end user in a room (or a part of the room) for a given amount of time, the movement of the user across the space, the user's general level of activity, specific words or gestures, and/or actions on a device (a smartphone for instance). Such responses may be employed to match the spectrum to the condition of the user (for instance, lower the circadian cycle when the user becomes sleepy or prepares for sleep) or to modify the condition of the user (e.g., detect sleepiness and increase circadian stimulation to lessen it). In some cases, the response can be determined by the user's behavior in combination with other measurable conditions or cues such as time of the day, weather and/or changing weather, amount of outdoor light, etc. In some cases, the cues can be obtained from another "smart" system (another appliance, a smartphone, or other electronic device) which monitors the user's behavior—the cues can then be communicated over a network (wired or wireless) between said smart system and the lighting system, such as a network enabled by a smart-home hub. In some cases the cues relate to the user's past behavior, such as the time the user woke up or his past sleep pattern, which has been recorded by a system such as the user's smart phone.

In some cases, a response can be predetermined by the manufacturer of the system so that a given set of cues leads to a deterministic response. In other cases, the lighting system "learns" from the user. For instance, in a teaching phase, the user (or another person) manually tunes the spectrum. The system learns to associate these settings with specific cues and the tuning is then performed automatically in response to the cues, (e.g., rather than being triggered manually). Learning can be achieved by a variety of machine-learning techniques known to those skilled in the art, such as via a neural network and/or using Bayesian inference.

A specific example of the previous scenario is as follows: The user follows a routine (e.g., a series of actions performed repeatedly with some periodicity) a few hours before going to bed. Such a routine might include leaving the dining table, brushing his teeth, watching TV etc. Cues of this routine are collected by various appliances (TV, toothbrush, motion sensors) and communicated with the lighting system through a wireless protocol. In the teaching phase, the user also tunes the spectrum of the lighting system to reduce circadian stimulation—for example, the user the lighting system to a non-stimulating setting a few hours before going to bed. Once the system has associated these settings with one or more cues of the routine, and with an approximate hour, the tuning occurs automatically to help reduce the circadian response before the user goes to bed. Conversely, tuning can also occur in the morning to stimulate the circadian system.

Such automated behavior can be used for a variety of light-emitting systems—including lighting appliances per se, and for display systems (e.g., TV and computer screens, tablets, phones, etc.). Such lighting systems may for instance adapt their spectrum to reduce circadian stimulation a given time before the user goes to bed. In the case of display systems, the change in LED spectrum may be combined with software changes (such as the screen's color point) in order to further reduce circadian stimulation. Such automated behavior can be implemented in a wide variety of lighting situations. Strictly as one example, a light strip can be fitted with sensors to take-in and/or learn from measurable aspects and/or changes in the environment, and in response, tune circadian-friendly emissions.

While the previous examples assumed a domestic setting, such embodiments with automatic or 'smart' tuning can be used in other contexts such as in a professional context. For example, in an office setting, the lighting system may adapt to monitor used activity and increase CS accordingly; or the CS may be increased in the morning, reduced near the end of the work day, or adapted to complement the outside lighting conditions (which could vary with weather and season). System tuning may follow a simple timing scheme or also take into account the workers' behavior. Embodiments may also be used in other contexts where sleep pattern is affected, including night-shift worker facilities, long-range travel (such as airplane flights), care facilities for the elderly.

Further, in various cases, the intensity of the light emitted by the system may be tuned together with its spectrum to further influence CS. For instance, the intensity may be dimmed as the spectrum is tuned for lower CS. In the case of a display, the luminance of the display may be dimmed and its CS may be lowered if the ambient light in the room decreases—this can be detected by a simple light sensor connected to the display.

Figure 5A:
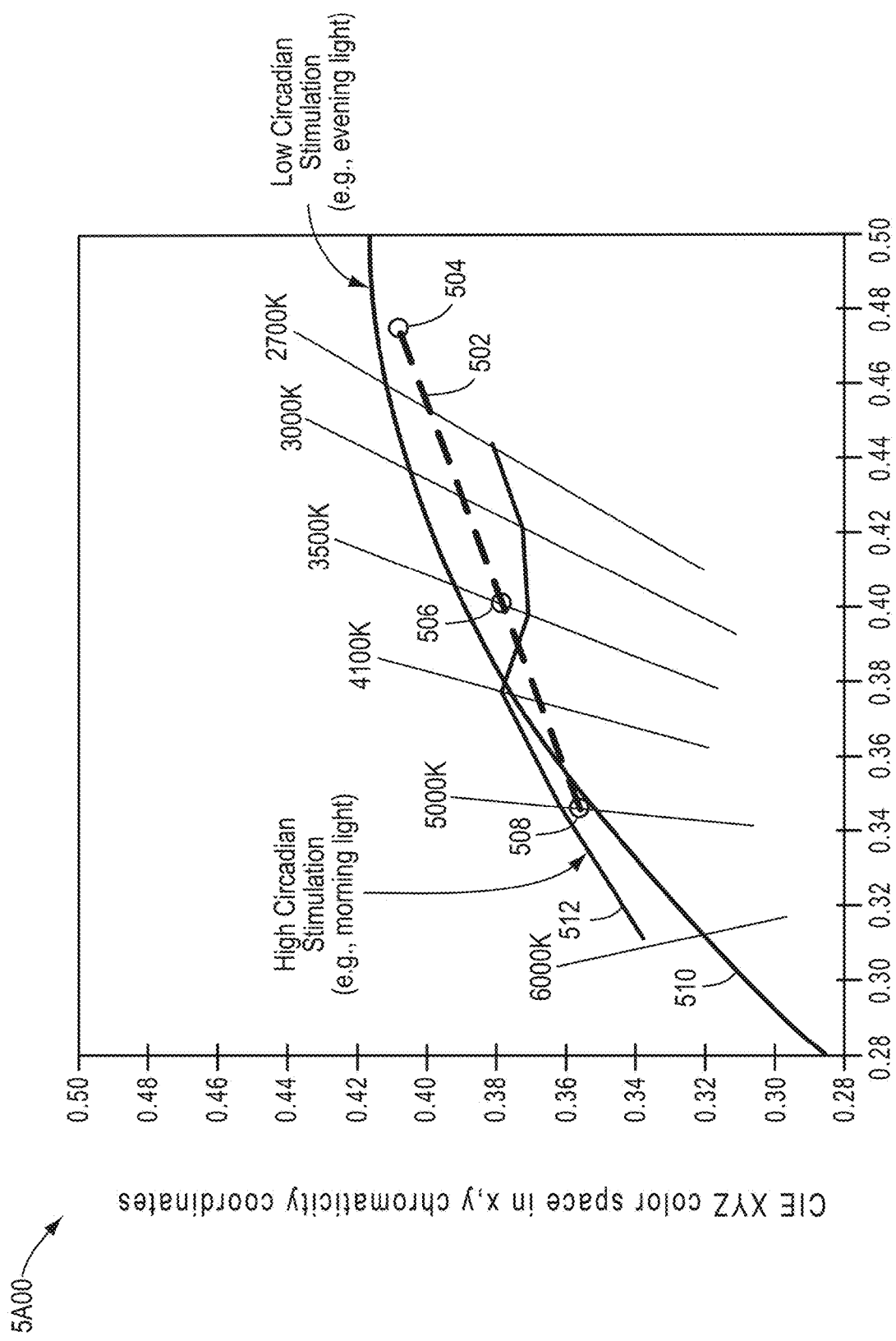
FIG. 5A is a chart showing a linear chromaticity curve in x-y chromaticity space as produced by a circadian-friendly LED light source, according to some embodiments.

FIG. 5A is a chart 5A00 showing a linear chromaticity curve 502 produced by a circadian-friendly LED white light source in x-y chromaticity space. FIG. 5A also shows the Planckian loci 510 and minimum-hue-shift curve 512 as described by Rea and Freyssinier, Color Research and Application 38, 82-92 (2013).

The Planckian loci form a curve in chromaticity space, leading to the popular notion that a linear dual-track tunability cannot properly replicate white emission across a wide range of color temperatures. However, recent psychophysical experiments show that the definition of "white" may deviate from the Planckian curve. In particular, subjects tend to observe less tint for color points below the Planckian loci.

This observation has two ramifications: 1) a person's perception of "white" is somewhat arbitrary, and 2) tinting below the Planckian curve may not only be acceptable, but perhaps preferred. Opening up this region in chromaticity space allows for the engineering of dual-channel tunable white emission. The chromaticities for the three color temperatures described for a circadian friendly light-source (FIG. 2A) are shown (e.g., see point 504, point 506, and point 508) superimposed on the Planckian loci and the "minimum-hue-shift" points. Based on the arguments above, these three color points (and those in between) can provide an acceptable white appearance, as well as good color rendering properties.

Again this is not trivial to achieve because the most obvious way to reduce the CS of a light source is to remove blue or cyan light, thus shifting the chromaticity above the Planckian (and away from the preferred chromaticity curve 502 shown in FIG. 5A).

Figure 5B:
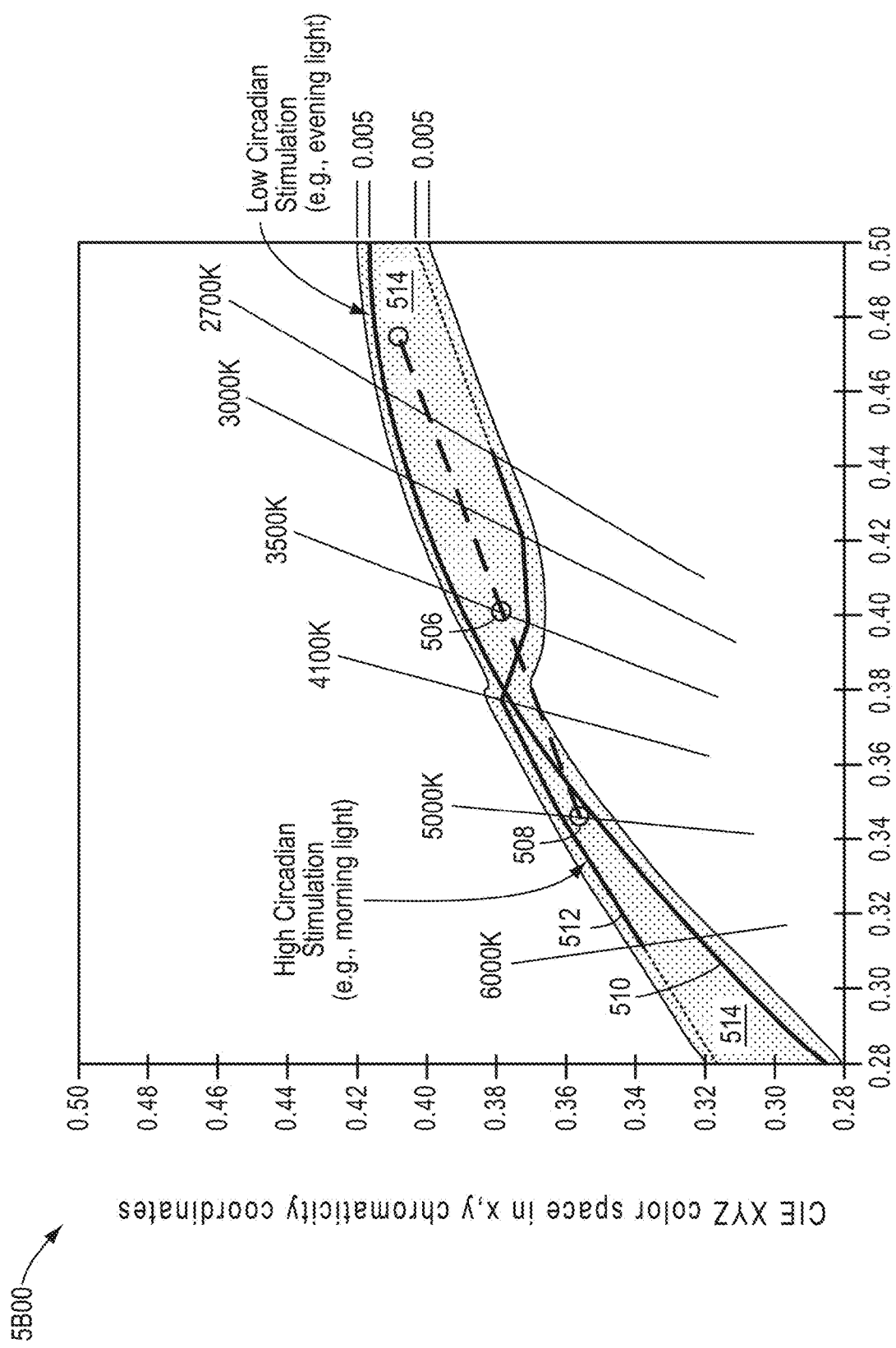
FIG. 5B is a chart showing the shape of a white light bounding region as produced by a circadian-friendly LED light source, according to some embodiments.

FIG. 5B is a chart 5B00 showing the shape of a white light bounding region 514 as produced by a circadian-friendly LED white light source, according to some embodiments. The white light bounding region 514 is taken as the range limits of the Planckian loci 510 and "minimum-hue-shift" curves, inclusive of a±0.005 border region in x-y chromaticity space.

As shown in FIG. 5B, the white light bounding region is highlighted with hatching. In particular, the hatched region 514 represents varying ratios of color mixing, and bounds of a white light region.

In yet other embodiments, the change in circadian stimulation is not associated with a change in CCT or chromaticity. This can be useful in situations for which a given CCT (e.g., 3000K or 6500K) is desired at all times, but the stimulation should vary through the day. This can be useful for lighting applications and for display applications, where CS may be changed without the user being aware in a change in illumination. Such embodiments may, for example, be achieved by combining two LED-based tracks emitting light with a CCT of 3000K. One track can have a large relative circadian stimulation, and the other can have a low circadian stimulation. More specifically, the first track may include blue pump LEDs and phosphors and the second track may include violet LEDs and phosphors. As disclosed herein, the emission spectrum from each track can also be designed to provide high quality of light (e.g., a CRI above 80). In such systems, it may be desirable to design the spectra such than their chromaticities are similar perceptually rather than nominally. Alternatively, it may be desirable to compute the chromaticities with suitable color matching functions (CMFs) such as the 1964 CMFs or other modern CMFs, rather than the conventional 1931 2 degree CMFs. This is because the predictions of the 1931 2 degree CMFs are sometimes poorly representative of user perception. In addition, chromaticity calculations may be performed for a given demographic group (e.g., taking into account the reduction of sensitivity to short-wavelength light for elderly users).

Such embodiments, with a stable CCT, are illustrated in FIG. 5C1 through FIG. 5C4, in which two sets of LED-based sources are controlled independently: 1) a blue primary based LED white source at 3300K with CRI about 80 and R9 greater than 0 ("BLED" 502), and 2) a violet primary based LED white source at 3300K with CRI about 80 and R9 greater than 0 ("VLED" 504). When the BLED devices are on and the VLED off, the circadian stimulation is high (210% of CIE A). Alternatively, When the VLED devices are on and the BLED off, the circadian stimulation is low (54% of CIE A). In mixed combinations, the circadian stimulation varies between these two levels; however, the chromaticity is nominally unchanged. In other embodiments the primary blue LEDs could be replaced by blue phosphors pumped by shorter wavelength LEDs. FIG. 5C2 shows the CIE 508 for an LED-based white light source described above and FIG. 5C3 shows an example of the combined VLED and BLED spectrum 506. The CS for representative BLED fractions is provided in FIG. 5C4.

Here again, the change in CS can also be related to a change in relative spectral content (e.g., fraction of the SPD) Fv in the 'violet-blue' (VB) range 400 nm to 440 nm and Fc in the 'blue-cyan' (BC) range 440 nm to 500 nm. Referring to FIG. 5C1, for SPD 502, Fv=0.01 and Fc=0.14 and for SPD 504 Fv=0.24 and Fc=0.05.

In certain embodiments, an LED emission source is characterized by a color rendering index above 80; a Fv of at least 0.01, at least 0.05, at least 0.1, at least 0.15, at least 0.2, and in certain embodiments, at least 0.25; and an Fc of at least 0.01, at least 0.05, at least 0.1, at least 0.15 at least 0.2, at least 0.25, at most 0.01, at most 0.05, at most 0.10, at most 0.15, at most 0.20 or at most 0.25; or a combination of any of the foregoing.

FIG. 6A shows an exploded view 6A00 and FIG. 6B shows an assembly view 6B00 of a LED lamp forming a circadian-friendly LED light source.

As shown in FIG. 6A and FIG. 6B, the exploded view 6A00 includes a GU10 (10 mm "twist-lock") base for connecting to a 120/230-volt source. Such an embodiment can be used as an MR16 halogen light replacement 6B00 for the 35/50 watt halogen lamps in use since the mid-2000s.

The lamp shown in FIG. 6A and FIG. 6B is merely one embodiment of a lamp that conforms to fit with any one or more of a set of mechanical and electrical standards.

The list above is representative and is not intended to include all the standards or form factors that may be utilized with embodiments described herein.

Figure 7:
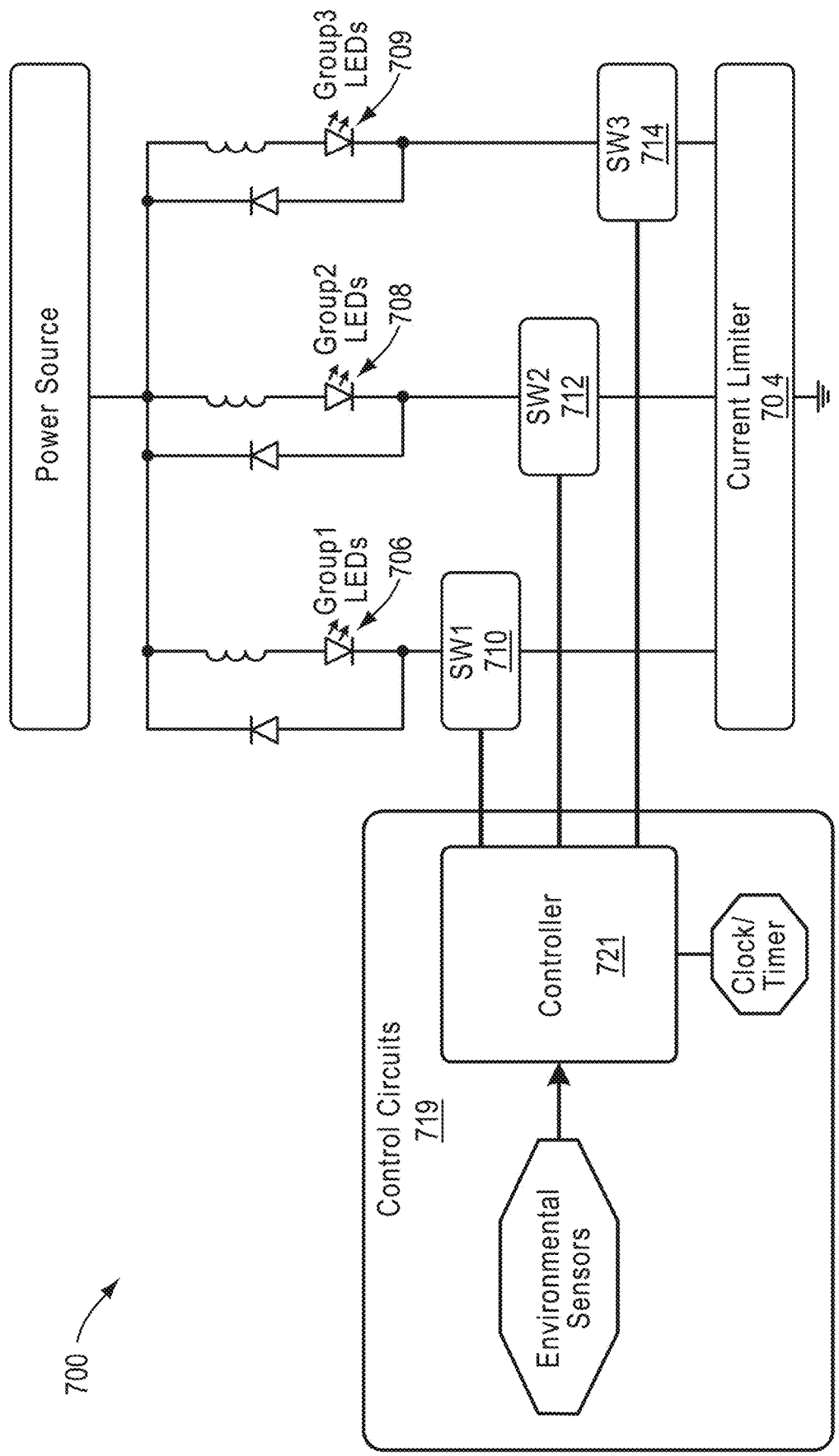
FIG. 7 shows a schematic of a multi-track driver control system as used in an LED lamp employing a circadian-friendly LED light source, according to some embodiments.

FIG. 7 shows a schematic of a multi-track driver control system as used in an LED lamp employing a circadian-friendly LED light source. As shown in FIG. 7, the emission of multiple strings of LEDs is separately varied such that the ratio of output of one string with respect to another string is varied according to a time-based function. For example, the clock/timer can model the sunrise and sunset timings over a 24-hour period, and during the 24 hour period, a violet emitting LED with blue phosphor can be attenuated in afternoon and evening hours. In dual track systems, a linear chromaticity curve 502 can be implemented. With three or more tracks (e.g., the shown three groups of LEDs) non-linear chromaticity curves can be enabled. Suitable driver control systems are disclosed in U.S. Application No. 62/026,899 filed on Jun. 25, 2014, which is incorporated by reference in its entirety.

Control circuits (e.g., control modules) can employ any known-in-the-art techniques, including current limiting based on current or voltage sensing, and/or current limiting based on temperature sensing. More specifically, one or more current limiters (e.g., current limiter 704) can be controlled by any known techniques. The controller and/or current limiters in turn can modulate the current flowing to any individual groups of LEDs (e.g., Group1 LEDs 706, Group2 LEDs 708, GroupN LEDs 709, etc.), which current flowing to any individual groups can be individually increased or decreased using FETs or switches (e.g., SW1 710, SW2 712, SW3 714, etc.). The shown control circuits 719 comprise environmental sensors, and a clock/timer, each of which provide inputs to controller 721, which in turn serves to modulate the current flowing to any individual groups of LEDs (e.g., Group1 LEDs 706, Group2 LEDs 708, GroupN LEDs 709, etc.).

Figure 8:
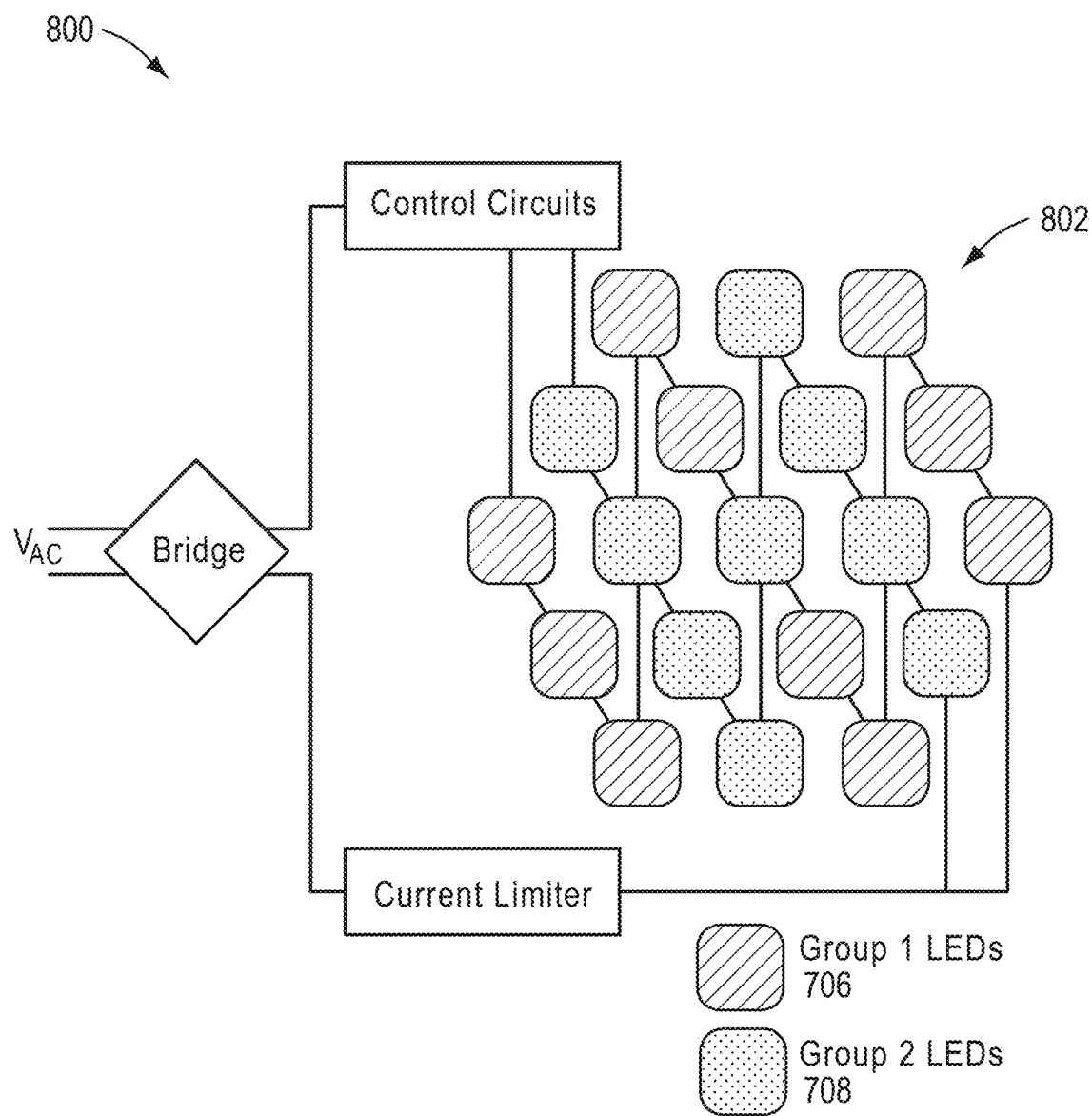
FIG. 8 shows two strings of LEDs in an intermixed physical arrangement to form a two-track, circadian-friendly arrangement as used in an LED lamp, according to some embodiments.

FIG. 8 shows two strings of LEDs in an intermixed physical arrangement 802 to form a two-channel, circadian-friendly arrangement 800 as used in an LED lamp. As shown, the control circuits can employ any known-in-the-art techniques to independently modulate the current flowing to either of the shown groups of LEDs (e.g., Group1 LEDs 706, Group2 LEDs 708).

Each of the Group1 LEDs, and Group2 LEDs comprise individual patterned-phosphor chips so that the circadian-friendly source may be condensed into a compact area, for example, for directional lighting. A mixing optic can be included to mix the two types of LED light emissions (e.g., for homogeneity). The arrangement shown is illustrative and other arrangements are suitable. Techniques for patterning phosphors are disclosed in U.S. application Ser. No. 14/135,098, filed on Dec. 19, 2013, which is incorporated by reference in its entirety.

Figure 9A:
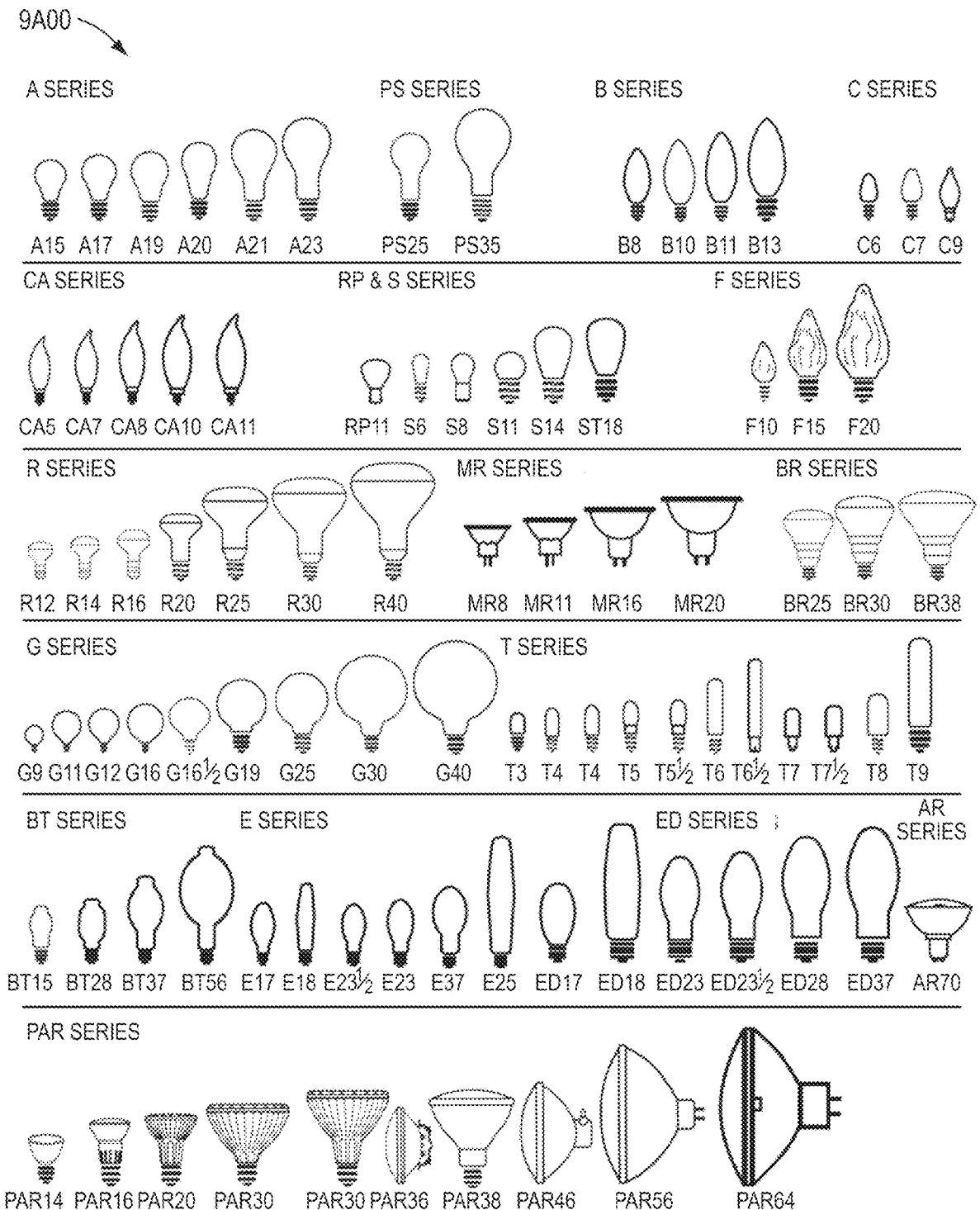
FIG. 9A presents a selection of lamp shapes corresponding to various standards, according to some embodiments.
Figure 9C:
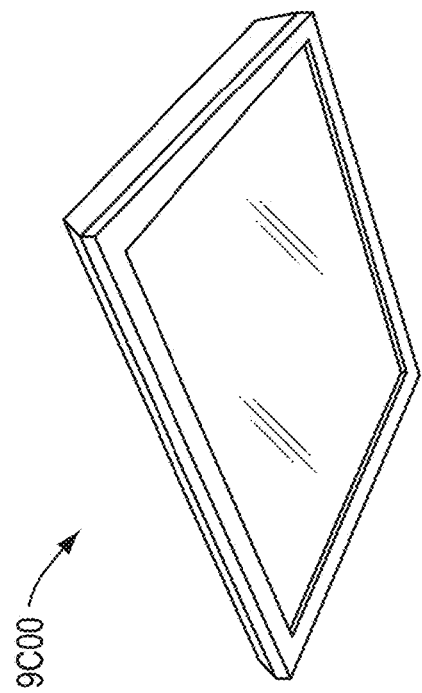
FIG. 9B through FIG. 9I present selections of troffers corresponding to various shapes, according to some embodiments.
Figure 9E:
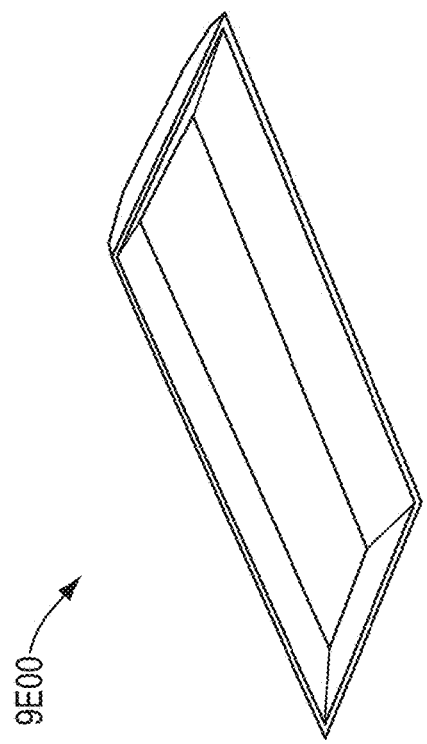
Figure 9B:
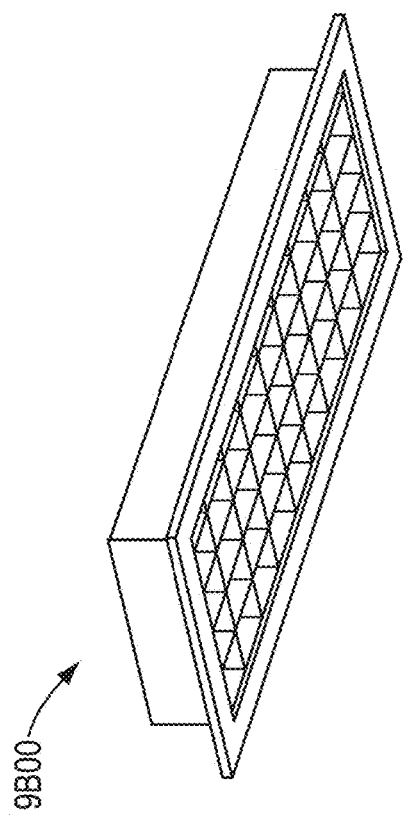
Figure 9D:
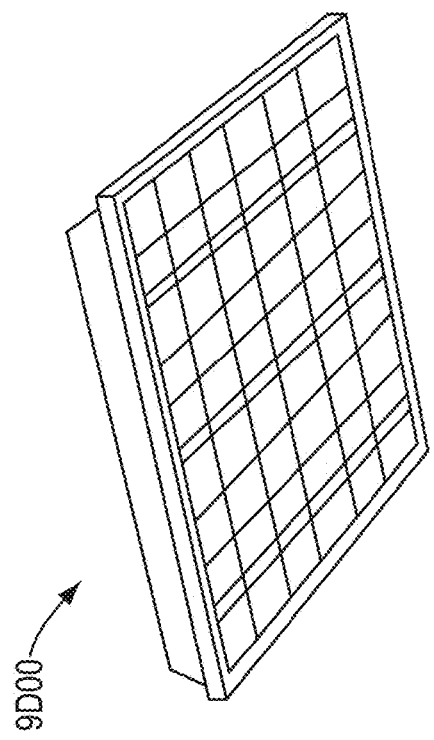
Figure 9F:
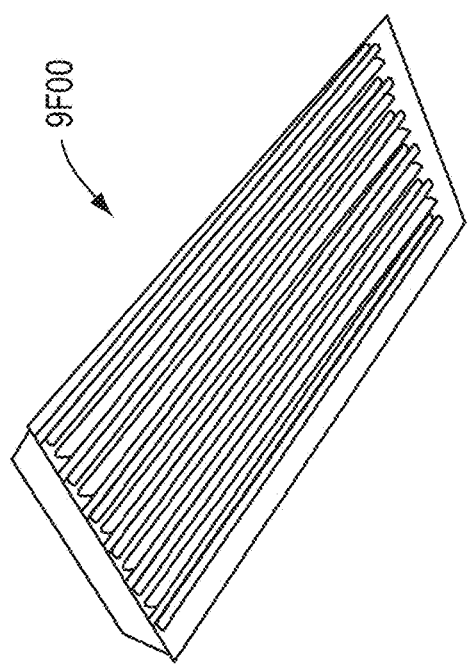
Figure 9G:
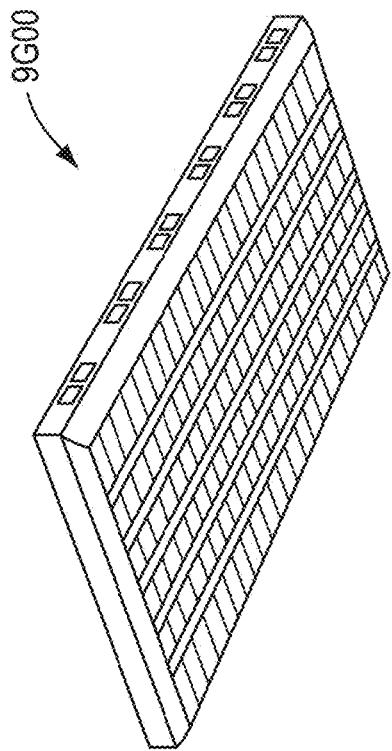
Figure 9I:
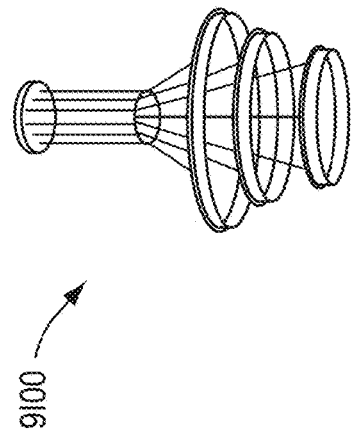
Figure 9H:
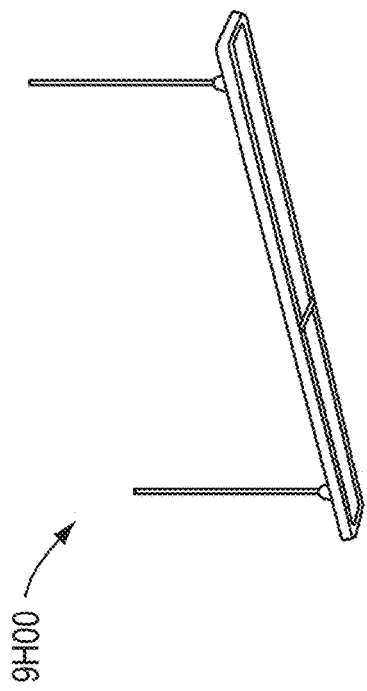

FIG. 9A presents a selection of lamp shapes corresponding to known-in-the-art standards. The aforementioned lamps are merely selected embodiments of lamps that conform to fit with any one or more of a set of mechanical and electrical standards. Table 1 gives standards (see "Designation") and corresponding characteristics.

TABLE 1

| Designation | Base Diameter (Crest of thread) | Name | IEC 60061-1 Standard Sheet |
|---|---|---|---|
| E05 | 05 mm | Lilliput Edison Screw (LES) | 7004-25 |
| E10 | 10 mm | Miniature Edison Screw (MES) | 7004-22 |
| E11 | 11 mm | Mini-Candelabra Edison Screw (mini-can) | (7004-06-1) |
| E12 | 12 mm | Candelabra Edison Screw (CES) | 7004-28 |
| E14 | 14 mm | Small Edison Screw (SES) | 7004-23 |
| E17 | 17 mm | Intermediate Edison Screw (IES) | 7004-26 |
| E26 | 26 mm | [Medium] (one-inch) Edison Screw (ES or MES) | 7004-21A-2 |
| E27 | 27 mm | [Medium] Edison Screw (ES) | 7004-21 |
| E29 | 29 mm | [Admedium] Edison Screw (ES) | |
| E39 | 39 mm | Single-contact (Mogul) Giant Edison Screw (GES) | 7004-24-A1 |
| E40 | 40 mm | (Mogul) Giant Edison Screw (GES) | 7004-24 |

Additionally, the base member of a lamp can be of any form factor configured to support electrical connections, which electrical connections can conform to any of a set of types or standards. For example Table 2 gives standards (see "Type") and corresponding characteristics, including mechanical spacing between a first pin (e.g., a power pin) and a second pin (e.g., a ground pin).

TABLE 2

| Type | Standard | Pin center to center | Pin Diameter | Usage |
|---|---|---|---|---|
| G4 | IEC 60061-1 (7004-72) | 4.0 mm | 0.65-0.75 mm | MR11 and other small halogens of 5/10/20 watt and 6/12 volt |
| GU4 | IEC 60061-1 (7004-108) | 4.0 mm | 0.95-1.05 mm | |
| GY4 | IEC 60061-1 (7004-72A) | 4.0 mm | 0.65-0.75 mm | |
| GZ4 | IEC 60061-1 (7004-64) | 4.0 mm | 0.95-1.05 mm | |
| G5 | IEC 60061-1 (7004-52-5) | 5 mm | | T4 and T5 fluorescent tubes |

TABLE 2-continued

| Type | Standard | Pin center to center | Pin Diameter | Usage |
|---|---|---|---|---|
| G5.3 | IEC 60061-1 (7004-73) | 5.33 mm | 1.47-1.65 mm | |
| G5.3-4.8 | IEC 60061-1 (7004-126-1) | | | |
| GU5.3 | IEC 60061-1 (7004-109) | 5.33 mm | 1.45-1.6 mm | |
| GX5.3 | IEC 60061-1 (7004-73A) | 5.33 mm | 1.45-1.6 mm | MR16 and other small halogens of 20/35/50 watt and 12/24 volt |
| GY5.3 | IEC 60061-1 (7004-73B) | 5.33 mm | | |
| G6.35 | IEC 60061-1 (7004-59) | 6.35 mm | 0.95-1.05 mm | |
| GX6.35 | IEC 60061-1 (7004-59) | 6.35 mm | 0.95-1.05 mm | |
| GY6.35 | IEC 60061-1 (7004-59) | 6.35 mm | 1.2-1.3 mm | Halogen 100 W 120 V |
| GZ6.35 | IEC 60061-1 (7004-59A) | 6.35 mm | 0.95-1.05 mm | |
| G8 | | 8.0 mm | | Halogen 100 W 120 V |
| GY8.6 | | 8.6 mm | | Halogen 100 W 120 V |
| G9 | IEC 60061-1 (7004-129) | 9.0 mm | | Halogen 120 V (US)/230 V (EU) |
| G9.5 | | 9.5 mm | 3.10-3.25 mm | Common for theatre use, several variants |
| GU10 | | 10 mm | | Twist-lock 120/230-volt MR16 halogen lighting of 35/50 watt, since mid-2000s |
| G12 | | 12.0 mm | 2.35 mm | Used in theatre and single-end metal halide lamps |
| G13 | | 12.7 mm | | T8 and T12 fluorescent tubes |
| G23 | | 23 mm | 2 mm | |
| GU24 | | 24 mm | | Twist-lock for self-ballasted compact fluorescents, since 2000s |
| G38 | | 38 mm | | Mostly used for high-wattage theatre lamps |
| GX53 | | 53 mm | | Twist-lock for puck-shaped under-cabinet compact fluorescents, since 2000s |

The list above is representative and should not be taken to include all the standards or form factors that may be utilized within embodiments described herein.

FIG. 9B through FIG. 9I present selections of troffers corresponding to various shapes (e.g., substantially square, substantially rectangular) and installation configurations (e.g., recessed, flush mounted, hanging, etc.). Combinations of the foregoing multi-track driver control system (see FIG. 7), and strings of LEDs in an intermixed physical arrangement (see FIG. 8) can be used with the exemplary troffers and/or with any sorts of general illumination fixtures.

Other luminaires such as suspended luminaires may emit light upward rather than downward, or may emit light in both directions.

FIG. 10A through FIG. 10I depict embodiments of the present disclosure in the form of lamp applications. In these lamp applications, one or more light emitting diodes are used in lamps and fixtures. Such lamps and fixtures include replacement and/or retro-fit directional lighting fixtures.

Figure 10A:
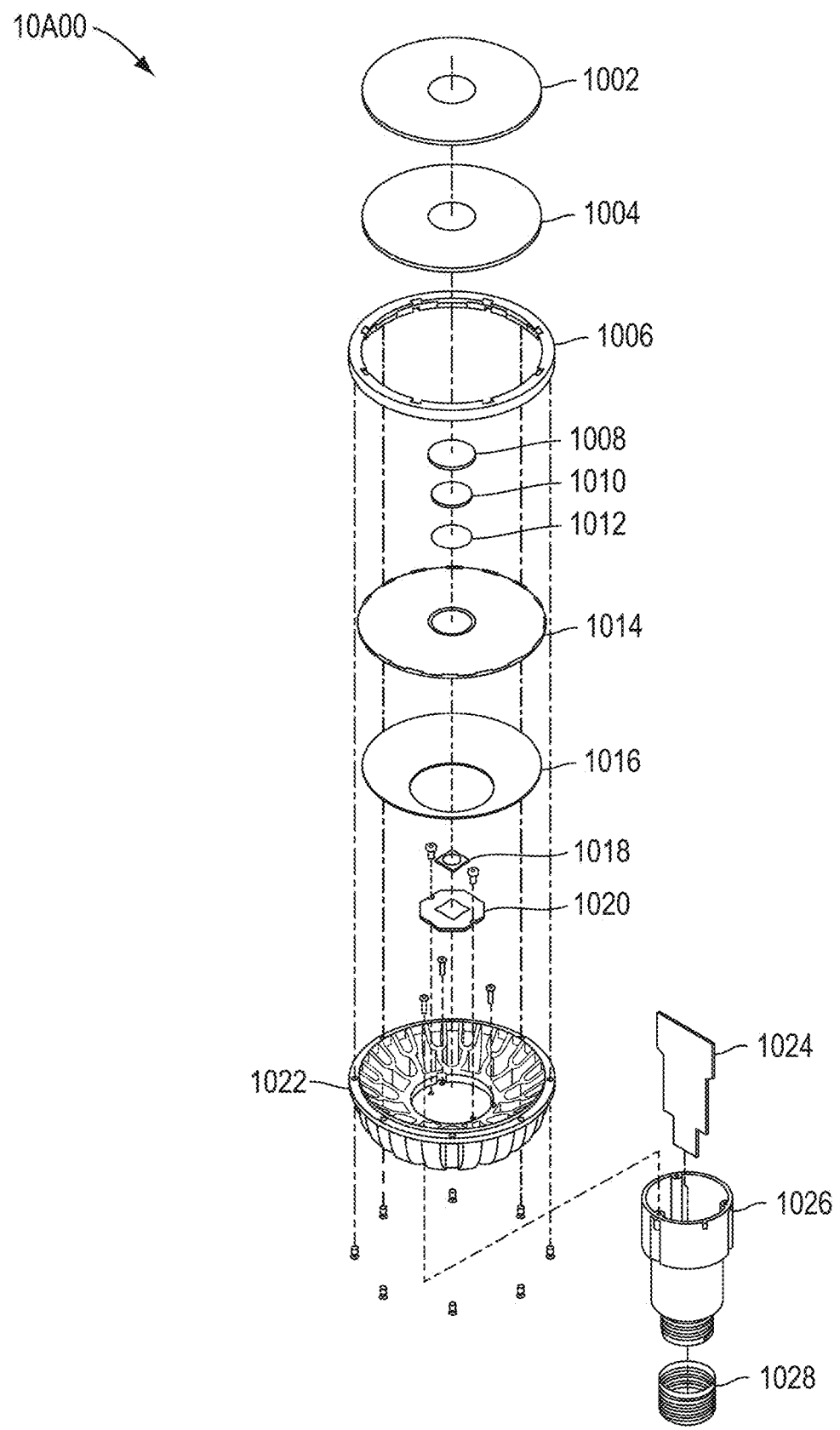
Figure 10C:
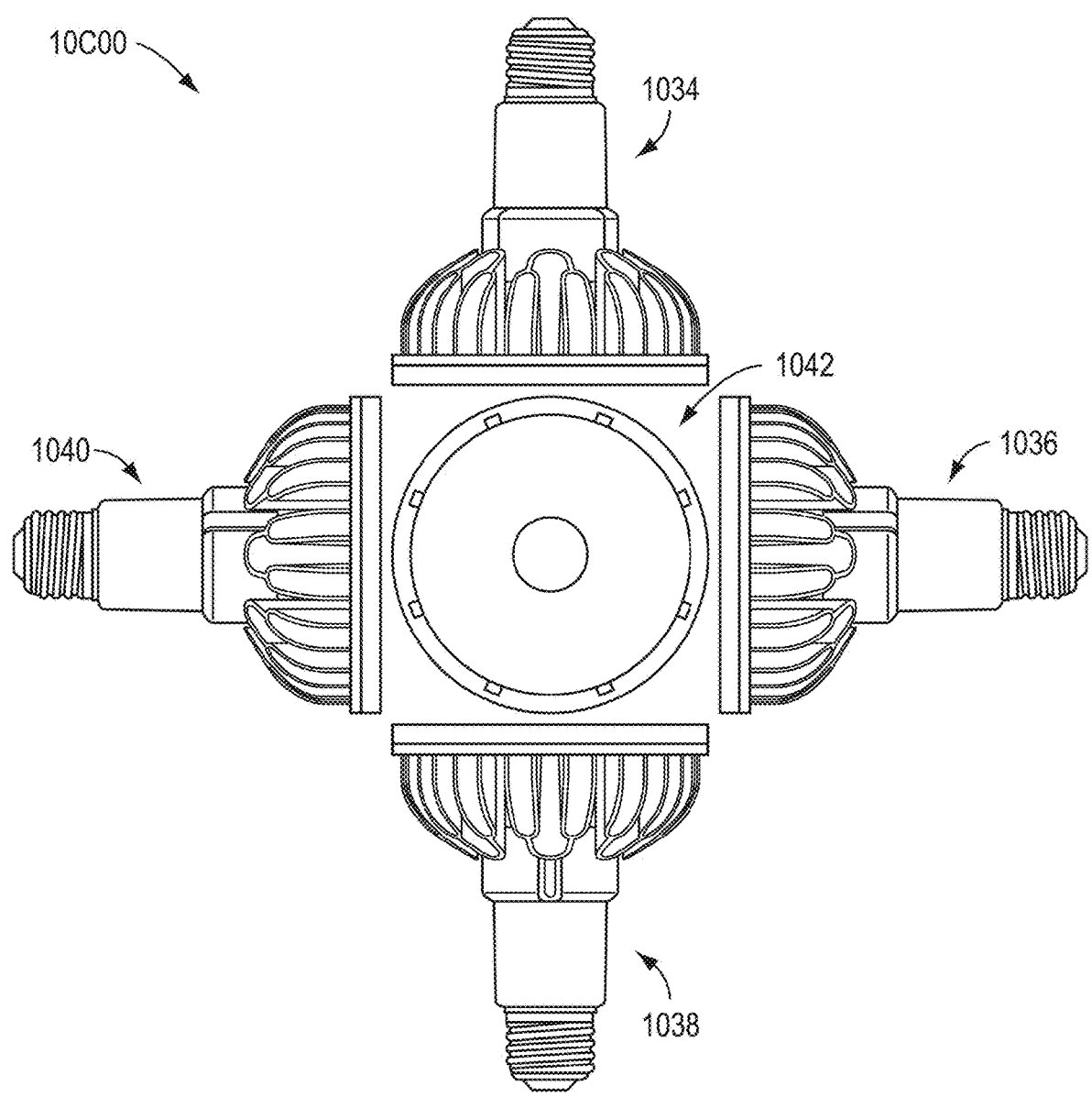
Figure 10E:
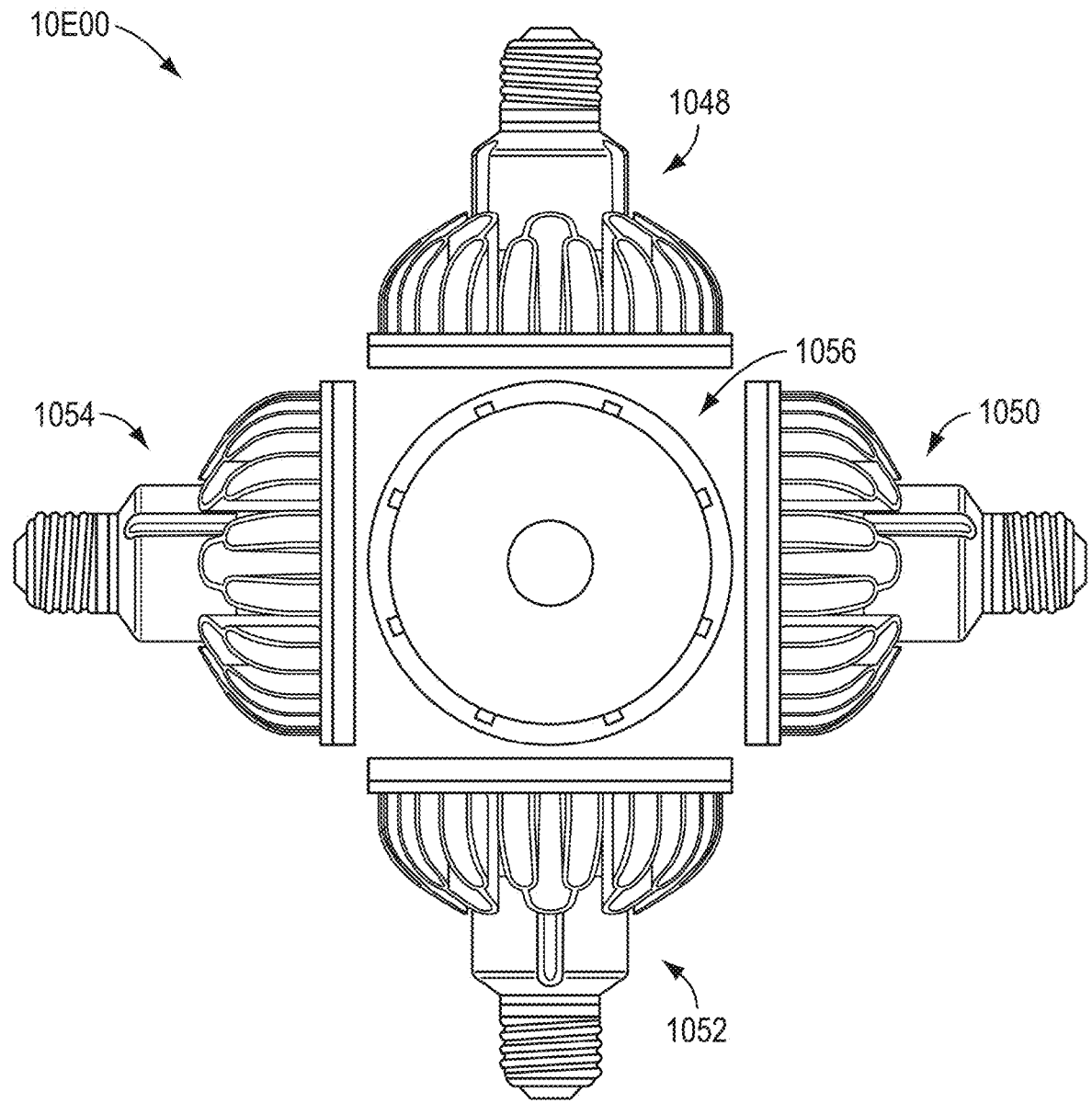
Figure 10G:
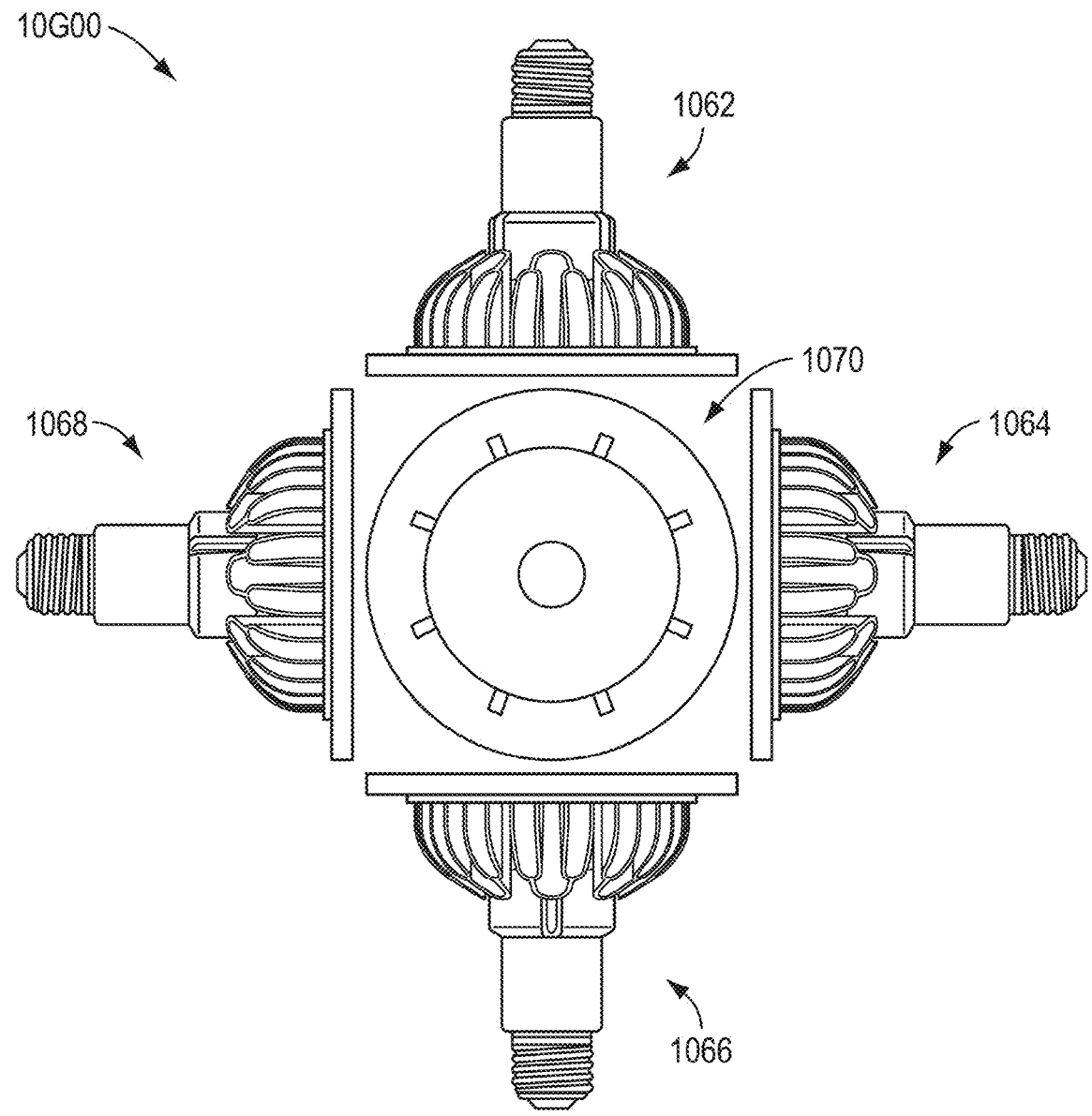
Figure 10I:
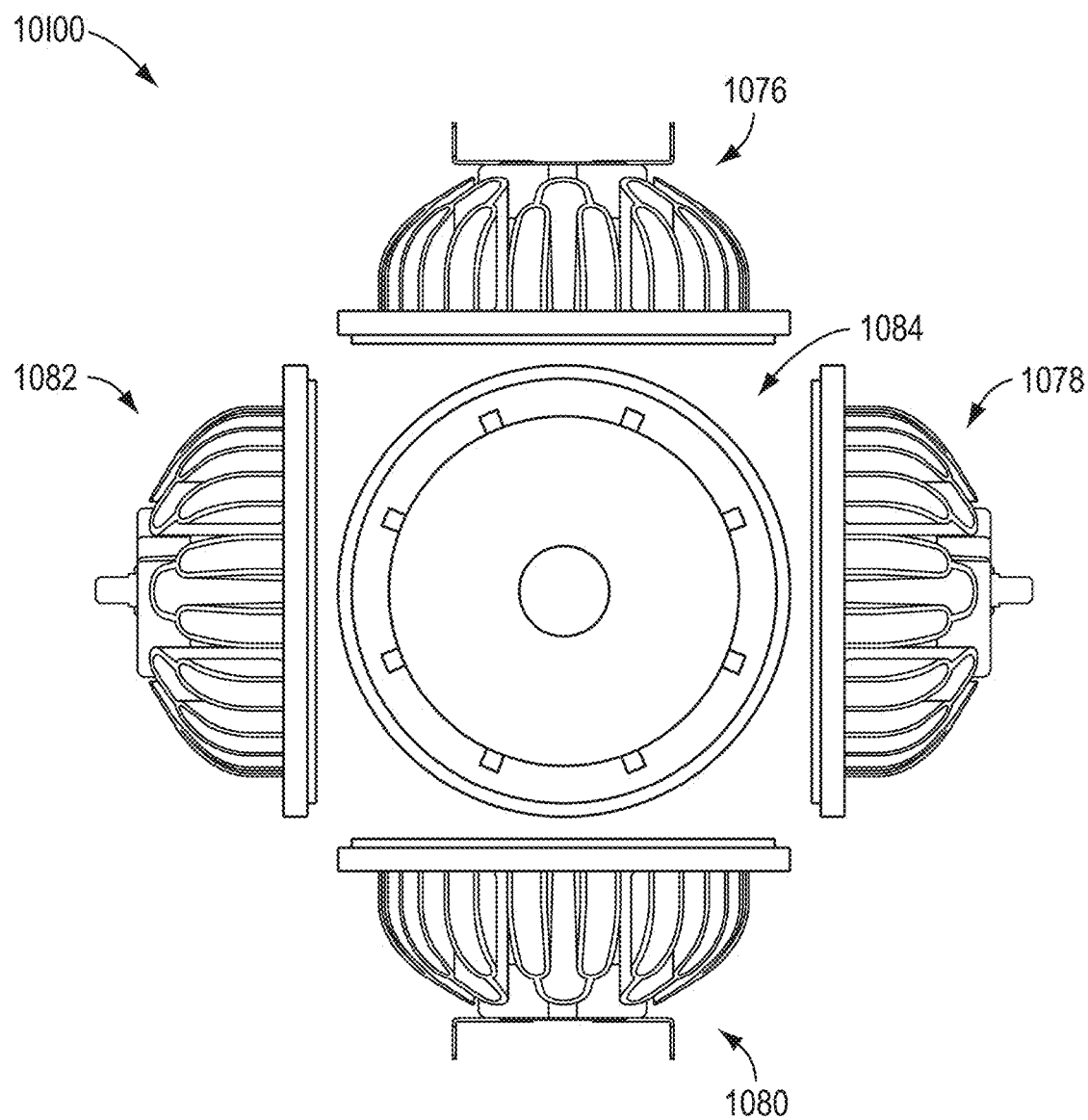

In some embodiments, aspects of the present disclosure can be used in an assembly. As shown in FIG. 10A, the assembly comprises:

a screw cap 1028
a driver housing 1026
a driver board 1024
a heatsink 1022
a metal-core printed circuit board 1020
an LED light source 1018
a dust shield 1016
a lens 1014
a reflector disc 1012
a magnet 1010
a magnet cap 1008
a trim ring 1006
a first accessory 1004
a second accessory 1002

The components of assembly 10A00 may be described in substantial detail. Some components are 'active components' and some are 'passive' components, and can be variously-described based on the particular component's impact to the overall design, and/or impact(s) to the objective optimization function. A component can be described using a CAD/CAM drawing or model, and the CAD/CAM model can be analyzed so as to extract figures of merit as may pertain to e particular component's impact to the overall design, and/or impact(s) to the objective optimization function. Strictly as one example, a CAD/CAM model of a trim ring is provided in a model corresponding to the drawing of FIG. 10A2.

The components of the assembly 10B100 and assembly 10B200 can be fitted together to form a lamp. FIG. 10B1 depicts a perspective view 1030 and FIG. 10B2 depicts a top view 1032 of such a lamp. As shown in FIG. 10B1 and FIG. 10B2, the lamp 10B100 and 10B200 comports to a form factor known as PAR30L. The PAR30L form factor is further depicted by the principal views (e.g., left 1040, right 1036, back 1034, front 1038 and top 1042) given in array 10000 of FIG. 10C.

The components of the assembly 10D100 and assembly 10D200 can be fitted together to form a lamp. FIG. 10D1 depicts a perspective view 1044 and FIG. 10D2 depicts a top view 1046 of such a lamp. As shown in FIG. 10D1 and in FIG. 10D2, the lamp 10D100 and 10D200 comports to a form factor known as PAR30S. The PAR30S form factor is further depicted by the principal views (e.g., left 1054, right 1050, back 1048, front 1052 and top 1056) given in array 10E00 of FIG. 10E.

The components of the assembly 10A00 can be fitted together to form a lamp. FIG. 10F1 depicts a perspective view 1058 and FIG. 10F2 depicts a top view 1060 of such a lamp. As shown in FIG. 10F1 and FIG. 10F2, the lamp 10F100 and 10F200 comports to a form factor known as PAR38. The PAR38 form factor is further depicted by the principal views (e.g., left 1068, right 1064, back 1062, front 1066 and top 1070) given in array 10G00 of FIG. 10G.

The components of the assembly 10A00 can be fitted together to form a lamp. FIG. 10H1 depicts a perspective view 1072 and FIG. 10H2 depicts a top view 1074 of such a lamp. As shown in FIG. 10H1 and FIG. 10H2, the lamp 10H100 and 10H200 comports to a form factor known as PAR111. The PAR111 form factor is further depicted by the principal views (e.g., left 1082, right 1078, back 1076, front 1080 and top 1084) given in array 10I00 of FIG. 10I.

In addition to uses of the aforementioned lamps and lamp shapes, filters or so-called 'circadian phosphors' can be employed.

Using Filters or Phosphors

Various implementations can be considered to alter an SPD's impact on the circadian system. As discussed above, it is possible to use a multiple-channel system including violet-pump and blue-pump LEDs and to balance the contribution of both channels. Besides, it is possible to physically block a given spectral range (such as the blue, cyan or violet region)—for instance by using absorbing or reflecting filters which may be fixed or moving. Filters offer the advantage that a substantial amount of light (or even all the light) can be blocked in a given spectral range, which may be of importance. For instance, it may be desirable to block nearly all the light in the blue-cyan range (or in a more specific range) to obtain a very low circadian stimulation—this is because standard spectra (such as a dimmed filament lamp) still have a fair amount of circadian stimulation. Such filters may for instance be dichroic reflective filters or absorbing filters including dye filters in a matrix (glass, plastic or other)

Another option, however, is to use a light-converting material in the system with a carefully chosen absorption range. For instance, one may include a phosphor which absorbs blue light and down-converts it to green or red light. This approach may be desirable because it enables one to remove a substantial amount of light in the absorption range like a blocking approach would, but with higher system efficiency since the radiation is converted to another wavelength rather than merely being blocked. For simplicity, we call this phosphor the 'circadian phosphor', since its absorption has an impact on the circadian action of the light source.

Figure 11A:
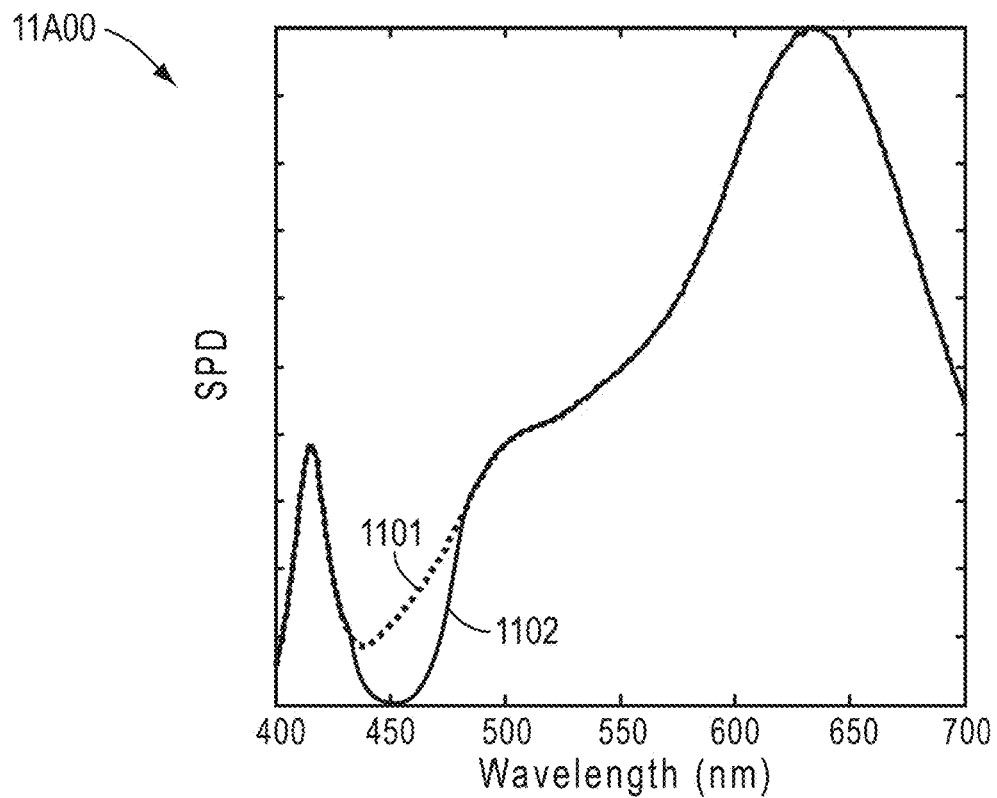
FIG. 11A shows an initial SPD of a LED white light source, and a filtered SPD after blue light is removed, according to some embodiments.
Figure 11B:
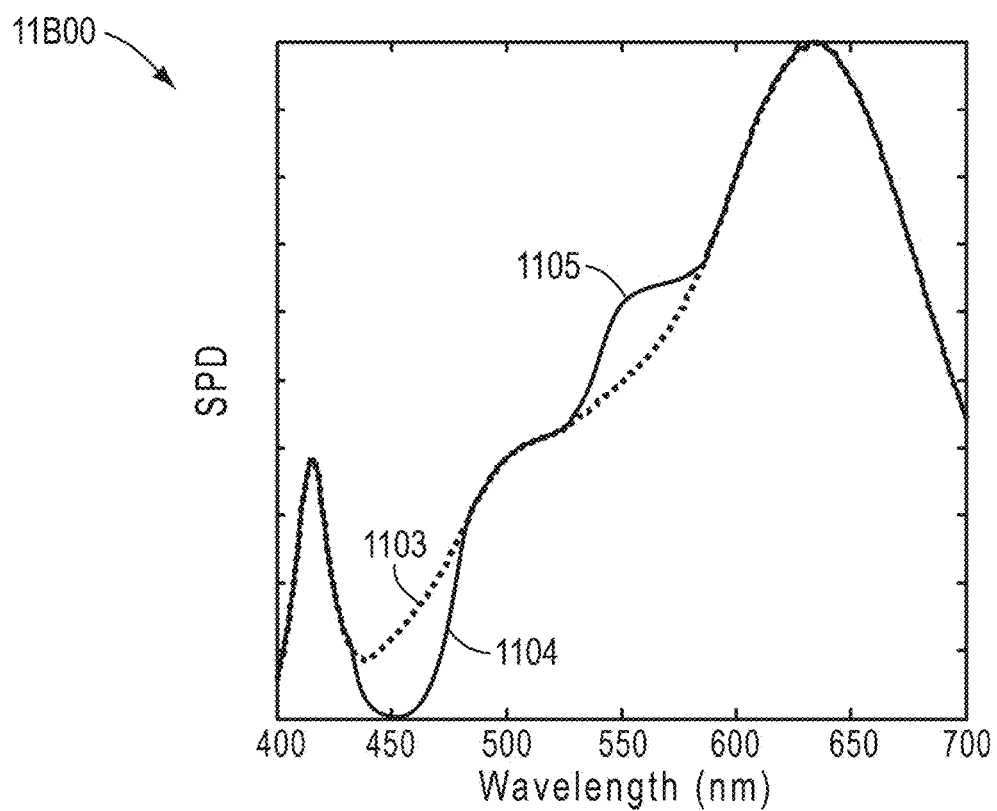
FIG. 11B shows an initial SPD of a LED white light source and a converted SPD after blue light is absorbed by a phosphor and converted to yellow light, according to some embodiments.

FIG. 11A and FIG. 11B contrasts the two approaches. FIG. 11A shows the initial SPD of a white LED source 1101, and the filtered SPD 1102 after blue light is blocked by a filter. The filtered SPD 1102 can be used in many embodiments, as it has a low amount of blue light, which can reduce disruption of the circadian system; furthermore the width and general shape of the filter may be designed to control this effect. However, filtering induces a penalty in efficiency because the filtered light is lost.

FIG. 11B shows the initial SPD of a white LED source 1103, and the converted SPD 1104 after blue light is absorbed by a "circadian phosphor" and converted to yellow light 1105. In this case, the same desirable effect on the circadian system is obtained, but the impact on efficiency is lessened thanks to the conversion of blue light. Here again, various aspects of the approach can be controlled through design, such as the position and amplitude of the absorption dip, which absorption dip can be controlled through the choice and amount of phosphor, and the position and amplitude of the luminescence. For instance, the absorption may be chosen to substantially block blue light but to allow some violet light transmission.

The circadian phosphor may be static, in which case the emitted SPD does not vary, or it may be on a moving part in order to control the SPD dynamically. The moving part may be a plate containing the phosphor, which can be moved mechanically in and out of the path of light emission of the system.

In FIG. 11A and FIG. 11B, the embodiments are designed to remove light in the range 440 nm to 460 nm. By choosing other filters or other phosphors this range can be tuned—for instance the range 450 nm to 480 nm, or another range, can be targeted and the spectral power in the range reduced. In some embodiments, a specific circadian action spectrum is assumed and the SPD is designed to have a low amount of light in the range where the action spectrum is high.

In yet another embodiment, the circadian phosphor shows a saturation behavior: it absorbs light at low flux, but absorption saturates at high flux. Such an approach is illustrated in FIG. 12 through FIG. 14.

Figure 12:
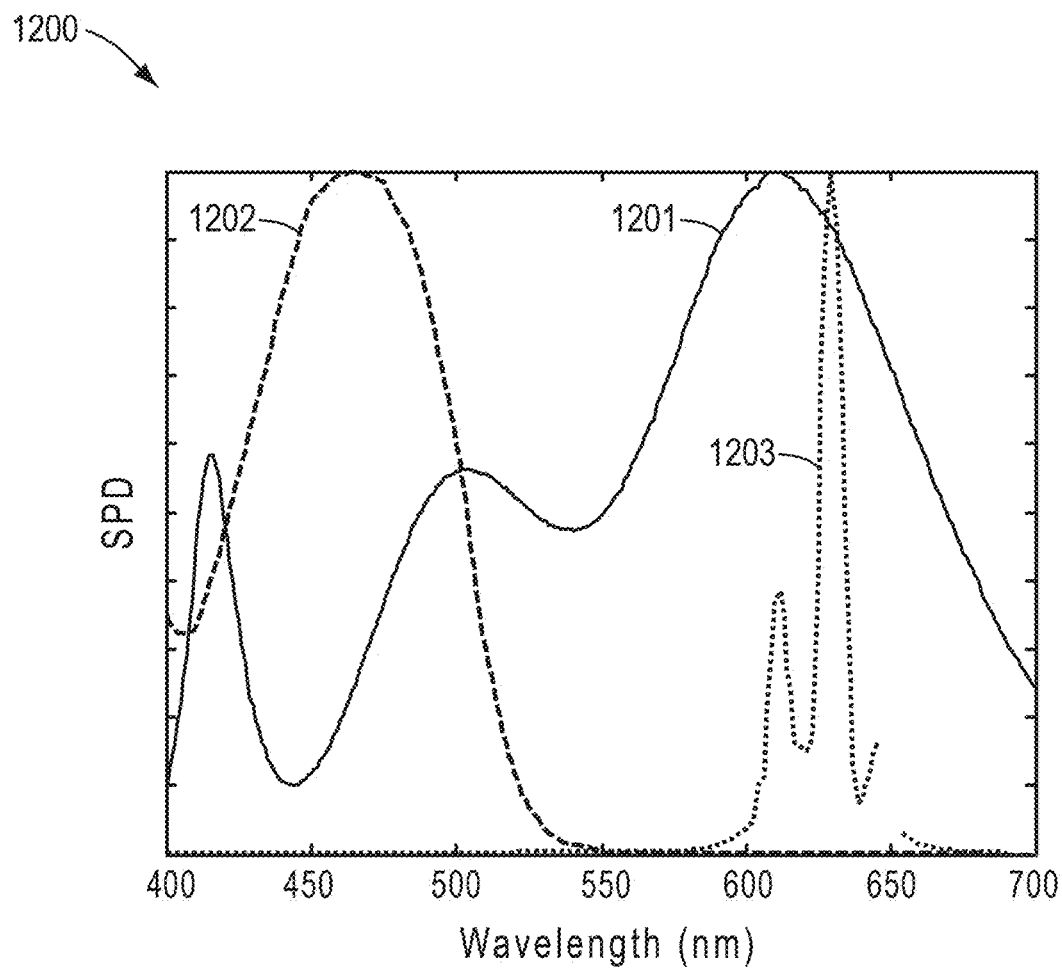
FIG. 12 shows an emission spectrum of a LED white light source with a CCT of 3000K and a CRI of about 90, and the emission and absorption spectra of a saturable red phosphor, according to some embodiments.

FIG. 12 shows various spectra. Spectrum 1201 is an emission spectrum of a white LED source with a CCT of 3000K and a CRI of about 90. This spectrum may be obtained by combining a violet-pump LED and several phosphors (e.g., a green phosphor, a red phosphor and possibly a blue phosphor). Curve 1202 is the absorption spectrum of a saturable red circadian phosphor and curve 1203 is the corresponding luminescence spectrum. Spectrum 1202 and spectrum 1203 can be obtained, for instance, with Mn-doped phosphors such as $K_2[TiF_6]:Mn^{4+}$.

Figure 13:
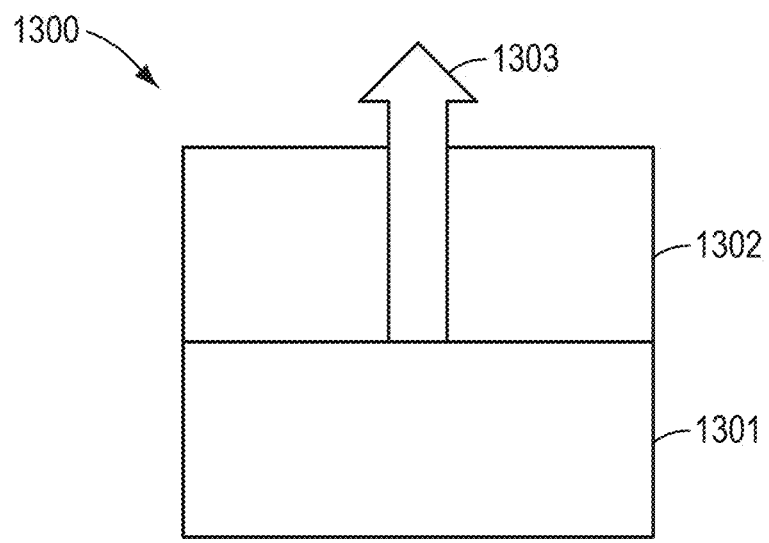
FIG. 13 shows a possible way to combine a LED white light source with such a saturable phosphor, according to some embodiments.

FIG. 13 shows a possible way to combine such a white LED source and such a saturable phosphor. In FIG. 13, the saturable circadian phosphor 1302 is placed above the LED source 1301 so that the white light emitted by the device 1303 can be absorbed by the circadian phosphor. Various other configurations are also possible—for instance, the circadian phosphor may be mixed with the phosphors of the white LED or may be in a remote configuration.

Figure 14A:
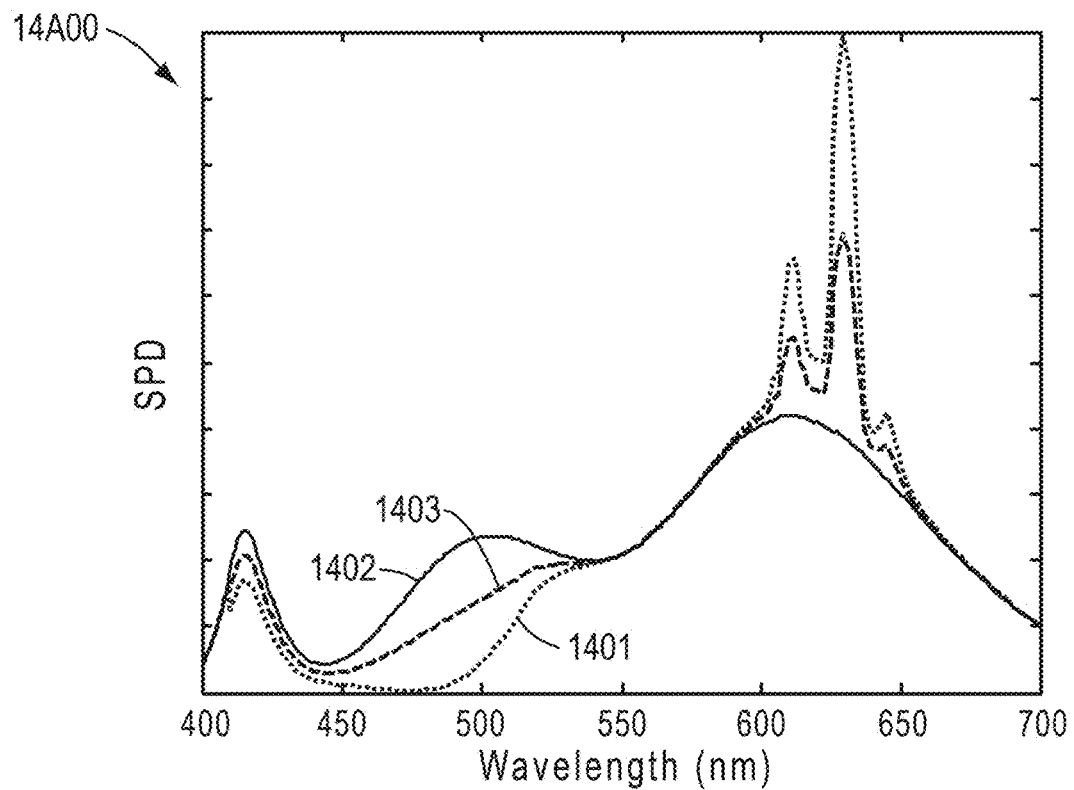
FIG. 14A and FIG. 14B show spectral and colorimetric properties, respectively, of a LED lighting system, according to some embodiments.
Figure 14B:
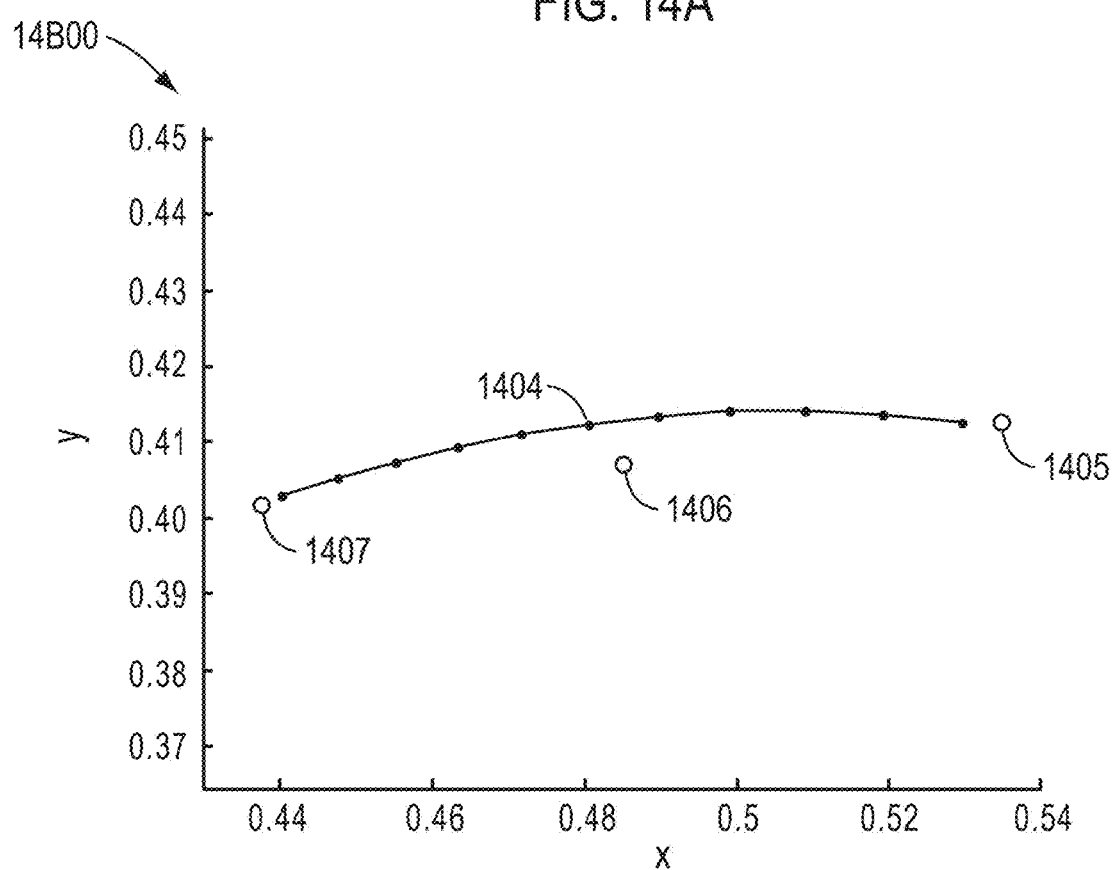

FIG. 14A and FIG. 14B show the resulting spectral and colorimetric properties of the system shown in FIG. 13. FIG. 14A shows the spectrum emitted by the system at various LED drive currents. At low drive current the saturable phosphor is not saturated and absorbs most of the light in its absorption range (e.g., blue-cyan light), resulting in spectrum 1401. At higher drive current the phosphor absorption is partially saturated and part of the blue-cyan light is transmitted, resulting in spectrum 1402. At even higher drive current the phosphor absorption is fully saturated, and the original spectrum of the white LED 1403 is emitted with very little perturbation from the circadian phosphor. FIG. 14B shows the corresponding chromaticity in (x, y) space for each drive current. At low drive current the CCT is about 2000K 1405, at higher drive current it is about 2500K 1406 and at the highest drive current it is about 3000K 1407. In all cases, the chromaticity is close to the Planckian locus 1404.

The embodiments of FIG. 12 through FIG. 14 achieve several desirable properties. At high drive current (e.g., see curve 1402), the embodiments behave like a conventional halogen retrofit with a high CRI (e.g., the circadian stimulation is 128% relative to standard illuminant A). As the current is reduced (e.g., see curves 1403 and 1401), the chromaticity shifts toward lower CCT (from 1407 to 1406 to 1405) thus emulating the behavior of a dimmed halogen or incandescent lamp. In addition, the spectrum is modified so that circadian stimulation decreases; at the lowest drive condition there is very little radiation in the range 440 nm to 490 nm (e.g., see curve 1401) and therefore very low stimulation of the circadian system (the circadian stimulation is only 8% relative to standard illuminant A).

As in other embodiments, the properties of the SPDs shown in FIG. 14A can be characterized by their relative fraction of power Fv in the range 400 nm to 440 nm and the fraction of power Fc in the range 440 nm to 500 nm. For SPD 1401, Fv=0.06 and Fc=0.01; for SPD 1402, Fv=0.08 and Fc=0.12. The value of Fc is especially low for SPD 1401, which can be associated with a very low circadian stimulation. This is in contrast to typical LED sources where a substantial fraction of power is in the range 440 nm to 500 nm (even for low-CCT sources with a CCT below 2700K).

While sources of varying CCT are known in the art and can be useful to modulate circadian stimulation, this embodiment has superior properties. The circadian stimulation is extremely low at low drive conditions: it is indeed lower than what is achieved with conventional LED sources, which employ a blue pump LED, or even by dimming of a conventional incandescent/halogen lamp. For example, a dimmed filament lamp emitting a blackbody spectrum with a CCT of 2000K still has a circadian stimulation of about 54% relative to illuminant A. Furthermore the present embodiment is 'passive' in that it doesn't require multiple channel drivers to modulate the spectrum. Therefore, such an embodiment may be integrated to a retrofit lamp or more generally a lighting system in absence of any advanced control circuits. In some such cases standard dimming switches provides the needed control.

In this embodiment, the presence of a violet pump is of importance since the violet light enables the chromaticity to be near-Planckian at low drive current, even in the absence of blue-cyan light.

Various aspects of this embodiment can be advantageously controlled. For instance, the optical properties of the pump LED can be varied, and the selection of phosphors can be varied, and the relative loading of phosphors can be varied to accomplish an optimization objective. The optimization criteria may include the CRI of the source at various dimming levels, its chromaticity and various dimming level, and metrics related to its circadian impact at various dimming levels. Strictly as one example, optimization criteria may include aspects of an integrated circadian action spectrum. The loading of the circadian phosphor can be chosen so that its saturation occurs at a desired drive, such as, for instance, 10% dimming. In other embodiments, more than one circadian phosphor is used.

In other embodiment, the white LED is obtained by multiple LED chips, such as uses of a violet LED, a green LED and a red LED rather than a phosphor-converted LED. In other embodiments, the chromaticity of the source does not follow the Planckian locus—it may for instance be below the Planckian locus, which is sometimes associated with a preferred perception as already discussed.

Embodiments may be integrated to various systems. This includes lighting systems (e.g., lamps, troffers and others) and non-lighting systems (e.g., display applications).

FIG. 15A1 through FIG. 15I depict embodiments of the present disclosure as can be applied toward lighting applications. In these embodiments, as shown in FIGS. 15A1-15A3, one or more light-emitting diodes 15A10, as taught by this disclosure, can be mounted on a submount or package to provide an electrical interconnection. As shown in FIGS. 15B1-15B3 a submount or package can be a ceramic, oxide, nitride, semiconductor, metal, or combination thereof that includes an electrical interconnection capability 15A20 for the various LEDs. The submount or package can be mounted to a heatsink member 15B50 via a thermal interface. The LEDs can be configured to produce a desired emission spectrum, either by mixing primary emissions from various LEDs, or by having the LEDs photo-excite wavelength down-conversion materials such as phosphors, semiconductors, or semiconductor nanoparticles ("quantum dots"), or a combination of any of the foregoing.

The total light emitting surface (LES) of the LEDs and any down-conversion materials can form a light source 15A30. One or more light sources can be interconnected into an array 15B20, which in turn is in electrical contact with connectors 15B10 and brought into an assembly 15B30. One or more lens elements 15B40 can be optically coupled to the light source. The lens design and properties can be selected so that the desired directional beam pattern for a lighting product is achieved for a given LES. The directional lighting product may be an LED module, a retrofit lamp 15B70, or a lighting fixture 15C30. In the case of a retrofit lamp, an electronic driver can be provided with a surrounding member 15B60, the driver to condition electrical power from an external source to render it suitable for the LED light source. The driver can be integrated into the retrofit lamp. In the case of a fixture, an electronic driver is provided which conditions electrical power from an external source to make it suitable for the LED light source, with the driver either integrated into the fixture or provided externally to the fixture. In the case of a module, an electronic driver can be provided to condition electrical power from an external source to render it suitable for the LED light source, with the driver either integrated into the module or provided externally to the module. Examples of suitable external power sources include mains AC (e.g., 120 Vrms AC or 240 Vrms AC), low-voltage AC (e.g., 12 VAC), and low-voltage DC (e.g., 12 VDC). In the case of retrofit lamps, the entire lighting product may be designed to fit standard form factors (e.g., ANSI form factors). Examples of retrofit lamp products include LED-based MR16, PAR16, PAR20, PAR30, PAR38, BR30, A19 and various other lamp types. Examples of fixtures include replacements for halogen-based and ceramic metal halide-based directional lighting fixtures.

In some embodiments, the present disclosure can be applied to non-directional lighting applications. In these embodiments, one or more light-emitting diodes (LEDs), as taught by the disclosure, can be mounted on a submount or package to provide an electrical interconnection. The submount or package can be, for example, a ceramic, oxide, nitride, semiconductor, metal, or combination of any of the foregoing that includes electrical interconnection capability for the various LEDs. The submount or package can be mounted to a heatsink member via a thermal interface. The LEDs can be configured to produce a desired emission spectrum, either by mixing primary emissions from various LEDs, or by having the LEDs photo-excite wavelength down-conversion materials such as phosphors, semiconductors, or semiconductor nanoparticles ("quantum dots"), or a combination thereof. The LEDs can be distributed to provide a desired shape of the light source. For example, one common shape is a linear light source for replacement of conventional fluorescent linear tube lamps. One or more optical elements can be coupled to the LEDs to provide a desired non-directional light distribution. The non-directional lighting product may be an LED module, a retrofit lamp, or a lighting fixture. In the case of a retrofit lamp, an electronic driver can be provided to condition electrical power from an external source to render it suitable for the LED light source, with the driver integrated into the retrofit lamp. In the case of a fixture, an electronic driver is provided to condition electrical power from an external source to render it suitable for the LED light source, with the driver either integrated into the fixture or provided externally to the fixture. In the case of a module, an electronic driver can be provided to condition electrical power from an external source to render it suitable for the LED light source, with the driver either integrated into the module or provided externally to the module. Examples of external power sources include mains AC (e.g., 120 Vrms AC or 240 Vrms AC), low-voltage AC (e.g., 12 VAC), and low-voltage DC (e.g., 12 VDC). In the case of retrofit lamps, the entire lighting product may be designed to fit standard form factors (e.g., ANSI form factors). Examples of non-directional lighting products are shown in FIG. 15C1, FIG. 15C2, and FIG. 15C3. Such a lighting fixture can include replacements for fluorescent-based troffer luminaires 15C30. In this embodiment, LEDs are mechanically secured into a package 15C10, and multiple packages are arranged into a suitable shape such as linear array 15C20.

Some embodiments of the present disclosure can be applied to backlighting for flat panel display applications. In these embodiments, one or more light-emitting diodes (LEDs), as taught by this disclosure, can be mounted on a submount or package to provide an electrical interconnection. The submount or package can be a ceramic, oxide, nitride, semiconductor, metal, or combination of any of the foregoing that include electrical interconnection capability for the various LEDs. The submount or package can be mounted to a heatsink member via a thermal interface. The LEDs can be configured to produce a desired emission spectrum, either by mixing primary emissions from various LEDs, or by having the LEDs photo-excite wavelength down-conversion materials such as phosphors, semiconductors, or semiconductor nanoparticles ("quantum dots"), or a combination of any of the foregoing. The LEDs can be distributed to provide a desired shape of the light source. One common shape is a linear light source. The light source can be optically coupled to a lightguide for the backlight. This can be achieved by coupling at the edge of the lightguide (edge-lit), or by coupling light from behind the lightguide (direct-lit). The lightguide distributes light uniformly toward a controllable display such as a liquid crystal display (LCD) panel. The display converts the LED light into desired images based on electrical control of light transmission and its color. One way to control the color is by use of filters (e.g., color filter substrate 15D40). Alternatively, multiple LEDs may be used and driven in pulsed mode to sequence the desired primary emission colors (e.g., using a red LED 15D30, a green LED 15D10, and a blue LED 15D20). Optional brightness-enhancing films may be included in the backlight "stack". The brightness-enhancing films narrow the flat panel display emission to increase brightness at the expense of the observer-viewing angle. An electronic driver can be provided to condition electrical power from an external source to render it suitable for the LED light source for backlighting, including any color sequencing or brightness variation per LED location (e.g., one-dimensional or two-dimensional dimming). Examples of external power sources include mains AC (e.g., 120 Vrms AC or 240 Vrms AC), low-voltage AC (e.g., 12 VAC), and low-voltage DC (e.g., 12 VDC). Examples of backlighting products are shown in FIG. 15D1, FIG. 15D2, FIG. 15E1 and FIG. 15E2.

Some embodiments of the present disclosure can be applied to automotive forward lighting applications, as shown in FIGS. 15F1-15F (e.g., see the example of an automotive forward lighting product 15F30). In these embodiments, one or more light-emitting diodes (LEDs) can be mounted on a submount or on a rigid or semi-rigid package 15F10 to provide an electrical interconnection. The submount or package can be a ceramic, oxide, nitride, semiconductor, metal, or combination thereof, that include electrical interconnection capability for the various LEDs. The submount or package can be mounted to a heatsink member via a thermal interface. The LEDs can be configured to produce a desired emission spectrum, either by mixing primary emission from various LEDs, or by having the LEDs photo-excite wavelength down-conversion materials such as phosphors, semiconductors, or semiconductor nanoparticles ("quantum dots"), or a combination of any of the foregoing. The total light emitting surface (LES) of the LEDs and any down-conversion materials form a light source. One or more lens elements 15F20 can be optically coupled to the light source. The lens design and properties can be selected to produce a desired directional beam pattern for an automotive forward lighting application for a given LED. An electronic driver can be provided to condition electrical power from an external source to render it suitable for the LED light source. Power sources for automotive applications include low-voltage DC (e.g., 12 VDC). An LED light source may perform a high-beam function, a low-beam function, a side-beam function, or any combination thereof.

Certain embodiments of the present disclosure can be applied to digital imaging applications such as illumination for mobile phone and digital still cameras (e.g., see FIGS. 15G1-15G4). In these embodiments, one or more light-emitting diodes (LEDs), as taught by the disclosure, can be mounted on a submount or package 15G10 to provide an electrical interconnection. The submount or package can be, for example, a ceramic, oxide, nitride, semiconductor, metal, or combination of any of the foregoing that include electrical interconnection capability for the various LEDs. The submount or package can be mounted to a circuit board member and fitted with or into a mounting package 15G20. The LEDs can be configured to produce a desired emission spectrum, either by mixing primary emission from various LEDs, or by having the LEDs photo-excite wavelength down-conversion materials such as phosphors, semiconductors, or semiconductor nanoparticles ("quantum dots"), or a combination thereof. The total light emitting surface (LES) of the LEDs and any down-conversion materials form a light source. One or more lens elements can be optically coupled to the light source. The lens design and properties can be selected so that the desired directional beam pattern for an imaging application is achieved for a given LES. An electronic driver can be provided to condition electrical power from an external source to render it suitable for the LED light source. Examples of suitable external power sources for imaging applications include low-voltage DC (e.g., 5 VDC). An LED light source may perform a low-intensity function 15G30, a high-intensity function 15G40, or any combination thereof.

Figure 15H:
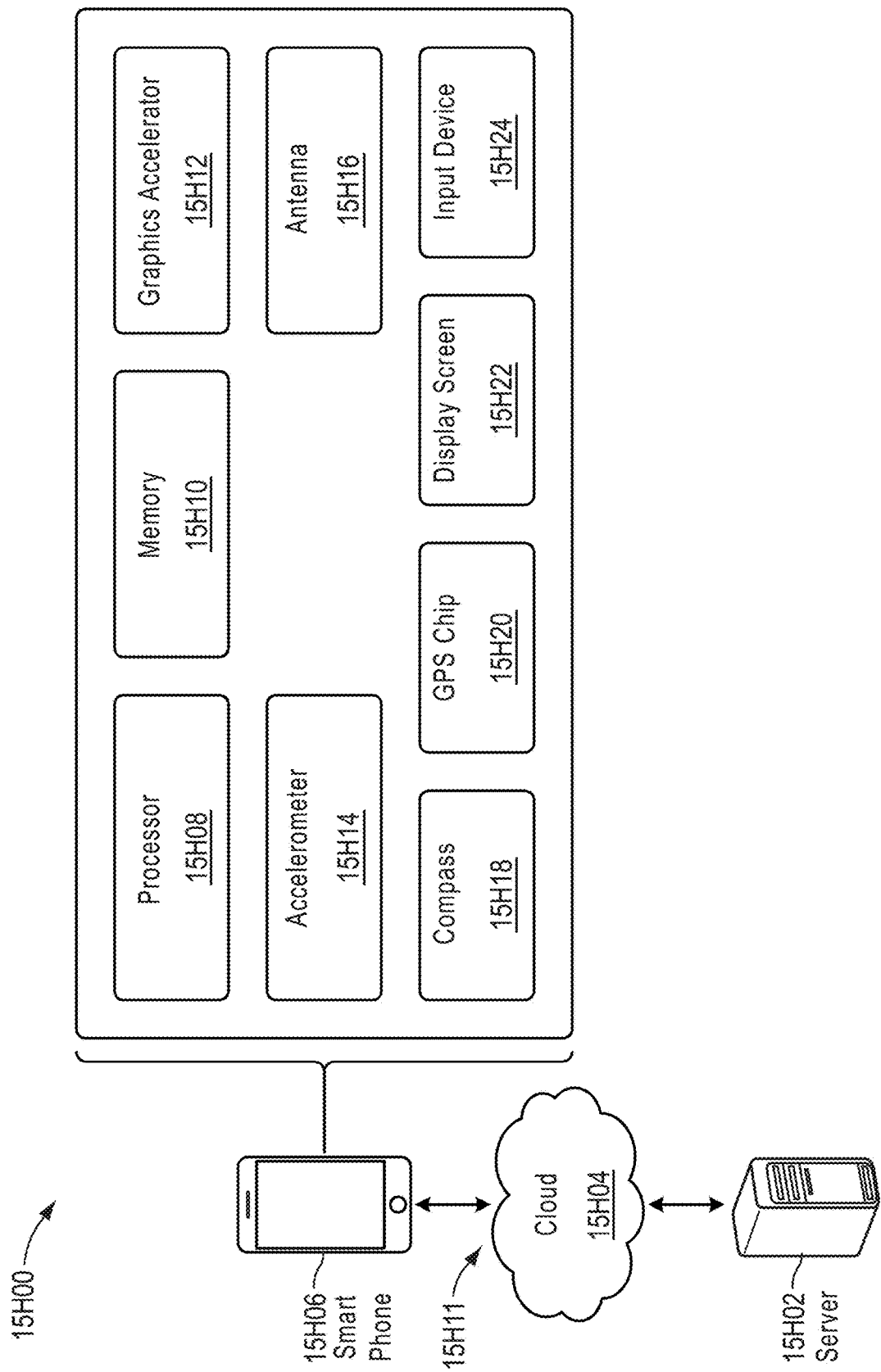

Some embodiments of the present disclosure can be applied to mobile terminal applications. FIG. 15H is a diagram illustrating a mobile terminal (see smart phone architecture 15H00). As shown, the smart phone 15H06 includes a housing, display screen, and interface device, which may include a button, microphone, and/or touch screen. In certain embodiments, a phone has a high resolution camera device, which can be used in various modes. An example of a smart phone can be an iPhone from Apple Inc. of Cupertino, Calif. Alternatively, a smart phone can be a Galaxy from Samsung, or others.

In an example, the smart phone may include one or more of the following features (which are found in an iPhone 4 from Apple Inc., although there can be variations), see www.apple.com:

- GSM model: UMTS/HSDPA/HSUPA (850, 900, 1900, 2100 MHz); GSM/EDGE (850, 900, 1800, 1900 MHz)
- CDMA model: CDMA EV-DO Rev. A (800, 1900 MHz)
- 802.11b/g/n Wi-Fi (802.11n 2.4 GHz only)
- Bluetooth 2.1+EDR wireless technology
- Assisted GPS
- Digital compass
- Wi-Fi
- Cellular
- Retina display
- 3.5-inch (diagonal) widescreen multi-touch display
- 800:1 contrast ratio (typical)
- 500 cd/m2 max brightness (typical)
- Fingerprint-resistant oleophobic coating on front and back
- Support for display of multiple languages and characters simultaneously
- 5-megapixel iSight camera
- Video recording, HD (720p) up to 30 frames per second with audio
- VGA-quality photos and video at up to 30 frames per second with the front camera
- Tap to focus video or still images
- LED flash
- Photo and video geotagging
- Built-in rechargeable lithium-ion battery
- Charging via USB to computer system or power adapter
- Talk time: Up to 20 hours on 3G, up to 14 hours on 2G (GSM)
- Standby time: Up to 300 hours
- Internet use: Up to 6 hours on 3G, up to 10 hours on Wi-Fi
- Video playback: Up to 10 hours
- Audio playback: Up to 40 hours
- Frequency response: 20 Hz to 22,000 Hz
- Audio formats supported: AAC (8 to 320 Kbps), protected AAC (from iTunes Store), HE-AAC, MP3 (8 to 320 Kbps), MP3 VBR, audible (formats 2, 3, 4, audible enhanced audio, AAX, and AAX+), Apple lossless, AIFF, and WAV
- User-configurable maximum volume limit
- Video out support with Apple digital AV adapter or Apple VGA adapter; 576p and 480p with Apple component AV cable; 576i and 480i with Apple composite AV cable (cables sold separately)
- Video formats supported: H.264 video up to 1080p, 30 frames per second, main profile Level 3.1 with AAC-LC audio up to 160 Kbps, 48 kHz, stereo audio in .m4v, .mp4, and .mov file formats; MPEG-4 video up to 2.5 Mbps, 640 by 480 pixels, 30 frames per second, simple profile with AAC-LC audio up to 160 Kbps per channel, 48 kHz, stereo audio in .m4v, .mp4, and .mov file formats; motion JPEG (M-JPEG) up to 35 Mbps, 1280 by 1020 pixels, 30 frames per second, audio in ulaw, PCM stereo audio in .avi file format
- Three-axis gyro
- Accelerometer
- Proximity sensor
- Ambient light sensor, etc.

Embodiments of the present disclosure may be used with other electronic devices. Examples of suitable electronic devices include a portable electronic device such as a media player, a cellular phone, a personal data organizer, or the like. In such embodiments, a portable electronic device may include a combination of the functionalities of such devices. In addition, an electronic device may allow a user to connect to and communicate through the Internet or through other networks such as local or wide area networks. For example, a portable electronic device may allow a user to access the internet and to communicate using e-mail, text messaging, instant messaging, or using other forms of electronic communication. By way of example, the electronic device may be similar to an iPod having a display screen or an iPhone available from Apple Inc.

In certain embodiments, a device may be powered by one or more rechargeable and/or replaceable batteries. Such embodiments may be highly portable, allowing a user to carry the electronic device while traveling, working, exercising, and so forth. In this manner, and depending on the functionalities provided by the electronic device, a user may listen to music, play games or video, record video or take pictures, place and receive telephone calls, communicate with others, control other devices (e.g., via remote control and/or Bluetooth functionality), and so forth while moving freely with the device. In addition, the device may be sized such that it fits relatively easily into a pocket or the hand of the user. While certain embodiments of the present disclosure are described with respect to portable electronic devices, it should be noted that the presently disclosed techniques may be applicable to a wide array of other, less portable, electronic devices and systems that are configured to render graphical data such as a desktop computer.

As shown, FIG. 15H includes a system diagram with a smart phone that includes an LED according to an embodiment of the present disclosure. The smart phone 15H06 is configured to communicate with a server 15H02 in electronic communication with any forms of handheld electronic devices. Illustrative examples of such handheld electronic devices can include functional components such as a processor 15H08, memory 15H10, graphics accelerator 15H12, accelerometer 15H14, communications interface 15H11 (possibly including an antenna 15H16), compass 15H18, GPS chip 15H20, display screen 15H22, and an input device 15H24. Each device is not limited to the illustrated components. The components may be hardware, software or a combination of both.

In some examples, instructions can be input to the handheld electronic device through an input device 15H24 that instructs the processor 15H08 to execute functions in an electronic imaging application. One potential instruction can be to generate an abstract of a captured image of a portion of a human user. In that case the processor 15H08 instructs the communications interface 15H11 to communicate with the server 15H02 (e.g., possibly through or using a cloud 15H04) and transfer data (e.g., image data). The data is transferred by the communications interface 15H11 and either processed by the processor 15H08 immediately after image capture or stored in memory 15H10 for later use, or both. The processor 15H08 also receives information regarding the display screen's attributes, and can calculate the orientation of the device, e.g., using information from an accelerometer 15H14 and/or other external data such as compass headings from a compass 15H18, or GPS location from a GPS chip 15H20, and the processor then uses the information to determine an orientation in which to display the image depending upon the example.

The captured image can be rendered by the processor 15H08, by a graphics accelerator 15H12, or by a combination of the two. In some embodiments, the processor can be the graphics accelerator 15H12. The image can first be stored in memory 15H10 or, if available, the memory can be directly associated with the graphics accelerator 15H12. The methods described herein can be implemented by the processor 15H08, the graphics accelerator 15H12, or a combination of the two to create the image and related abstract. An image or abstract can be displayed on the display screen 15H22.

Figure 15I:
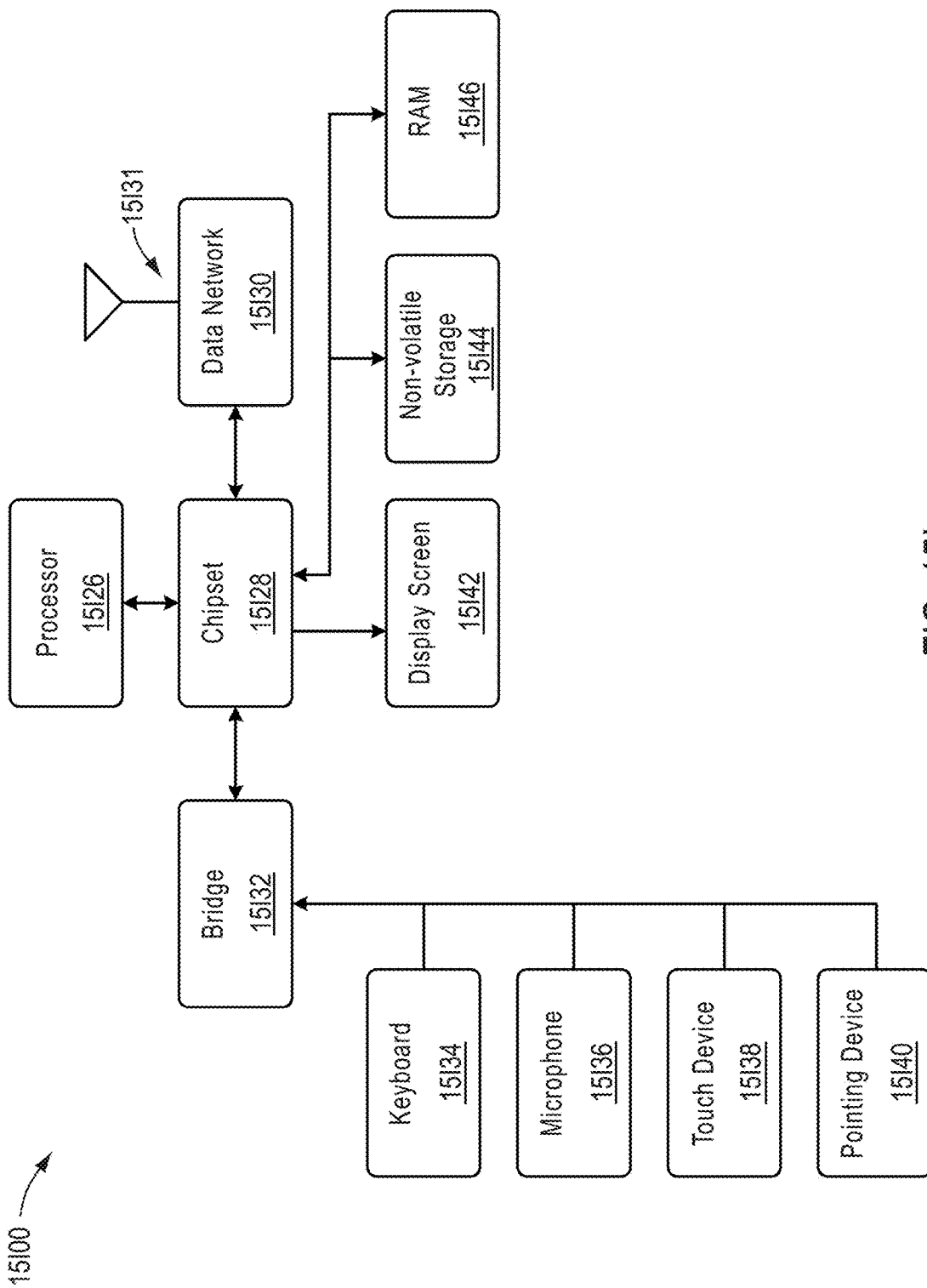

FIG. 15I depicts an interconnection of components in an electronic device 15I00. Examples of electronic devices include an enclosure or housing, a display, user input structures, and input/output connectors in addition to the aforementioned interconnection of components. The enclosure may be formed from plastic, metal, composite materials, or other suitable materials, or any combination thereof. The enclosure may protect the interior components of the electronic device from physical damage, and may also shield the interior components from electromagnetic interference (EMI).

The display may be a liquid crystal display (LCD), a light emitting diode (LED) based display, an organic light emitting diode (OLED) based display, or some other suitable display. In accordance with certain embodiments of the present disclosure, the display may display a user interface and various other images such as logos, avatars, photos, album art, and the like. Additionally, in certain embodiments, a display may include a touch screen through which a user may interact with the user interface. The display may also include various functions and/or system indicators to provide feedback to a user such as power status, call status, memory status, or the like. These indicators may be incorporated into the user interface displayed on the display.

In certain embodiments, one or more of the user input structures can be configured to control the device such as by controlling a mode of operation, an output level, an output type, etc. For instance, the user input structures may include a button to turn the device on or off. Further, the user input structures may allow a user to interact with the user interface on the display. Embodiments of the portable electronic device may include any number of user input structures including buttons, switches, a control pad, a scroll wheel, or any other suitable input structures. The user input structures may work with the user interface displayed on the device to control functions of the device and/or any interfaces or devices connected to or used by the device. For example, the user input structures may allow a user to navigate a displayed user interface or to return such a displayed user interface to a default or home screen.

Certain device may also include various input and output ports to allow connection of additional devices. For example, a port may be a headphone jack that provides for the connection of headphones. Additionally, a port may have both input and output capabilities to provide for the connection of a headset (e.g., a headphone and microphone combination). Embodiments of the present disclosure may include any number of input and/or output ports such as headphone and headset jacks, universal serial bus (USB) ports, IEEE-1394 ports, and AC and/or DC power connectors. Further, a device may use the input and output ports to connect to and send or receive data with any other device such as other portable electronic devices, personal computers, printers, or the like. For example, in one embodiment, the device may connect to a personal computer via an IEEE-1394 connection to send and receive data files such as media files.

The depiction of an electronic device 15I00 encompasses a smart phone system diagram according to an embodiment of the present disclosure. The depiction of an electronic device 15I00 illustrates computer hardware, software, and firmware that can be used to implement the disclosures above. The shown system includes a processor 15I26, which is representative of any number of physically and/or logically distinct resources capable of executing software, firmware, and hardware configured to perform identified computations. A processor 15I26 communicates with a chipset 15I28 that can control input to and output from processor 15I26. In this example, chipset 15I28 outputs information to display screen 15I42 and can read and write information to non-volatile storage 15I44, which can include magnetic media and solid state media, and/or other non-transitory media, for example. Chipset 15I28 can also read data from and write data to RAM 15I46. A bridge 15I32 for interfacing with a variety of user interface components can be provided for interfacing with chipset 15I28. Such user interface components can include a keyboard 15I34, a microphone 15I36, touch-detection-and-processing circuitry 15I38, a pointing device 15I40 such as a mouse, and so on. In general, inputs to the system can come from any of a variety of machine-generated and/or human-generated sources.

Chipset 15I28 also can interface with one or more data network interfaces 15I30 that can have different physical interfaces. Such data network interfaces 15I30 can include interfaces for wired and wireless local area networks, for broadband wireless networks, as well as personal area networks. Some applications of the methods for generating, displaying and using the GUI disclosed herein can include receiving data over a physical interface 15I31 or be generated by the machine itself by a processor 15I26 analyzing data stored in non-volatile storage 15I44 and/or in memory or RAM 15I46. Further, the machine can receive inputs from a user via devices such as a keyboard 15I34, microphone 15I36, touch-detection-and-processing circuitry 15I38, and pointing device 15I40 and execute appropriate functions such as browsing functions by interpreting these inputs using processor 15I26.

Assessing the impact of a light-emitting system on the circadian cycle may be performed in a variety of ways, including using medical or clinical trials. In such trials, various physiological signals related to the circadian cycle may be monitored for subjects exposed to the light-emitting system. For instance, it is possible to measure the melatonin suppression in the saliva or blood of the subjects. Other physiological signals, including various hormones, may be measured from saliva or blood samples or in other tests. Such protocols are known to those skilled in the art and are discussed in scientific publications. A specific physiological response (such as the level of a specific hormone) may be targeted in such tests, especially for responses known to correlate to a specific medical condition and/or a condition known or believed to be associated with the spectral content of light.

For instance, Brainard discloses a protocol for measuring the melatonin suppression under light exposure. Some steps of the protocol are as follows.

Subjects with normal vision are selected.

At midnight, the subjects enter a dimly lit room, their pupils are dilated and they wait for a period of 2 hrs.

A blood sample if taken.

The subjects are exposed to the test light for 90 min, and a second blood sample is taken.

The melatonin content in the blood samples is determined, and the relative decrease in melatonin compared to that in a control experiment (e.g., no light exposure).

Other testing protocols can be found in various publications such as, for example, in West et al.; in "Blue light from light-emitting diodes elicits a dose-dependent suppression of melatonin in humans" *J. Appl. Physiol.* 110, 619-626 (2011)).

While the present disclosure focuses on light-emitting diode devices, it can be appreciated that the invention also applies to lighting or display systems based on laser diode devices.

In certain embodiments provided by the present disclosure, light sources comprise at least one first LED emission source characterized by a first emission; and at least one second LED emission source characterized by a second emission; wherein the first emission and the second emission are configured to provide a first combined emission and a second combined emission; the first combined emission is characterized by a first SPD and fractions $Fv1$ and $Fc1$; the second combined emission is characterized by a second SPD and fractions $Fv2$ and $Fc2$; $Fv1$ represents the fraction of power of the first SPD in the wavelength range from 400 nm to 440 nm; $Fc1$ represents the fraction of power of the first SPD in the wavelength range from 440 nm to 500 nm; $Fv2$ represents the fraction of power of the second SPD in the wavelength range from 400 nm to 440 nm; $Fc2$ represents the fraction of power of the second SPD in the wavelength range from 440 nm to 500 nm; the first SPD and the second SPD have a color rendering index above 80; $Fv1$ is at least 0.05; $Fc2$ is at least 0.1; and $Fc1$ is less than $Fc2$ by at least 0.02.

In certain embodiments of a light source, the first combined emission is characterized by a first circadian stimulation; the second combined emission is characterized by a second circadian stimulation; and the second circadian stimulation is at least twice the first circadian stimulation.

In certain embodiments of a light source, the first LED emission source comprises at least one LED characterized by a peak emission in the range 405 nm to 430 nm.

In certain embodiments of a light source, the first emission and the second emission are configured to provide a third combined emission; the third combined emission is characterized by a third SPD, a fraction $Fv3$, a fraction $Fc3$, and a third circadian stimulation; $Fv3$ represents the fraction of power of the third SPD in the wavelength range from 400 nm to 440 nm; $Fc3$ represents the fraction of power of the third SPD in the wavelength range from 440 nm to 500 nm; the third SPD has a coloring rendering index above 80; and the first circadian stimulation and the third circadian stimulation are different.

In certain embodiments of a light source, the second emission comprises blue emission from a wavelength down-conversion material.

In certain embodiments of a light source, the second emission comprises direct blue emission from an LED.

In certain embodiments of a light source, one of the combined emissions induces a circadian stimulation similar to a circadian stimulation of a D65 reference illuminant.

In certain embodiments of a light source, one of the combined emissions induces a circadian stimulation that is less than a circadian stimulation of a CIE A reference illuminant.

In certain embodiments of a light source, the at least one first LED emission source and the at least one second LED emission source are configured in an intermixed physical arrangement.

In certain embodiments of a light source, each of the first SPD and the second SPD is characterized by a chromaticity within the white light bounding region 514 of FIG. 5B.

In certain embodiments of a light source, each of the first SPD and the second SPD is characterized by a chromaticity bounded by ±0.005 of a Planckian loci and by ±0.005 of a minimum-hue-shift curve in a CIE chromaticity diagram.

In certain embodiments of a light source, each of the first SPD and the second SPD is characterized by a chromaticity within +/−five Du'v' points of a Planckian loci.

In certain embodiments of a light source, exposure of a subject to the second SPD with an illuminance of 100 lx for ninety minutes results in a suppression of blood melatonin concentration in the subject of at least 20%.

In certain embodiments of a light source, exposure of a subject to the first SPD with an illuminance of 100 lx for ninety minutes results in a suppression blood melatonin concentration in the subject of at most 20%.

In certain embodiments of a light source, $Fc1$ is at most 0.06

In certain embodiments, a display system comprises a first LED emission source characterized by a first emission; and a display configured to emit a first SPD characterized by a first fraction $Fv1$ of power in the range 400 nm to 435 nm; wherein, the display system is characterized by a color gamut of at least 70% of NTSC; the first SPD is substantially white with a CCT in a range from 3000K to 9000K; and $Fv1$ is at least 0.05.

In certain embodiments of a display system, the display comprises an emission spectrum characterized by a circadian stimulation that is less than a circadian stimulation of a reference illuminant having the same CCT.

In certain embodiments of a display system, the display system further comprises a color filter set and a liquid crystal display.

In certain embodiments of a display system, the first SPD is characterized by a peak in the wavelength range from 400 nm to 435 nm at a wavelength w; the color filter set comprises a blue filter characterized by a maximum transmission Tm, and by a transmission Tw at wavelength w; and Tw/Tm>0.8.

In certain embodiments, a display system further comprises a second LED emission source characterized by a second emission, wherein a ratio of the first emission and the second emission are configured to be adjusted to change a circadian stimulation.

In certain embodiments of a display system, the display system is configured for use with a TV, desktop PC, notebook PC, laptop PC, tablet, smartphone, MP3 player.

In certain embodiments of a display system, less than 5% of the power of the first SPD is in a wavelength range from 440 nm to 500 nm.

In certain embodiments, a light source comprises an LED device configured to emit a primary emission; one or more wavelength conversion materials optically coupled to the primary emission; wherein a portion of the primary emission is absorbed by the wavelength conversion materials to produce a secondary emission; wherein a combination of the primary emission and the secondary emission produces white light characterized by an SPD having a CCT and a color rendering index; wherein at least 5% of the SPD is in a wavelength range from 400 nm to 435 nm; wherein a circadian stimulation of the SPD is less than 80% of a circadian stimulation of a reference illuminant having the same color temperature; and wherein the white light is characterized by a color rendering index above 80.

In certain embodiments, of a light source, the primary emission is characterized by a peak wavelength between 405 nm and 425 nm.

In certain embodiments, a lighting system comprises an LED device configured to emit a primary emission characterized by a primary SPD; at least one phosphor optically coupled to the primary emission, wherein the at least one phosphor is characterized by saturable absorption within a blue-cyan wavelength region; wherein the LED device is configured to be controlled by a power signal configured to dim the primary emission; wherein at a first power level the system emits a first SPD characterized by a first fraction fc1 of spectral power in a wavelength range from 440 nm to 500 nm and a first CCT; wherein at a second power level the system emits a second SPD characterized by a second fraction fc2 of spectral power in a wavelength range from 440 nm to 500 nm and a second CCT; and wherein the second power level is less than the first power level and the second fraction fc2 is less than 80% of the first fraction fc1.

In certain embodiments of a lighting system, the second CCT is at least 500K less than the first CCT.

In certain embodiments of a lighting system, where at least 5% of the primary SPD is in a wavelength range from 400 nm to 435 nm.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A light emitter comprising:
   one or more LEDs configured to emit LED light, said one or more LEDs comprising at least a violet LED configured to emit a light with a peak wavelength of 405-435 nm;
   at least one phosphor configured to emit converted light by converting a fraction of said LED light; and
   wherein said light emitter emits an emitted light comprising at least a combination of a fraction of said LED light and said converted light, said emitted light having a spectral power distribution (SPD), said SPD having a first power from 350 nm to 850 nm and a second power from 400 nm to about 440 nm, and a third power from about 440 to about 500 nm, wherein said second power is at least 10% of said first power, wherein the ratio said second power to said third power is at least 1 and no greater than 5, and wherein said SPD has a CRI greater than 80 and an R9 greater than 0.

2. The light emitter of claim 1, wherein at least a portion light emitted from said violet LED pumps said at least one phosphor.

3. The light emitter of claim 1, wherein one or more LEDs comprises a second LED configured to emit a second light, wherein said one or more LEDs are configured to emit at least a first LED light and a second LED light by varying the amount of said at least one violet LED and said at least one second LED in said LED light.

4. The light emitter of claim 3, wherein said second LED comprises a blue LED.

5. The light emitter of claim 4, wherein at least a portion light emitted from said blue LED pumps said at least one phosphor.

6. The light emitter of claim 4, wherein said blue LED has a peak wavelength of 470 nm.

7. The light emitter of claim 1, wherein said second power is at least one of at least 25%, at least 20%, or at least 15%.

8. A light source for emitting emitted light, said light source comprising:
   a first channel for emitting a low circadian stimulation (CS) light, said first channel comprising a violet LED for emitting violet light having a peak wavelength of 405-435 nm, and at least one wavelength converting material for converting a portion of said violet light to a first converted light, wherein said low CS light comprises a combination of said violet light and said first converted light, said low CS light having a first spectral power distribution (SPD) from 350 to 850 nm and fractions Fv1 and Fc1, Fv1 representing a fraction of power of said first SPD in the wavelength range from 400 nm to 440 nm, and Fc1 representing a fraction of power of said first SPD in the wavelength range from 440 nm to 500 nm;
   a second channel for emitting a high CS light, said second channel comprising a blue LED for emitting blue light having a peak wavelength of 440-500 nm, and at least one wavelength converting material for converting a portion of said blue light to a second converted light, wherein said high CS light comprises a combination of said blue light and said second converted light, said high CS light having a second SPD from 350 to 850 nm and fractions Fv2 and Fc2, Fv2 representing a fraction of power of said second SPD in the wavelength range from 400 nm to 440 nm, and Fc2 representing a fraction of power of said second SPD in the wavelength range from 440 nm to 500 nm; and
   circuitry for driving said first and second channels independently such that said emitted light is at least one of said low CS light, said high CS light, or a combination of said low CS light and said high CS light.

9. The light source of claim 8, wherein said violet light has a peak wavelength of 405-430 nm.

10. The light source of claim 9, wherein said violet light has a peak wavelength of 425 nm.

11. The light source of claim 8, wherein said blue light has a peak wavelength of 440-470 nm.

12. The light source of claim 11, wherein said blue light has a peak wavelength of 470 nm.

13. The light source of claim 8, wherein CS of said high CS light is more than 2 times that of said low CS light.

14. The light source of claim 8, wherein CS of said high CS light is more than 3 times that of said low CS light.

15. The light source of claim 8, wherein Fc1 is less than 0.05 and Fc2 is at least 0.1.

16. The light source of claim 8, wherein Fc1 is less than 0.01.

17. The light source of claim 8, wherein Fv1 is at least 0.05.

18. The light source of claim 8, wherein Fv1 is at least 0.2.

19. The light source of claim 8, wherein said first and second channels are contained in separate packages.

20. The light source of claim 8, wherein said circuitry is configured to adjust the ratio of said low CS light and said high CS light without changing CCT or chromaticity of said emitted light.

21. The light source of claim 8, further comprising a third channel having a third LED different from said violet LED and said blue LED.

22. The light source of claim 8, further comprising at least one control circuit configured to learn from user behavior to regulate said emitted light between said low CS light and said high CS light.

* * * * *